United States Patent
Shaolian et al.

(10) Patent No.: US 7,083,621 B2
(45) Date of Patent: Aug. 1, 2006

(54) ARTICULATING SPINAL FIXATION ROD AND SYSTEM

(75) Inventors: Samuel M. Shaolian, Newport Beach, CA (US); Thanh Van Nguyen, Irvine, CA (US); To V. Pham, Trabuco Canyon, CA (US); George P. Teitelbaum, Santa Monica, CA (US)

(73) Assignee: SDGI Holdings, Inc., Wilmington, DE (US)

( * ) Notice: Subject to any disclaimer, the term of this patent is extended or adjusted under 35 U.S.C. 154(b) by 107 days.

(21) Appl. No.: 10/642,399

(22) Filed: Aug. 15, 2003

(65) Prior Publication Data

US 2005/0038432 A1  Feb. 17, 2005

(51) Int. Cl.
*A61B 17/70* (2006.01)
(52) U.S. Cl. .......................... 606/61; 606/73
(58) Field of Classification Search ................ 606/61, 606/73
See application file for complete search history.

(56) References Cited

U.S. PATENT DOCUMENTS

| | | |
|---|---|---|
| 2,338,159 A | 1/1944 | Appleton |
| 4,041,939 A | 8/1977 | Hall |
| 4,289,123 A | 9/1981 | Dunn |
| 4,335,715 A | 6/1982 | Kirkley |
| 4,648,388 A | 3/1987 | Steffee |
| 4,722,331 A | 2/1988 | Fox |
| 4,743,260 A | 5/1988 | Burton |
| 4,771,767 A * | 9/1988 | Steffee ................ 606/61 |
| 4,883,048 A | 11/1989 | Purnell et al. |
| 4,887,595 A | 12/1989 | Heinig et al. |
| 4,892,550 A | 1/1990 | Huebsch |
| 4,920,958 A | 5/1990 | Walt et al. |
| 4,957,495 A | 9/1990 | Kluger |
| 4,998,936 A | 3/1991 | Mehdian |
| 5,000,165 A | 3/1991 | Watanabe |
| 5,030,220 A | 7/1991 | Howland |
| 5,084,049 A | 1/1992 | Asher et al. |
| 5,112,337 A | 5/1992 | Paulos et al. |
| 5,163,940 A | 11/1992 | Bourque |

(Continued)

FOREIGN PATENT DOCUMENTS

DE   197 26 754 A 1   2/1999

(Continued)

OTHER PUBLICATIONS

Muller et al., "A Keyhole Approach for Endoscopically Assisted Pedicle Screw Fixation in Lumbar Spine Instability". Neurosurgery, vol. 47, No. 1, Jul. 2000, pp. 85-96.

(Continued)

*Primary Examiner*—David O. Reip
(74) *Attorney, Agent, or Firm*—Knobbe, Martens, Olson, & Bear, LLP.

(57) ABSTRACT

The present invention relates generally to systems and methods for aligning and implanting orthopedic fixation or stabilization implants within the body. In one embodiment, the system includes at least two bone anchors, at least one of which is provided with a transverse portal and a locking member. In one aspect, the system also includes at least one linkage rod, for linking two or more bone anchors through their respective locking members. The linking rod may include at least one angularly adjustable joint, which may be fixed by actuating the locking member. The bone anchors and the linkage rod may be locked into place to form a spinal fusion or fixation prosthesis.

38 Claims, 58 Drawing Sheets

U.S. PATENT DOCUMENTS

| | | |
|---|---|---|
| 5,171,279 A | 12/1992 | Mathews |
| 5,176,680 A | 1/1993 | Vignaud et al. |
| 5,242,443 A | 9/1993 | Kambin |
| 5,242,444 A | 9/1993 | MacMillan |
| 5,281,223 A | 1/1994 | Ray |
| 5,334,205 A | 8/1994 | Cain |
| 5,342,361 A | 8/1994 | Yaun et al. |
| 5,357,983 A | 10/1994 | Mathews |
| 5,397,363 A | 3/1995 | Gelbarb |
| 5,409,488 A * | 4/1995 | Ulrich .................. 606/61 |
| 5,474,551 A | 12/1995 | Finn et al. |
| 5,486,174 A | 1/1996 | Fournet-Fayard et al. |
| 5,496,322 A | 3/1996 | Mathews |
| 5,520,689 A | 5/1996 | Schlapfer et al. |
| 5,540,688 A * | 7/1996 | Navas .................. 606/61 |
| 5,549,679 A | 8/1996 | Kuslich |
| 5,562,661 A | 10/1996 | Yoshimi et al. |
| 5,569,248 A | 10/1996 | Mathews |
| 5,584,887 A | 12/1996 | Kambin |
| 5,591,165 A | 1/1997 | Jackson |
| 5,591,167 A | 1/1997 | Laurain et al. |
| 5,613,971 A | 3/1997 | Lower et al. |
| 5,643,273 A | 7/1997 | Clark |
| 5,649,925 A | 7/1997 | Alacreu |
| 5,658,286 A | 8/1997 | Sava |
| 5,681,320 A | 10/1997 | McGuire |
| 5,704,937 A | 1/1998 | Martin |
| 5,728,097 A | 3/1998 | Mathews |
| 5,752,955 A | 5/1998 | Errico |
| 5,800,435 A | 9/1998 | Errico et al. |
| 5,891,150 A | 4/1999 | Chan |
| 5,910,142 A | 6/1999 | Tatar |
| 5,938,663 A | 8/1999 | Petreto |
| 5,961,516 A * | 10/1999 | Graf .................. 606/61 |
| 6,033,406 A | 3/2000 | Mathews |
| 6,099,528 A | 8/2000 | Saurat |
| 6,102,912 A | 8/2000 | Cazin et al. |
| 6,106,530 A | 8/2000 | Harada |
| 6,120,511 A | 9/2000 | Chan |
| 6,126,689 A | 10/2000 | Brett |
| 6,127,597 A | 10/2000 | Beyar et al. |
| 6,129,763 A | 10/2000 | Chauvin et al. |
| 6,162,223 A | 12/2000 | Orsak et al. |
| 6,175,758 B1 | 1/2001 | Kambin |
| 6,187,011 B1 | 2/2001 | Torrie |
| 6,206,922 B1 | 3/2001 | Zdeblick et al. |
| 6,226,548 B1 | 5/2001 | Foley et al. |
| 6,235,028 B1 | 5/2001 | Brumfield et al. |
| 6,296,644 B1 | 10/2001 | Saurat |
| 6,402,784 B1 | 6/2002 | Wardlaw |
| 6,425,923 B1 | 7/2002 | Stalcup et al. |
| 6,530,926 B1 | 3/2003 | Davison |
| 6,530,929 B1 | 3/2003 | Justis et al. |
| 6,558,386 B1 | 5/2003 | Cragg |
| 6,558,390 B1 | 5/2003 | Craig |
| 6,582,467 B1 | 6/2003 | Teitelbaum et al. |
| 6,802,844 B1 * | 10/2004 | Ferree .................. 606/61 |
| 2002/0022764 A1 | 2/2002 | Smith et al. |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0082601 A1 | 6/2002 | Toyama et al. |
| 2002/0161368 A1 | 10/2002 | Foley et al. |
| 2002/0198526 A1 | 12/2002 | Shaolian et al. |
| 2003/0060826 A1 | 3/2003 | Foley et al. |
| 2004/0006341 A1 | 1/2004 | Shaolian et al. |
| 2004/0006344 A1 | 1/2004 | Nguyen et al. |

FOREIGN PATENT DOCUMENTS

| | | |
|---|---|---|
| WO | WO 97/30666 | 8/1997 |
| WO | WO 97/38639 | 10/1997 |
| WO | WO 99/09902 | 3/1999 |
| WO | WO 99/15097 | 4/1999 |

OTHER PUBLICATIONS

International Search Report for Application No. PCT/US04/26112 (the PCT counterpart of the parent application).

* cited by examiner

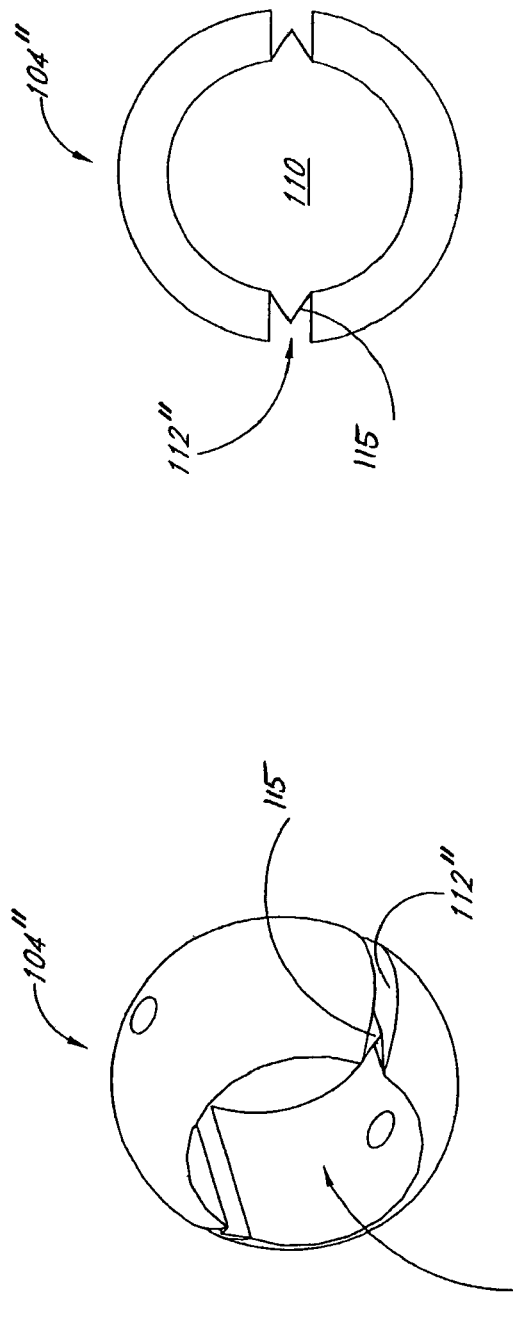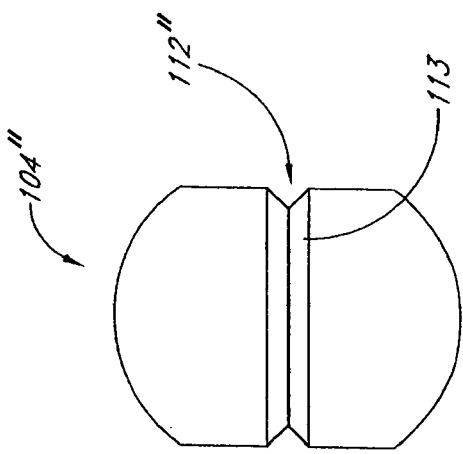

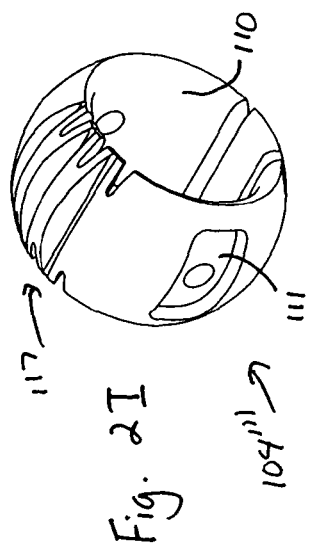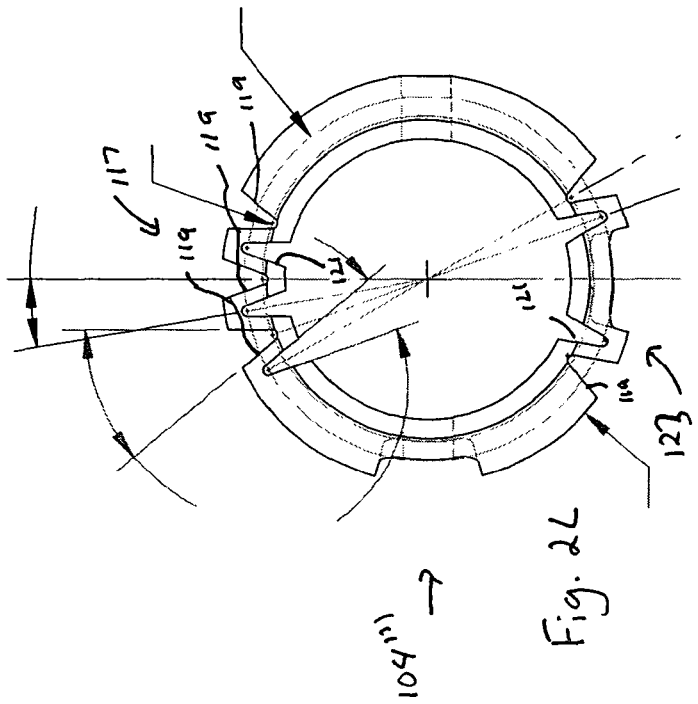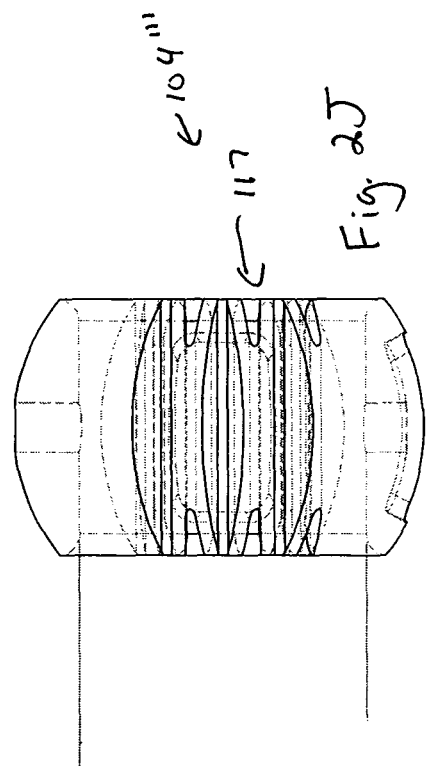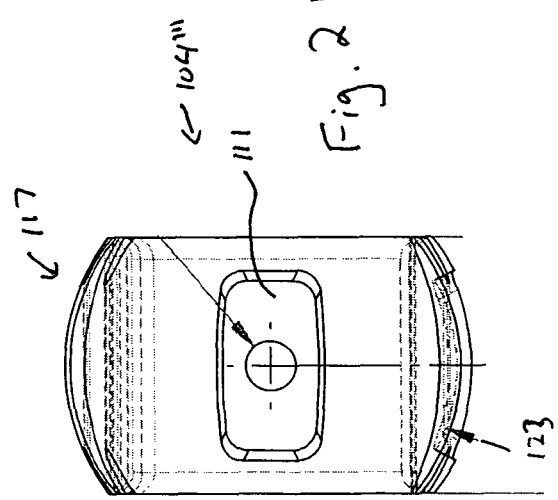

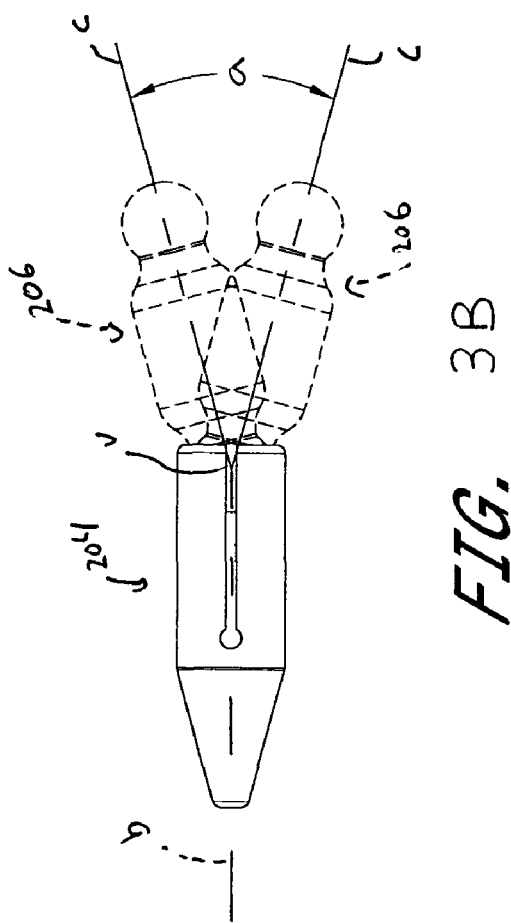
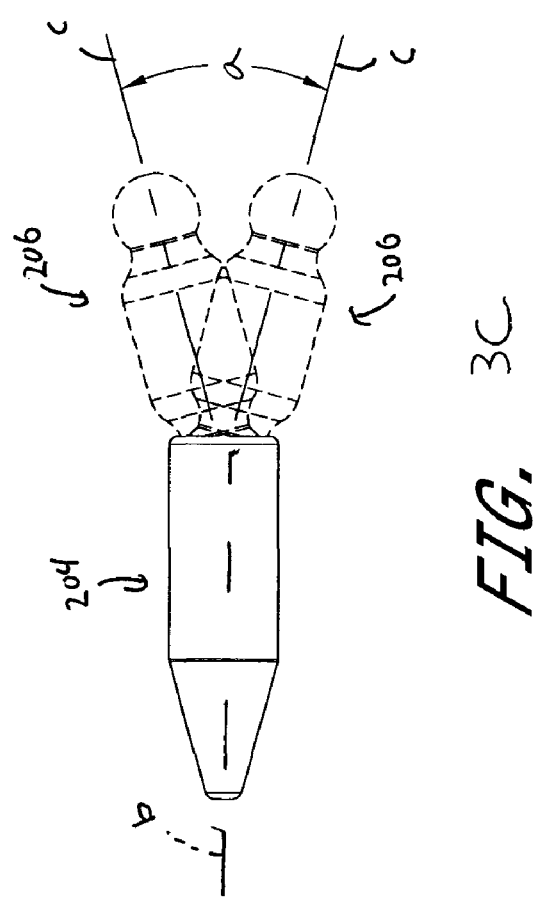

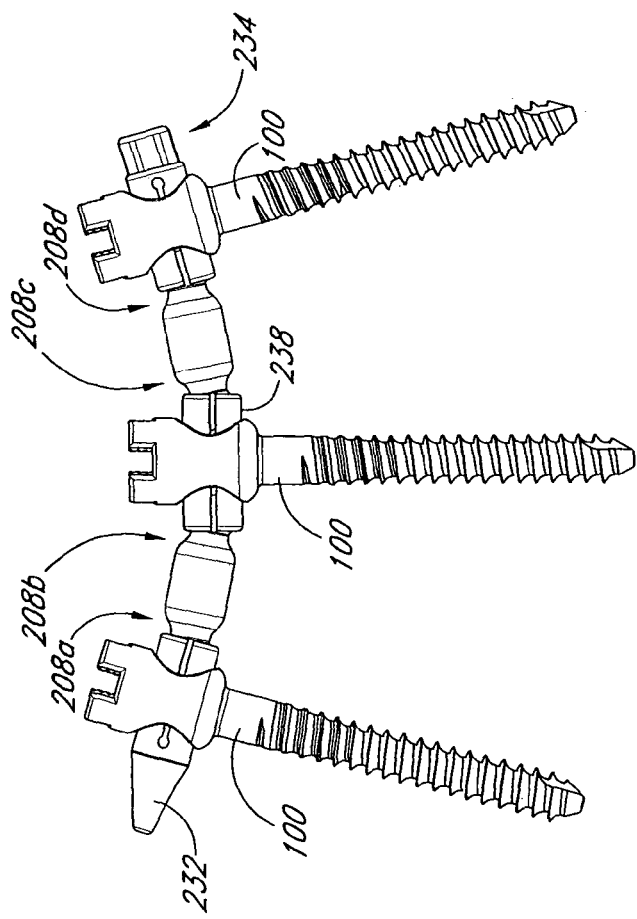
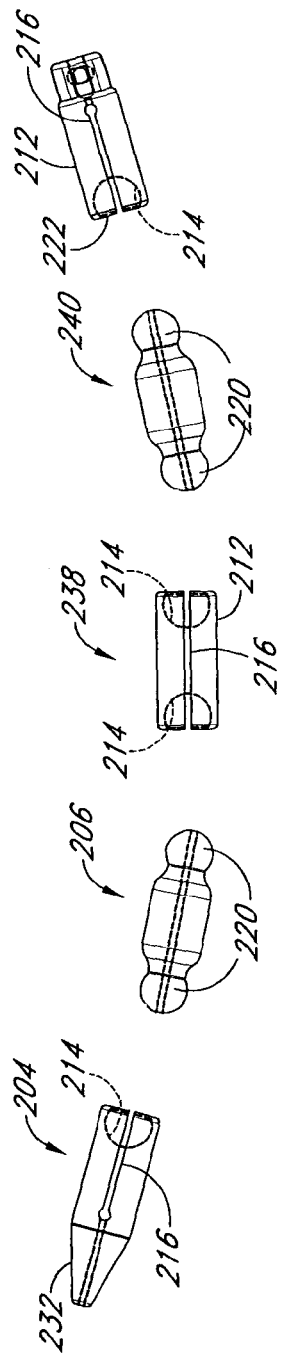
FIG. 4A
FIG. 4B

ARTICULATING SPINAL FIXATION ROD AND SYSTEM

BACKGROUND OF THE INVENTION

1. Field of the Invention

The present invention relates generally to medical devices and, more particularly, to systems for aligning and implanting orthopedic fixation or stabilization implants within the body. In one application, the present invention relates to minimally invasive procedures and devices for implanting posterior instrumentation.

2. Description of the Related Art

The human vertebrae and associated connective elements are subject to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to these diseases, conditions, injuries and manipulations often result from the displacement of all or part of a vertebra from the remainder of the vertebral column. A variety of methods have been developed to restore the displaced vertebrae or portions of displaced vertebrae to their normal position and to fix them within the vertebral column. For example, open reduction with screw fixation is one currently used method. The surgical procedure of attaching two or more parts of a bone with pins, screws, rods and plates requires an incision into the tissue surrounding the bone and the drilling of one or more holes through the bone parts to be joined. Due to the significant variation in bone size, configuration, and load requirements, a wide variety of bone fixation devices have been developed in the prior art. In general, the current standard of care relies upon a variety of metal wires, screws, rods, plates and clamps to stabilize the bone fragments during the healing or fusing process. These methods, however, are associated with a variety of disadvantages, such as morbidity, high costs, lengthy in-patient hospital stays and the pain associated with open procedures.

Therefore, devices and methods are needed for repositioning and fixing displaced vertebrae or portions of displaced vertebrae which cause less pain and potential complications. Preferably, the devices are implantable through a minimally invasive procedure.

SUMMARY OF THE INVENTION

In accordance with one aspect of the present invention, a system is provided for the minimally invasive implantation of posterior fixation hardware. The system generally includes at least two bone anchors with transverse portals and locking members. The system also generally includes a linking rod for linking two or more bone anchors through their respective portals. The rod is provided with at least one angularly adjustable joint. In many clinical situations, the rod is provided with more than one angularly adjustable joint. The system may also include a driver for inserting the bone anchor into a bone and locking the angularly adjustable joint with the locking member. In one embodiment, an insertion tool is provided for the insertion of the linkage rod. The bone anchors, the linkage rod and the joints may be fixed by the locking of the locking members on the bone anchors, to subcutaneously form a prosthesis.

In another aspect of the invention, an implantable fixation rod comprises a first segment, having a proximal end and a distal end and a second segment, having a proximal end and a distal end. A joint is positioned between the first segment and the second segment. The joint is convertable between a first state in which the first and second segments are movable with respect to each other, and a second state in which the first and second segments are fixed with respect to each other.

In another aspect of the present invention, a method is provided for the minimally invasive implantation of posterior fixation hardware. In one embodiment, the method comprises the insertion of a first bone anchor, having a locking member and a transverse portal into a first vertebral body. A second bone anchor, having a locking member and a transverse portal, is inserted into a second vertebral body. The first and second vertebral bodies may be adjacent to each other, or separated by one or more other vertebral body or bodies. A linkage rod with at least one angularly adjustable joint is inserted through the portals of both bone anchors. The locking member of each bone anchor is then locked, fixing the position of at least one of the angularly adjustable joints, and securing the linkage rod within the bone anchor, to form a prosthesis.

In accordance with another embodiment of the present invention, the method further comprises the insertion of another bone anchor with a transverse portal and a locking member into another vertebral body. This latter vertebral body may be adjacent to either or both of the first and second vertebral bodies, or separated from both the first and second vertebral bodies. The linkage rod is inserted through the transverse portals of the bone anchors to form the prosthesis.

In accordance with another embodiment of the present invention, the method additionally includes the placement of one or more guide wires. A guide wire may be inserted into a bone to define a path for the insertion of a bone anchor. Another guide wire may be threaded through the portals of two or more bone anchors, to guide the insertion of the linkage rod.

In any of the foregoing systems and methods, the guide wire may be replaced or supplemented by a flexible guide tube. In such implementations of the invention, the bone anchor and/or the linkage rod may be advanced through the interior of the guide tube.

Further features and advantages of the present invention will become apparent to those skilled in the art in view of the detailed description of preferred embodiments which follows, when considered together with the attached drawings.

BRIEF DESCRIPTION OF THE DRAWINGS

FIGS. 2F–2H illustrate another embodiment of a connector.

FIGS. 2I–2L illustrate another embodiment of a connector.

FIG. 3B is an assembled side view of a portion of the fixation rod of FIG. 3 showing the range of angular adjustment.

FIG. 3C is an assembled top view of a portion of the fixation rod of FIG. 3B showing the range of angular adjustment.

FIG. 4A is another view of the system of FIG. 4.

FIG. 4B is an unassembled side view of the fixation rod of FIG. 4.

DETAILED DESCRIPTION OF THE PREFERRED EMBODIMENTS

Although the application of the present invention will be disclosed primarily in the context of a spinal fixation procedure, the systems and methods disclosed herein are intended for use in a wide variety of medical applications where the minimally invasive implantation of an attachment, bulking, brace, support, fixation or other prosthesis may be desirable. The systems and methods disclosed herein may find also utility in a variety of medical procedures where it is desirable introduce an implant into the body in a flexible configuration and thereafter convert the implant to a substantially rigid configuration (e.g., splinting or stabilizing a broken or fractured bone).

One advantage of the prosthesis formation described in the various embodiments of the present invention is the ability to access a treatment site through minimally invasive pathways, while allowing the formation of a relatively larger prosthesis at the treatment site. In one embodiment, various components of a prosthesis are inserted into a patient through minimally invasive pathways, then joined to form a single prosthesis. This is facilitated by providing a linkage rod with angularly adjustable joints, which provide leeway or angular adjustability as the linkage rod is threaded through a plurality of bone anchors. Afterwards, the joints in the linkage rod may be locked to fix or set the linkage rod in a desired configuration.

A corollary advantage of several embodiments is the ability to unlock and adjust joints in the linkage rod, to set the prosthesis in other desirable configurations during or even after its implantation and formation. The prosthesis may thus be adjusted in subsequent procedures.

The systems and methods for spinal fixation according to various embodiments of the present invention minimize procedure morbidity by avoiding open surgical cutdowns or other invasive access procedures. The basic percutaneous access, bone screw construction and implantation methods, and methods and structures for percutaneously positioning a fixation rod across bone screws, all of which are useful in the practice of the present invention, are disclosed in U.S. patent application Ser. No. 09/747,066, entitled Percutaneous Vertebral Fusion System, to Teitelbaum, filed Dec. 21, 2000; U.S. patent application Ser. No. 09/943,636 to Shaolian et al., entitled Formable Orthopedic Fixation System, filed Aug. 29, 2001; U.S. patent application Ser. No. 09/976,459 to Teitelbaum et al., entitled Formable Orthopedic Fixation System with Cross-Linking, filed Oct. 10, 2001; and U.S. patent application Ser. No. 10/161,554 to Shaolian et al., entitled Formed in Place Fixation System with Thermal Acceleration, filed May 31, 2002; U.S. patent application Ser. No. 10/462,098, filed Jun. 13, 2003 and entitled System and Method for Minimally Invasive Posterior Fixation, the disclosures of all of which are hereby incorporated in their entireties by reference herein.

Figure 1:
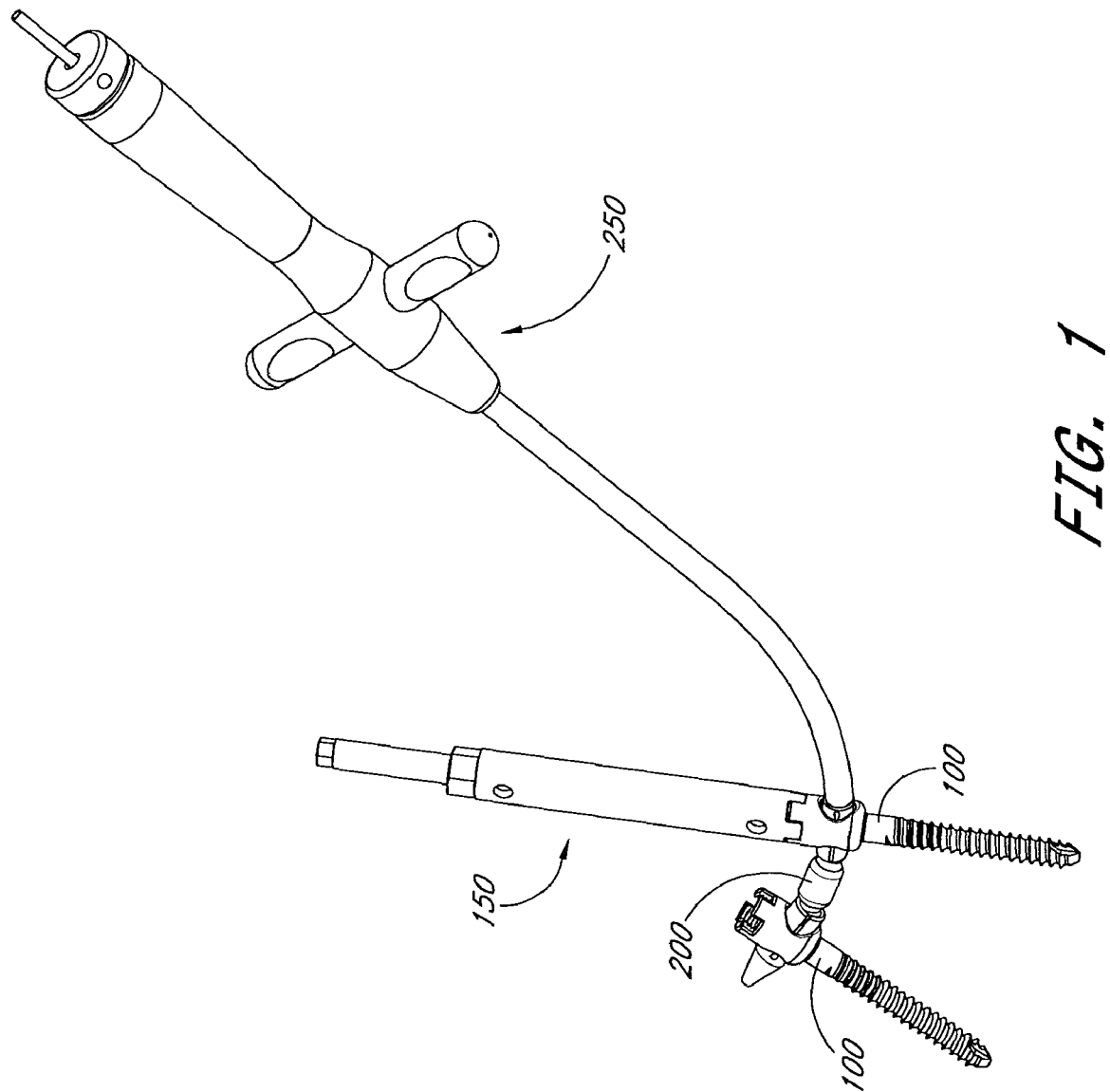
FIG. 1 is an overview of a system for minimally invasive posterior spinal fixation according to one embodiment of the present invention.

An overview of a system for minimally invasive posterior spinal fixation according to one embodiment of the present invention is provided in FIG. 1. The system includes at least two and optionally three or four or more bone anchors 100 and an articulating jointed linkage rod 200. In FIG. 1, the bone anchors are shown connected by the jointed linkage rod 200. The system may also include a driver 150, shown engaging one of the bone anchors 100, and an insertion tool 250, shown connected to the linkage rod 200. Although these components will be described primarily in the context of a single linkage rod connected to two bone anchors, a normal fusion application will typically involve the implantation of two linkage rods, each carried by two or more bone anchors, bilaterally symmetrically mounted on the spine as is well understood in the art.

Figure 2:
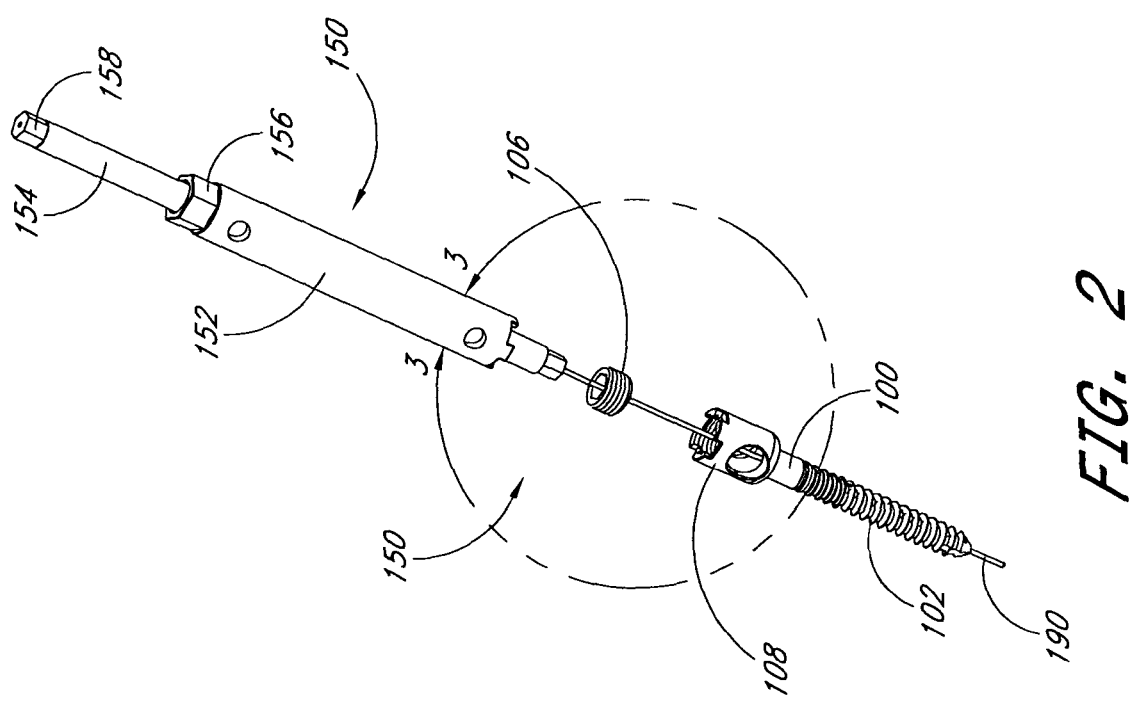
FIG. 2 is an exploded view of the bone anchor and the driver of FIG. 1.

FIG. 2 shows an exploded view of the bone anchor 100 and the driver 150. The bone anchor 100 is provided with threads 102 by which it is screwed into a vertebral body. A locking cap 106 is disposed within the head 108 of the bone anchor 100.

The driver 150 comprises an outer adapter 152 concentrically arranged around an inner adapter 154. Either adapter may be freely rotated with respect to the other. The outer adapter 152 is adapted to engage the head 108, to screw the bone anchor 100 into a bone. The inner adapter 154 is adapted to engage the locking cap 106, to secure the fixation rod 200 within the head 108. In one embodiment, the hexagonal proximal end 156 of the outer adapter 152 allows torque to be applied to the outer adapter 152 by means of a wrench, a spanner or another tool. Similarly, the hexagonal proximal end 158 of the inner adapter 154 allows torque to be applied to the inner adapter 154.

Releasable, rotational engagement between the driver and the bone anchor may be accomplished in any of a variety of ways. In the illustrated embodiment, the distal end the inner adapter 154 is provided with at least one surface for cooperating with a complimentary surface on the proximal end of the bone anchor 100, for transmitting torque from the inner adapter 154 to the bone anchor 100, to enable transmission of torque from the inner adapter 154 to locking cap 106. Similarly, the distal end of the outer adapter 152 is provided with at least one surface for cooperating with a complimentary surface on the proximal end of the bone anchor 100, for transmitted torque from the outer adapter 152 to the bone anchor 100 to enable credible engagement between the bone anchor 100 and the vertebral body.

In one embodiment, the bone anchor 100, its locking cap 106, and the inner adapter 154 are all provided with a central axial lumen through which a guide wire 190 may pass.

Figure 2A:
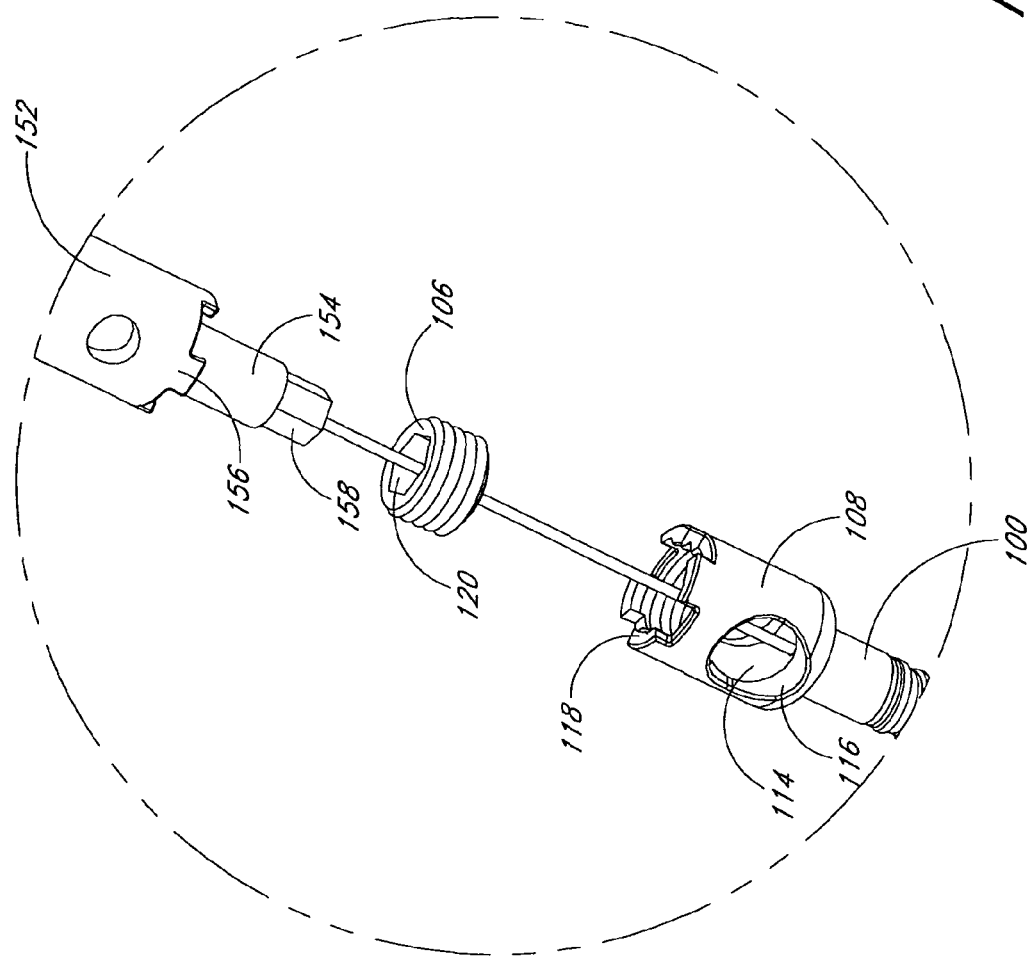
FIG. 2A is an enlarged view of the circled area in FIG. 2.

FIG. 2A is an enlarged view of the circled area in FIG. 2, showing the proximal head 108 of the bone anchor 100 and the distal ends of the outer adapter 152 and the inner adapter 154. The locking cap 106 is shown outside the head 108.

A transverse portal 116 extends through the head 108 along an axis approximately perpendicular to the central axis of the bone anchor 100. While the transverse portal 116 of the head 108 is illustrated as circular, it may be of different shapes in other embodiments, depending upon the cross sectional shape of the fixation rod (e.g. oval, elliptical, rectangular, square, etc.). The diameter of the transverse portal 116 is generally larger than the diameter of the corresponding portions of the fixation rod 200 such that before the locking cap 106 is tightened at least a portion of the fixation rod 200 may be inserted through the portal 116. In the illustrated embodiment, the portal 116 includes a race or groove 114 within the head 108. The groove 114 is preferably configured to be slightly larger than the diameter of the corresponding portions of the fixation rod 200 but yet have a smaller diameter than the portal 116. In other embodiments, the groove 114 may be eliminated from the transverse portal 116.

Figure 2B:
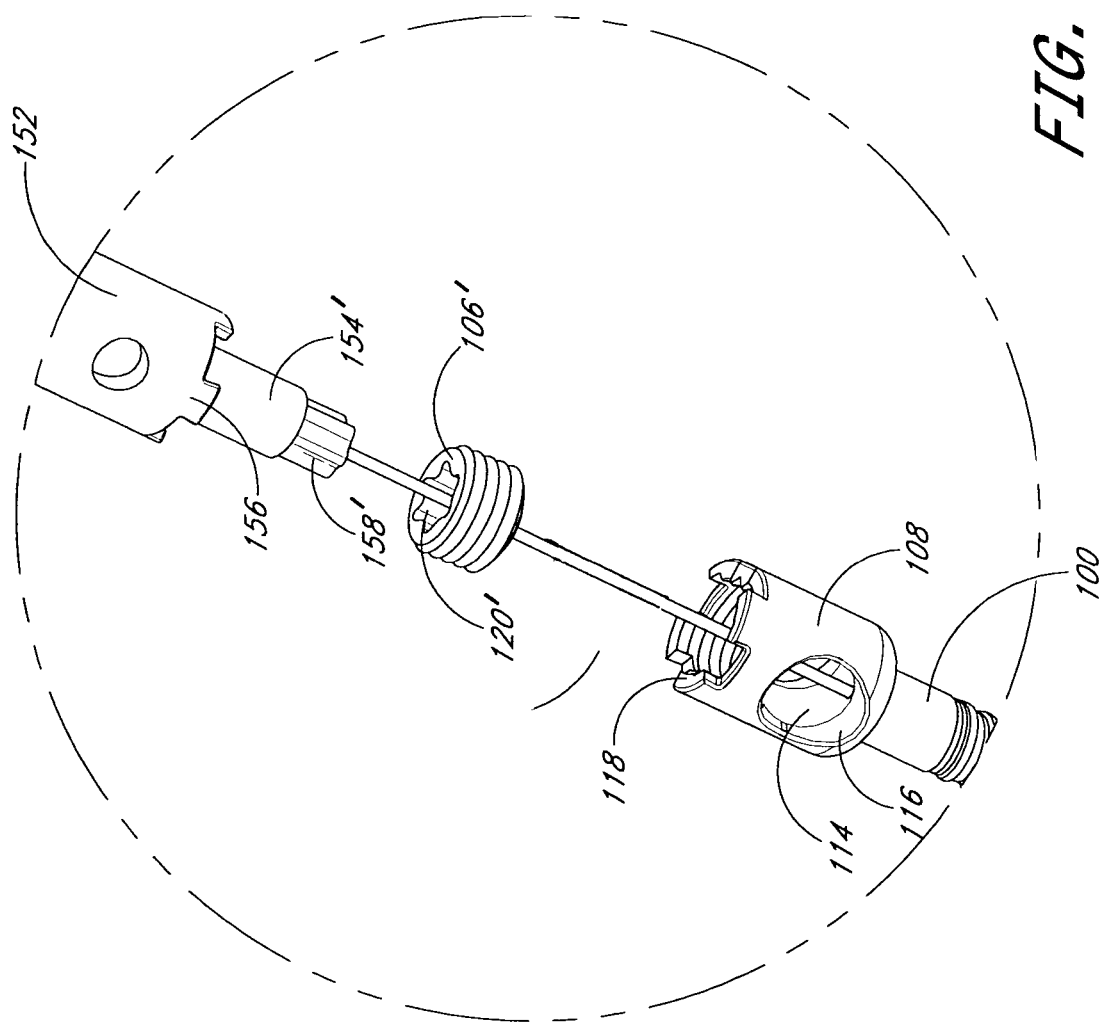
FIG. 2B illustrates a locking cap and its complementary inner adapter according to yet another embodiment.

FIG. 2B is similar to FIG. 2A above, and illustrates an inner adapter 154' and a locking cap 106' according to another embodiment. In one embodiment, the inner adapter 154' is provided with a Torx distal end 158' which is adapted to engage a complementary Torx opening 120' at the top of the locking cap 106'. Any of a variety of complementary surface structures may be used, as will be understood in the art in view of the disclosure herein.

Figure 2C:
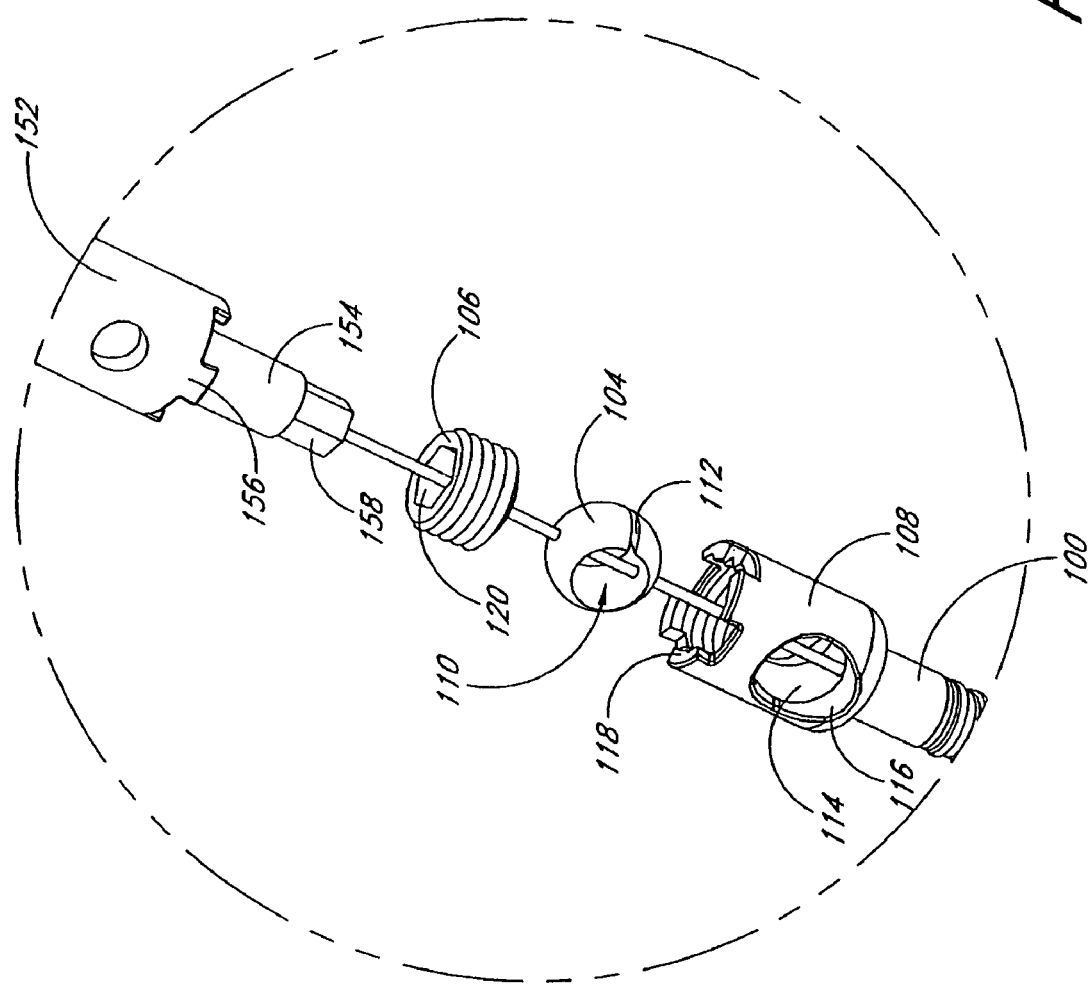
FIG. 2C illustrates a connector, a locking cap and its complementary inner adapter according to yet another embodiment.

In yet another embodiment, the head 108 of bone anchor 100 may also be provided with an angularly adjustable connector 104 as shown in FIG. 2C. The connector 104 may be disposed within the head 108 beneath the locking cap 106. In one embodiment, the connector 104 is spherical with an aperture 110 extending therethrough, and a gap 112 in its circumference, such that it is approximately C-shaped when viewed along the central axis of the aperture 110. The aperture 110 is adapted for the insertion of the linkage rod (not shown), and has a diameter slightly larger than that of the linkage rod. One skilled in the art will understand that the connector 104 can be provided in a variety of suitable shapes.

In one embodiment, the connector 104 is seated on the race or groove 114 which may be provided in the head 108 as described above. In such embodiments, the groove 114 is preferably provided with a complementary surface to the spherical exterior surface of the connector 104. The connector 104 may rotate on any axis within the head 108 of the bone anchor (or bone screw) 100. The locking cap 106 may be threaded into the head 108 to lock the connector 104 against the linkage rod 200, by compressing the groove 114, fixing the connector 104 within the head 108. The bottom of the locking cap 106 may be provided with a concave surface (not shown) which is complementary to the spherical exterior surface of the connector 104.

While the aperture 110 of the connector 104 is illustrated as circular, they may be of different shapes in other embodiments, depending upon the cross sectional shape of the fixation rod (e.g. oval, elliptical, rectangular, square, etc.). The diameter of the transverse portal 116 is generally smaller than the outside diameter of the uncompressed connector 104 but greater than the inside diameter of the aperture 110. Before the locking cap 106 is tightened, the connector 104 may rotate on any axis within the head 108 to accommodate different entrance angles for the fixation rod. Thus the central axis of the aperture 110 and the central axis of the transverse portal 116 may be coaxial or angularly offset.

In one embodiment, the threading of the locking cap 106 into the head 108 compresses the connector 104, decreasing the width of the gap 112 and reducing the cross sectional area of the aperture 110. This secures a linkage rod (not shown) extending through the transverse portal 116 of the bone anchor 100 within the aperture 110. The tightening of the locking cap 106 into the head 108 also fixes the rotational position of the connector 104 within the head 108.

Figure 2D:
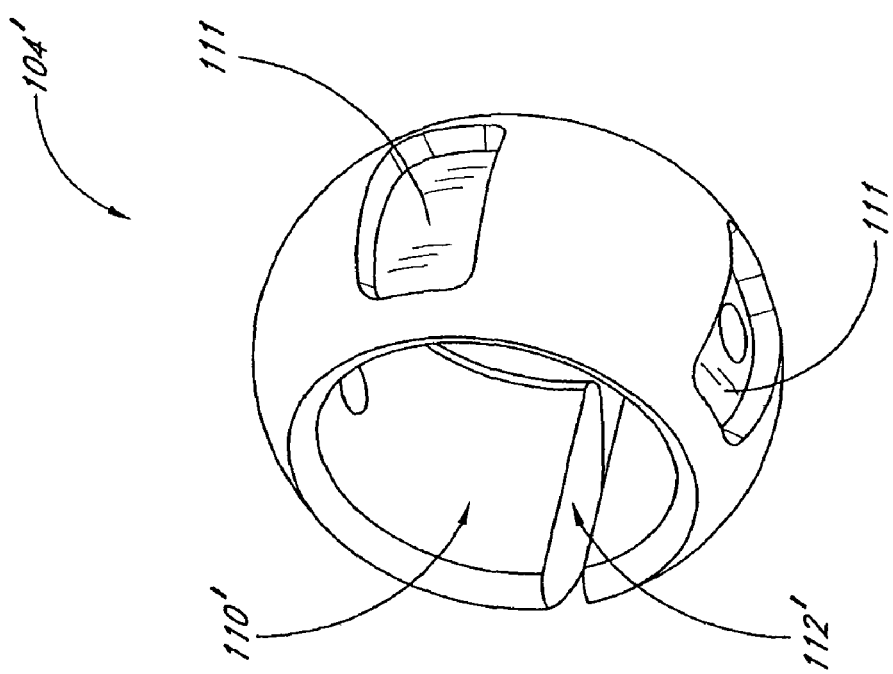
FIG. 2D illustrates an angularly adjustable connector with rotation limits according to another embodiment.
Figure 2E:
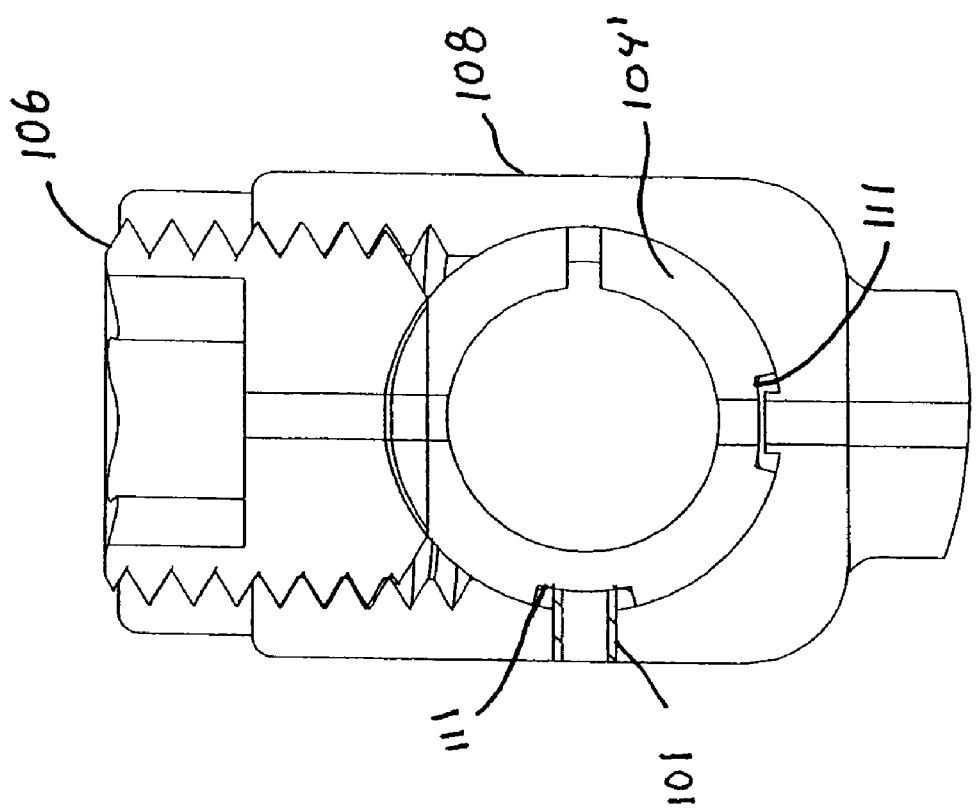
FIG. 2E is a cross-sectional view of an angularly adjustable connector with rotation limits positioned within a head of a bone anchor according to another embodiment.

FIG. 2D illustrates an alternate connector 104'. Similar to the connector 104 described above, the connector 104' is provided with an aperture 110' having a longitudinal axis and a gap 112'. The spherical exterior surface of the connector 104' is provided with one or two or three or more surface structures such as projections or indentations 111. The indentations 111 receive complementary surface structures such as projections provided within the head 108 of the bone anchor 100 to limit the degree of rotation of the connector 104' within the head 108. For example, FIG. 2E illustrates an exemplary embodiment wherein the complementary surface structure comprises a pin 101 that may be laser welded or otherwise coupled to or integrally formed with the screw head 108. As described above, the pin 101 interacts with the indentation 111 to limit the degree of rotation of the connector 104' within the head 108. In one specific embodiment, the connector 104' is limited to about 30 degrees of rotation on any axis within the head 108, from the longitudinal axis through the transverse portal 116. In other embodiments, the connector 104' may be limited to a range of up to about 60 degrees of rotation from the longitudinal axis. In one embodiment, the connector 104' is limited to no more than about 5 degrees or about 10 degrees of rotation on any axis from the longitudinal axis. In general, the rotation of the connector 104' is limited such that the aperture will always be exposed through transverse portal 116 to the linkage rod 200.

FIG. 2F illustrates a connector 104" according to another embodiment. Similar to the connectors 104 and 104' described above, the connector 104" is provided with an aperture 110" and one or more compressible gaps 112". The gaps 112" are provided with a compressible material which compresses when the locking cap 106' tightens the connector 104" against the groove 114 within the head 108. Compressible material, including any of a variety of compressible polymeric materials known in the medical device arts can be used according to several embodiments of the present invention. One skilled in the art will appreciate that other suitable flexible or compressible materials may also be used. In addition, any of a variety of metal (stainless steel, titanium, etc.) connectors 104 may be configured such that the aperture 110 is moveable from a first, large cross-section, for receiving a linkage rod 200 therethrough, to a second, reduced cross section for locking the linkage rod 200 in place. This may be accomplished by providing opposing components forming the side wall of the connector 104 with any of a variety of interlocking structures such as ramp and pawl ratchet structures, or sliding fit structures which permit a reduction in the diameter in the aperture 110 under compressive force from the locking cap 106.

In an alternate embodiment, portions or all of the connector 104 comprise a compressible media such as an open cell foam, closed cell foam or solid compressible material. Structures comprising polyethylene, PEEK, nylon, and other polymers known in the medical arts may be utilized, depending upon the construction and desired compressibility. In general, the combination of material and the structure of the connector 104 is sufficient to allow angular adjustment of the longitudinal axis of the aperture 110, to accommodate various entrance angles of the linkage rod 200. After the linkage rod 200 has been positioned within the aperture 110, rotational and/or axial movement of a locking element such as locking cap 106 functions to both prevent axial movement of the linkage rod 200 within the aperture 110, as well as prevent further angular adjustment of the longitudinal axis of the aperture 110 with respect to the longitudinal axis of the bone anchor 100.

FIGS. 2G–2H illustrate the connector 104", the aperture 110", the gaps 112", and a compressible or foldable membrane or link 115 in greater detail. FIG. 2F is an isometric view of the connector 104". FIG. 2G is a front plan view of the connector 104" viewed along the central axis of the aperture 110". FIG. 2H is the corresponding side plan view. In the embodiment illustrated in FIGS. 2F–2H, the compressible link is formed by grinding, laser etching, molding or otherwise forming a recess such as a V-shaped channel 113 that leaves a thin link 115 which folds flat when the connector 104" is compressed. One of ordinary skill in the art will understand that compressible materials and structures can be provided in a variety of suitable shapes and forms.

In one embodiment, the apertures 110' and 110" have a tendency to return to their original diameters even after the connectors 104 and 104', respectively, are compressed by the locking cap 106 against the groove 114 within the head 108. This tendency results from the resiliency of the metal, alloy or other material used to make the connectors 104 and 104'. The use of compressible material, such as V-shaped channels 113 in the gaps 112" of the connector 104", reduces or eliminates this tendency and may allow a linkage rod (not shown) to be more firmly secured within the aperture 110". One skilled in the art will understand that the connectors 104 and 104' can be made from lower resiliency materials which can also reduce or eliminate the tendency of apertures 110' and 110" to return to their original diameters.

FIGS. 2I–L illustrate another embodiment of a connector 104''' according to another embodiment. In this embodiment, the connector 104''' is provided with an aperture 110 and an indentation 111 as described. A top portion of the connector 104''' is provided with a compressible material or foldable link 117, which in comprises a series V-shaped channels formed into the body of the connector 104'''. In the illustrated arrangements, the channels comprise a series of 40 degree V-shaped channels 119 formed on the outer surface of the connector 104''' and 20 degree V-shaped channels 121 on the inner surface of the connector 104'''. In a similar manner, a foldable link 123 is provided on a lower portion of the connector 104'''. In this embodiment, as the locking cap 106 is tightened the top and bottom portions of the connector 104" are deformed and laterally depressed so as to secure the fixation rod within the aperture 110.

Further details and additional embodiments of a bone anchor utilizing a connector 104 can be found in co-pending U.S. patent application Ser. No. 10/462,098, filed Jun. 13, 2003, and entitled System and Method for Minimally Invasive Posterior Fixation, which was incorporated by reference above.

As discussed above with reference to FIG. 2, in one embodiment, the outer adapter 152 is adapted to engage the head 108, and the inner adapter 154 is adapted to engage the locking cap 106. In the illustrated embodiment, projections 156 on the distal end of the outer adapter 152 are adapted to engage complementary projections 118 on the head 108 of the bone anchor 100. The hexagonal distal end 158 of the inner adapter 154 is adapted to engage a complementary hexagonal opening 120 at the top of the locking cap 106.

Although specific interlocking relationships between the driver 150 and the bone anchor 100 are illustrated herein, the present inventors contemplate a variety of modifications. For example, the male-female relationship between the driver and the implant may be reversed, for either or both of the inner adaptor 154 and outer adapter 152. In addition, each of the inner adapter 154 and outer adapter 152 is provided with a surface structure for enabling rotational engagement with a corresponding component on the implant. Although this may be conveniently executed using corresponding hexagonal male and female components, any of a variety of alternative structures may be utilized in which a first surface on the inner adapter 154 or outer adapter 152 cooperates with a second, complementary surface on the corresponding aspect of the bone anchor 100, for allowing rotational engagement, followed by axial decoupling.

Figure 3:
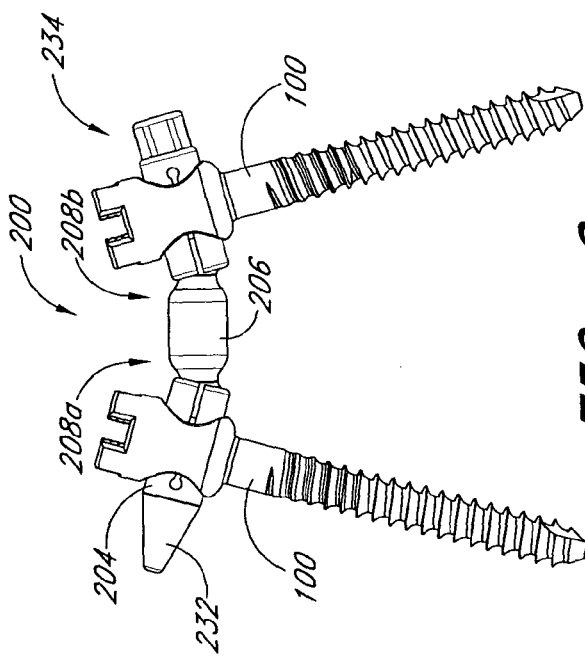
FIG. 3 is a side view of view of the system for minimally invasive posterior spinal fixation illustrated in FIG. 1, with the fixation rod detached from its insertion tool.
Figure 3A:
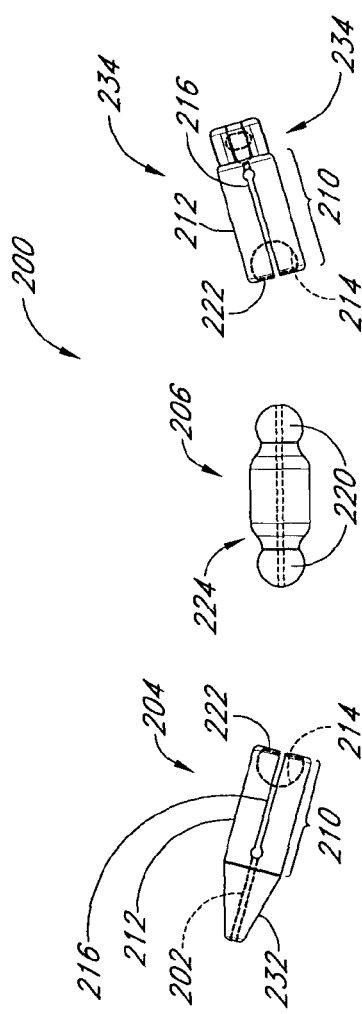
FIG. 3A is an unassembled side view of the fixation rod of FIG. 3.

With reference now to FIGS. 3 and 3A, the jointed fixation rod 200 will now be described in more detail. The fixation rod 200 preferably includes a first segment 204, a second segment 206 and a central lumen 202, which is configured to receive a guidewire as will be explained in more detail below. The first and second segments 204, 206 are coupled together by an angularly adjustable joint 208a.

As will be explained in more detail below, the fixation rod 200 may be provided with one or more joints 208a. The joints 208a provide the fixation rod 200 with a degree of flexibility that allows the fixation rod 200 to travel through a nonlinear, disjointed and/or curved path. This is particularly advantageous for inserting the fixation rod 200 through the transverse portals 116 of a plurality of bone anchors 100. For example, it is generally difficult to align the transverse portals 116 of a plurality of bone anchors 100 with each other because the surfaces of the spine are typically non-planar and non-uniform. As such, each bone anchor 100 may extend from the spine at a different angular orientation and/or height. It is particularly difficult to align the portals between an anchor positioned in the L5 vertebra and an anchor the S1 vertebra (i.e. sacrum).

It is therefore difficult to thread a straight or even curved fixation rod through the transverse portals 116 of more than one bone anchor 100. In a non-minimally invasive procedure, the surgeon may measure the degree of non-alignment between the bone anchors 100 and bend the fixation device and/or adjust the position of the bone anchor in the spine. However, in a minimally invasive procedure, such adjustments are impractical because they cause prolonged expose of the patient and the use to fluoroscopical radiation.

Although a particular configuration of an articulating joint will be described in detail below, any of a variety of structures may be utilized in implementing the present invention. In general, the implantable fixation rod will have at least a first segment and a second segment which are angularly adjustable with respect to each other while the rod is in a first state, and fixed with respect to each other when the rod is in a second state. This permits, for example, percutaneous introduction to a treatment site within a patient along a nonlinear path while the rod is in the first state. The rod may then be converted to the second state such that it exhibits a sufficient rigidity to produce the desired clinical result. This may be rigid fixation of a first bone or bone fragment with respect to a second bone or bone fragment.

The first and second segments will generally be separated by an interface, at which a first attachment or interface surface on a first segment is in contact with a second, complementary attachment or interface surface on the second segment. One implementation of this type of interface is a ball and socket type joint, described below. Another type of interface may be formed, for example, by a leaf spring type structure, or other axial element structures, such as two or more generally axially extending elements which are moveable with respect to each other to permit flexion but can be locked relative to each other such as by lateral compression.

The articulating joint can be transformed from the movable state to the fixed state in any of a variety of ways. One convenient manner of fixation is responsive to lateral compression which may be applied, for example by an axially movable component (e.g., a threaded shaft such as a set screw) carried by the bone anchor. Thus in a ball and socket type structure where a male component fits within a complementary female component, a surface on the outer female component may be flexed or compressed laterally inwardly against a complementary surface on the male component to provide fixation. Either or both complementary surfaces may be provided with friction enhancing surface structures such as ridges, roughening or micropitting, as will be appreciated by those of skill in the art in view of the disclosure herein.

With reference to FIGS. 3 and 3A, the joint 208a comprises a first surface 210 formed on the first segment 204 and a second complementary surface formed on the second segment 206. In the illustrated embodiment, the first surface comprises a socket or recess 214 and the second surface comprises a ball 220 so as to form of a ball joint between the adjacent ends of the first and second segments 204, 206. The first segment 204 includes a socket portion 210, which comprises a generally cylindrical outer surface 212 that is configured to extend within the transverse portal 116 of the bone anchor 100. The proximal end of the socket portion 210 includes the generally spherical socket or recess 214. At least one gap 216 is provided in the socket portion 210. In the illustrated embodiment, the at least one gap 216 extends from one side of the outer surface 212, through the central lumen 202 and to the opposite side of the outer surface 212 and therefore divides the socket portion 210 generally in half. Compression of the gap 216 reduces the cross-sectional diameter of the socket 214 and fixes the angular position of the joint 208a as will be explained in more detail below.

The socket portion 214 is configured to receive the ball 220 or spherical protrusion that is provided on the distal end of the second segment 206. In one embodiment, the ball 220 is configured such that it may be press-fitted into the socket 214. That is, the socket 214 defines an opening 222 that in a relaxed state is smaller than the maximum diameter of the ball 220. In this manner, as the ball 220 is inserted into the socket 214, the gap 216 expands to increase the diameter of the opening 222 and allow insertion of the ball 220 into the socket 218. Preferably, once in place, axial movement of the ball 220 with respect to the socket 214 is limited while at least limited angular adjustment of the ball 220 with respect to the socket 216 is permitted. This may be accomplished by providing the socket 216 with a slightly larger diameter than the ball 220 and/or configuring the joint 208a such that the friction between the ball 220 and the socket 214 permits angular adjustment. In this manner, the angular orientation between the first and second segments 204, 206 may be adjusted.

In the illustrated embodiment, the second segment 206 may be adjusted to any of a variety of angular orientations defined within a cone having a vertex v positioned generally at the center of the socket 214 and the ball 220. The angle a (see FIGS. 3B and 3C) represents the angular adjustment between the two segments and is defined primarily by the interference between the proximal end of the socket portion 204 and a neck 224 on the proximal end of the ball 220. This angle may be increased by decreasing the diameter of the neck 224. It should be appreciated that the maximum angle adjustment between the longitudinal axes b, c of the first and second segments is generally half of the angle a of the vertex.

Depending upon the environment of use, the angle a of the vertex is preferably within the range of about 15 to 90 degrees and the angle a between the longitudinal axis of the second segment 206 with respect to the first segment 204 may be rotated to any angle orientation within such cone. In one embodiment, the angle a of the vertex within the range of about 15 to 30 degrees for joints 208 positioned at the lumbar levels and within the range of about 45 to 90 degrees for joints 208 positioned at the L5 and S1 levels. In another embodiment, in the lumbar levels, the rod 200 may be fixed (e.g., formed without joints) while in the L5 and S1 levels the vertex of the joints 208 may be in the range of about 45 to 90 degrees.

One skilled in the art will understand that in other embodiments the illustrated ball joint may be replaced with any of a variety of other angularly adjustable structures such as hinges or other sliding structures that provide angular adjustment. For example, the shape of the socket and/or the ball may be modified in several different ways and still provide the angular adjustability described above. In one particular embodiment, the angular adjustability may be modified and/or limited. This may be accomplished by providing spherical exterior surface of the ball 220 with one or two or three or more surface structures such as projections or indentations. The indentations receive complementary surface structures such as projections provided within the socket 214 to limit the degree of rotation of the ball 220 within the socket 214 and/or the plane through which angular orientation may be adjusted. For example, in one embodiment, the first and second segments may be angularly adjusted only through one plane (e.g., a horizontal plane).

In the illustrated embodiment, the socket portion 210 is configured to fit within the transversal portal 116 within the head 108 (see FIGS. 2–2B) or through the aperture 110 in the connector 104 (see FIG. 2C). The portal 116 or aperture 104 is preferably provided with a complementary surface to the cylindrical exterior surface 212 of the socket portion. 210 As the socket portion 210 is inserted through the head 108, the angular orientation of the second segment 206 with respect to the first segment 204 may be adjusted as the ball 220 rotates with respect to the socket 214. The locking cap 106 may be threaded into the head 108 to lock the angular orientation between the first and second segments 204, 206, by acting against the outer surface of the socket portion 210 or the connector 105 and fixing the ball 220 within the socket 214. The bottom of the locking cap 106 may be provided with a concave surface (not shown) which is complementary to the spherical exterior surface 212 of the socket portion 210 or the connector.

In one embodiment, the threading of the locking cap 106 into the head 108 compresses the socket portion 210, decreasing the width of the gap 216 and reducing the cross sectional area of the socket 214. This secures the ball 220 within the socket 214 and fixes the angular orientation of the first segment 204 with respect to the second segment 206. In the embodiments which use a connector 104, the locking cap also fixes the angular position of the connector 104 within the head 108. In some embodiments, the socket 214 and/or the ball 220 may be roughened, etched (e.g., mechanical, electrical, photo, chemical etc.) and/or coated with material to increase the friction between these components. In this manner, the locking force between the socket 214 and the ball 220 may be enhanced. Such techniques may also be applied to the connector 104 and the outer surface of the first segment 204.

In the illustrated embodiment, the locking cap 106 also fixes the axial position of the socket portion 210 within the bone anchor 100. However, in modified embodiments this may be accomplished by a separate device (e.g., a set screw).

In general for lumbar applications, in the locked position, the fixation rod 200 will preferably exhibit a static compression within the range of from about 120 to about 200 lbs., and, more preferably greater than about 150 lbs and the rod will preferably exhibit a static torsion within the range of from about 15 to about 25 inch pounds, and, more preferably in excess of about 20 inch pounds. The rods will preferably reach at least about 5 million cycles, at 5 Hz. In general for cervical applications, in the locked position, the fixation rod 200 will preferably exhibit a static compression within the range of from about 30 to about 100 lbs., and, more preferably greater than about 80 lbs and the rod will preferably exhibit a static torsion within the range of from about 10 to about 20 inch pounds, and, more preferably in excess of about 15 inch pounds. The rods will preferably reach at least about 5 million cycles, at 5 Hz. Each of these parameters may be measured in accordance with the protocols described in the American Society for Testing and Materials (ASTM) designation F 1717-96, a copy of which is incorporated in its entirety herein by reference.

As mentioned above, the socket portion 210 and the corresponding gap 216 formed in the socket portion preferably have a length of approximately 10 to 30 millimeters. This provides the joint 208a with a working range in which the locking cap 106 can be used to fix the angular orientation of the joint 208a. That is, the locking cap 106 can be used to fix the angular orientation of the joint 208a as long as a least a portion of the socket portion 210 is positioned in the head 108 such that the locking cap 106 may compress the gap 216.

For a one level application, typically two bone anchors 100 are inserted into adjacent vertebrae. In such an application, the fixation rod 200 preferably includes two joints 208a, 208b. As shown, in FIG. 3A, the second joint 208b may be formed between a proximal end of the second segment 206 and a distal end of a third or end segment 230. In the illustrated embodiment, the proximal end of the second segment 206 includes a spherical protrusion or ball 220, which may be configured as described above. The end segment 230 includes a socket portion 210 configured as described above and including a socket 214 to receive the ball 220 of the second segment 206.

As can be seen FIG. 3, the first segment 204 of the linkage rod 200 may be provided with a tapered distal end 232. The tapered distal end 232 may be machined and be an integral part of the segment 204, may be molded integrally with the socket portion 210 or may be separately formed and attached to the linkage rod 200. In one implementation, the tapered end 232 may be a polymeric component such as nylon, HDPE, PEBAX or other materials known in the art. The tapered tip 232 facilitates advance of the linkage rod 200 through the transverse portal 116. In other embodiments, the distal end 232 may be blunt or ball shaped to minimize the protruding portion of the rod 200 from the portal 116 of the distal most anchor 100. In certain application, such embodiments advantageously reduce interference between the distal end of the rod 200 and the S1 body.

With continued reference to FIG. 3, the end segment 230 may include a hexagonal proximal end 234. The hexagonal proximal end 234 may be connected to the insertion tool as will be explained in more detail below.

The length of the linkage rod 200 in a device intended for use in a human adult one level lumbar or lumbar-sacral fusion, will generally be in the range from about 30 mm to about 90 mm and have a generally circular cross-section with an average diameter within the range of about 5.5 mm to about 9 mm. In such an embodiment, the first segment 204 and the end segment 230 will generally have a length within the range of from about 10 mm to about 40 mm. The gaps 216 will generally have width within the range of about 0.5 mm to 1.5 mm and a length within the range of from about 9 mm to about 29 mm. The socket portions 210 will generally have a length within the range of from about 10 mm to about 30 mm. The second segment 206 will generally have a length within the range of about 10 mm to about 10 mm. The socket 214 and the ball 220 may have a diameter within the range of about 5.0 mm to 7.0 mm.

In a two level application, three bone anchors 100 are typically inserted into adjacent vertebra. In such an application, the fixation rod 200' preferably includes four joints 208a, 208b, 208c, 208d. See FIGS. 4, 4A and 4B. As shown, in FIG. 4B, the four joints 208a–d may be provided by adding a fourth or intermediate segment 238 and an additional second segment 240, which is configured as described above. The immediate segment 240 may include two sockets 214 positioned at the distal and proximal ends of the segment 240 and a gap 216 that extends through the entire length of the segment 240. The outer surface 212 is configured to fit within a bone anchor (see FIG. 4A) such that tightening the locking cap 106 compresses both of the sockets 214 in the intermediate segment 238 and thereby fixes the corresponding joints 208b, 208c.

A linkage rod 200' in a two-level device intended for use in a human adult lumbar or lumbar-sacral fusion will generally have a length within the range of from about 70 mm to about 120 mm and a generally circular cross-section with an average diameter within the range of about 5.0 mm to about 9.0 mm. In such an embodiment, the first segment 204 and end segment 230 will generally have a length within the range of from about 10 mm to about 40 mm. The gaps will 216 will generally have a length within the range of from about 9 mm to about 29 mm and the socket portions 210 will generally have a length within the range of from about 10 mm to about 30 mm. The second and intermediate segments 206, 240 will generally have a length within the range of from about 10 mm to about 40 mm. The socket 214 and the ball 220 may have a diameter within the range of about 50 mm to 7.0 mm.

In another embodiment of the linkage rod 200 intended for two level fusion for use in the treatment of thoracic and cervical segments of the spine, the rod 200 has a length of about 100 mm to 240 mm and a generally circular cross-section with an average diameter of in the range of from about 3 mm to about 4 mm. In such an embodiment, the first segment 204 and end segment 230 will generally have a length within the range of from about 10 mm to about 40 mm. The gaps will 216 will generally have a length within the range of from about 9 mm to about 29 mm and the socket portions 216 will generally have a length within the range of from about 10 mm to about 30 mm. The second and intermediate segments 206, 240 will generally have a length within the range of from about 10 mm to about 40 mm. The socket 214 and the ball 220 may have a diameter within the range of about 5 mm to 7 mm.

Figure 4:
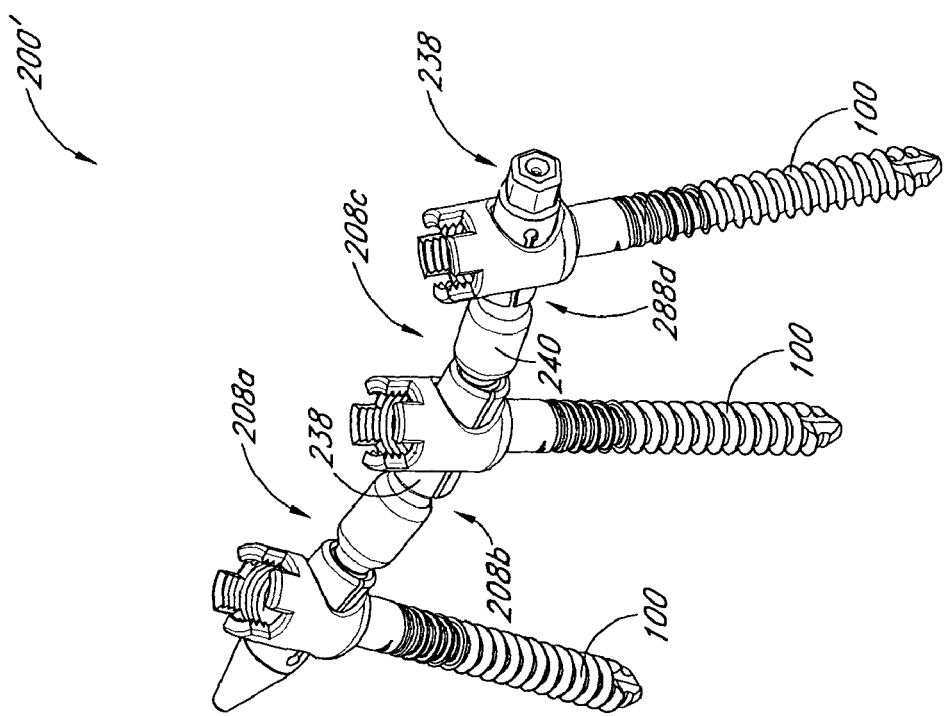
FIG. 4 is a side view of another embodiment of a system for minimally invasive posterior spinal fixation illustrated, with the fixation rod detached from its insertion tool.
Figure 4C:
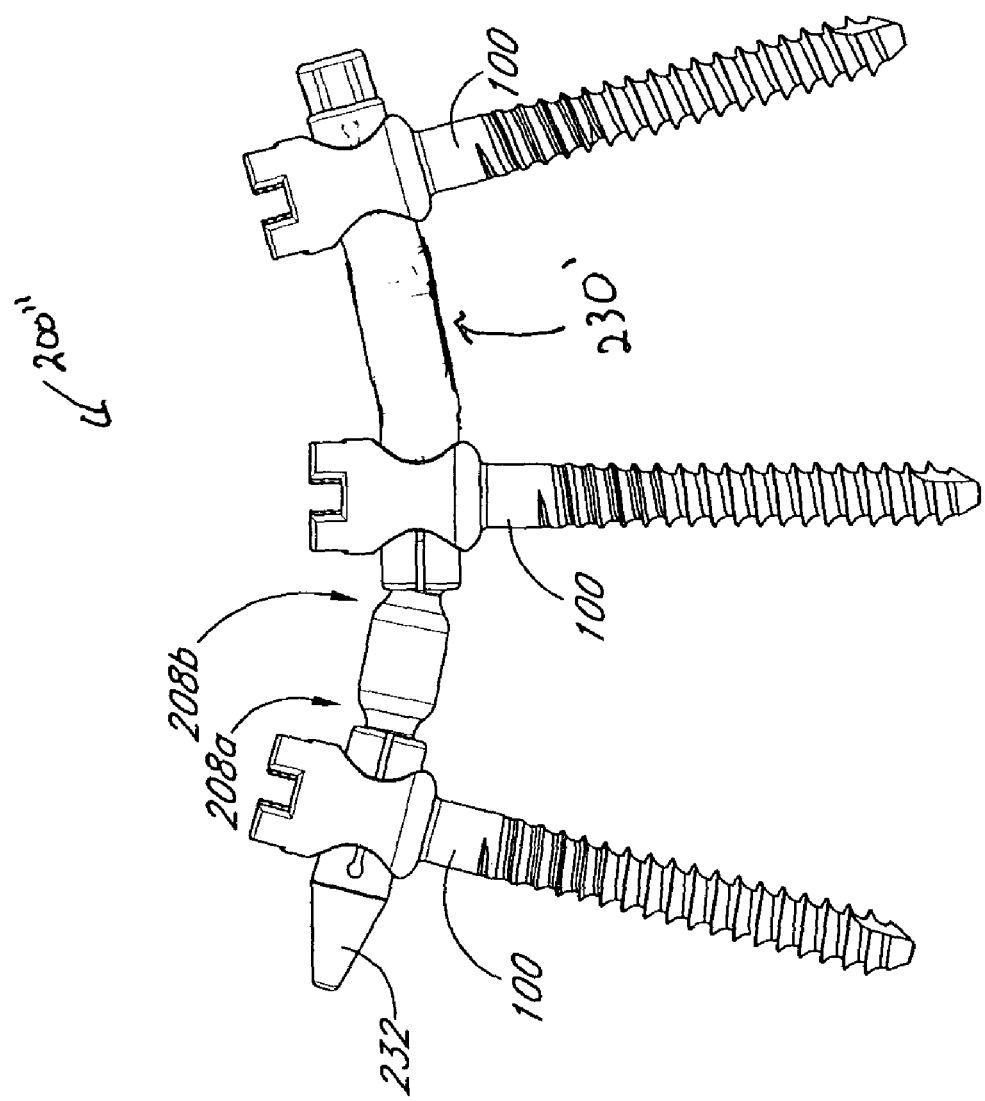
FIG. 4C is a side view of another embodiment of a system for minimally invasive posterior spinal fixation illustrated, with the fixation rod detached from its insertion tool.

FIG. 4C illustrates a modified embodiment of the fixation rod 200". This embodiment is particularly suited for a level two device for use in sacral-lumbar fusion. In this embodiment, the rod 200" includes at least one joint 208a, and preferably two joints 208a, 208b, between the distal and intermediate bone anchors 100 while the fixation rod 200" is fixed (i.e., formed without joints) between the intermediate and proximal anchors 100. As such, in this modified embodiment, the proximal or end portion 230' may be elongated as compared to the embodiment of FIG. 3 such that it can extend through the intermediate and proximal anchors 100. The end portion 230' may be substantially straight, partially curved or curved depending upon the clinical application. In this embodiment, the locking cap 106 in the proximal anchor 100 merely secures the rod 200" within the transverse portal 116.

In the embodiments described above, the cross sectional area of the rod 200, which may be expressed as a diameter in a circular cross sectional implementation, may be varied depending upon the desired structural integrity of the finished implant. The anchors 100 will have a diameter of in the range of from about 3.5 mm to about 4 mm and a length in the range from about 10 mm to about 55 mm.

In modified embodiments, the gaps 216 in the fixation rod 200 may be provided with a compressible material which compresses when the locking cap 106 tightens the cylindrical portion within the head 108. Compressible material, including any of a variety of compressible polymeric materials known in the medical device arts can be used according to several embodiments of the present invention. One skilled in the art will appreciate that other suitable flexible or compressible materials may also be used. In addition, any of a variety of metal (stainless steel, titanium, etc.) connectors may be configured such that the socket 214 is moveable from a first, large cross-section, for allowing movement of the ball 220 therethrough, to a second, reduced cross section for locking the angular position of the ball 220. This may be accomplished by providing opposing in the socket portion 210 any of a variety of interlocking structures such as ramp and pawl ratchet structures, or sliding fit structures which permit a reduction in the diameter in the socket 214 under compressive force from the locking cap 106.

In a modified embodiment, portions or all of the socket portion 210 comprise a compressible media such as an open cell foam, closed cell foam or solid compressible material. Structures comprising polyethylene, PEEK, nylon, and other polymers known in the medical arts may be utilized, depending upon the construction and desired compressibility. In general, the combination of material and the structure of the socket 214 is sufficient to allow angular adjustment of the longitudinal axis of ball 220 and the socket 214 to provide the linkage rod 200 with an angularly adjustable joint 208. After the socket portion 210 has been positioned within the transverse portal 116, rotational and/or axial movement of a locking element such as locking cap 106 functions to both prevent axial movement of the linkage rod 200 within the aperture 116, as well as prevent further angular adjustment of the joint 208.

In one embodiment, the sockets 214 have a tendency to return to their original diameters even after the cylindrical portions 210, respectively, are compressed by the locking cap 106 within the head 108. This tendency results from the resiliency of the metal, alloy or other material used to make the cylindrical. The use of compressible material, such as V-shaped channels in the gaps 216, reduces or eliminates this tendency and may allow a linkage rod 200 and the joint 208 to be more firmly secured. One skilled in the art will understand that the sockets 214 can be made from lower resiliency materials which can also reduce or eliminate the tendency of sockets 214 to return to their original diameters.

Figure 5:
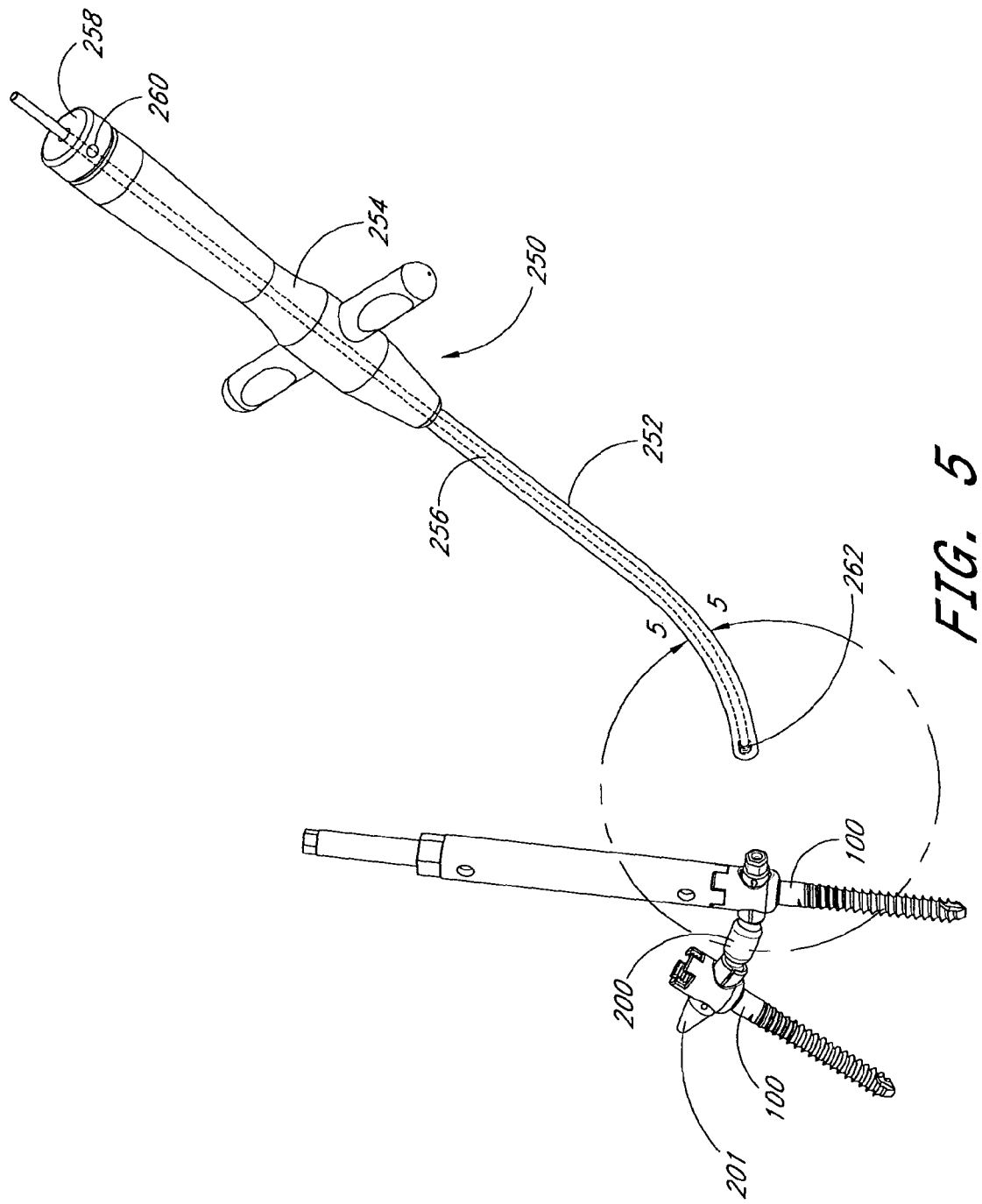
FIG. 5 is another view of the system for minimally invasive posterior spinal fixation illustrated in FIG. 1, with the linkage rod detached from its insertion tool.

In FIG. 5, the linkage rod 200 is shown positioned within two adjacent bone anchors 100, and released from the insertion tool 250. The insertion tool 250 is provided for the insertion of the linkage rod 200 into the bone anchors 100. The insertion tool 250 comprises an arm 252 and a handle 254. In the illustrated embodiment, the arm 252 is curved to facilitate insertion of the linkage rod 200 into the bone anchors 100 within a patient along a curved tissue tract which passes through the aperture 110 of at least each of a first bone anchor and a second bone anchor. However, it should be appreciated that in modified embodiments, the arm 252 may be of a different shape (e.g., straight) and be inserted through a tract of a different shape.

A central control line 256 (shown mostly in phantom) such as a torque transmission tube, rod or cable extends through an axial lumen of the insertion tool 250, and terminates at a control such as a knob 258 at the proximal end of the insertion tool 250. A screw (not shown) threaded into a tunnel 260 extending along a radius of the knob 258 may be used to secure the control line 256 within the knob 258. The control line 256 is provided with a threaded distal tip 262. Rotating the knob 258 thus rotates the control line 256 and its threaded distal tip 262 to engage or disengage the linkage rod 200.

In one embodiment, both the linkage rod 200 and the control line 256 are provided with a central axial lumen for the passage over a guide wire.

Figure 5A:
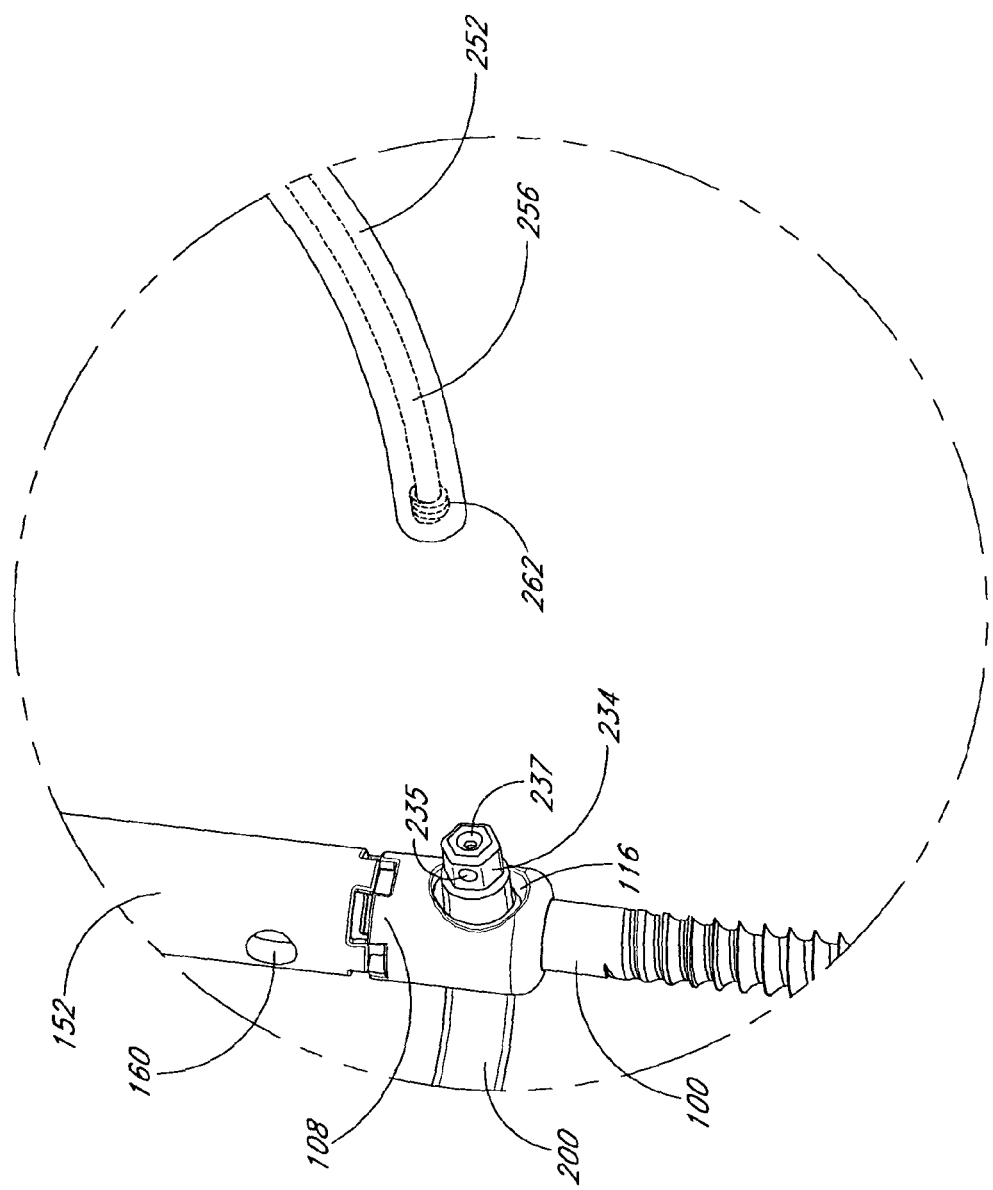
FIG. 5A is an enlarged view of the circled area in FIG. 4.

FIG. 5A is an enlarged view of the circled area in FIG. 5, showing the distal end of the outer adapter 152, the bone anchor 100, the linkage rod 200, and the distal end of the arm 252 of the insertion tool. The linkage rod 200 is shown fixed within the head 108 of the bone anchor 100.

As mentioned above, linkage rod 200 is provided with a hexagonal proximal end 234 adapted to engage a complementary hexagonal socket (not shown) in the distal end of the arm 252 of the insertion tool. In some embodiments, alternative complementary surface structures may be provided on the linkage rod 200 and the arm 252 to rotationally fix their orientation with respect to one another. In the illustrated embodiment, the hexagonal proximal end 234 is provided with a dimple 235 adapted to engage a complementary nub (not shown) within the hexagonal socket (not shown) in the distal end of the arm 252 of the insertion tool. The dimple 235 and nub (not shown) fix the axial orientation of the linkage rod 200 with respect to the arm 252. The threaded distal tip 262 of the control line 256 may be threaded into a complementary threaded hole 237 in the hexagonal proximal end 234 of the linkage rod 200, enabling the linkage rod 200 to be detachably secured to the arm 252 of the insertion tool. The threaded distal tip 262 may be threaded into the threaded hole 206 by rotating the knob (not shown) at the proximal end of the insertion tool. Unthreading the threaded distal tip 262 from the threaded hole 206 allows the linkage rod 200 to be released from the insertion tool 250.

With continued reference to FIG. 5A, in the illustrated embodiment, the outer adapter 152 is provided with an opening 160 extending along a diameter for fluoroscopic or other visualization of the rotational orientation of the outer adapter 152, to align the portal 116 of the bone anchor 100 engaged by the outer adapter 152. Towards this end, the axis of the opening 160 is preferably arranged at a right angle to the axis of the portal 116 as shown in FIG. 5A. To visualize the axial position of the outer adapter 152 and the bone anchor 100, the inner adapter 154 may be temporarily retracted so that it does not block the opening 160. In another embodiment a translucent marker may be installed in opening 160 for fluoroscopic or other visualization of the outer adapter 152.

Alternatively, any of a variety of other indicium of the rotational orientation of the bone anchor 100 may be provided. For example, the complementary surface structures between the proximal end of the bone anchor 100 and the distal end of the insertion tool 250 may be configured to only allow coupling between the two components in a predetermined rotational orientation. In this construction, visual indicia may be provided on a portion of the insertion tool 250 (e.g. "T" handle, painted or etched markings or other indicium) which remains external to the patient, to allow direct visual observation of the rotational orientation of the longitudinal axis of the transverse portal 116.

Figure 6:
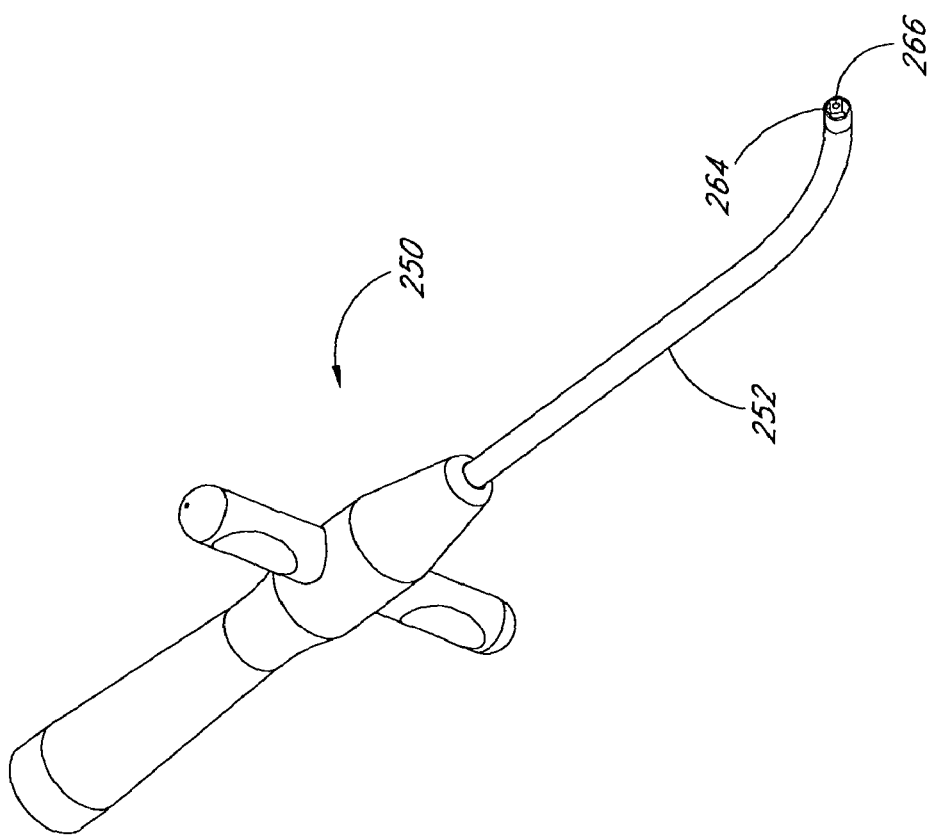
FIG. 6 is another view of the insertion tool of the system for minimally invasive posterior spinal fixation illustrated in FIG. 1.

FIG. 6 illustrates the described insertion tool from another angle. The knob and its attached central cable have been removed for clarity. The hexagonal socket 264 adapted to engage the hexagonal proximal end (not shown) of the linkage rod, as described above, is shown. The nub 266 adapted to engage the dimple (not shown) on the hexagonal proximal end (not shown) of the linkage rod is also shown.

In several embodiments, the components of the bone anchor, the linkage rod, the driver, and the arm of the insertion tool may be made of titanium, stainless steel or any other suitable metals, alloys, or material. The handle of the insertion tool is preferably made of a suitable non-slip material. The selection of these materials for the manufacture of the components and devices described in the above embodiments would be known by those skilled in the art.

Methods for the minimally invasive implantation of posterior fixation hardware according to embodiments of the present invention are disclosed in the context of a spinal fixation procedure with reference to FIGS. 7–47. Additional details concerning the method are disclosed in the copending patent applications incorporated by reference previously herein. Although the methods and instruments of the present invention can be utilized in an open surgical procedure, the present invention is optimized in the context of a percutaneous or minimally invasive approach. Thus, the method steps which follow and those disclosed in the copending patent applications incorporated by reference herein are intended for use in a trans tissue approach. However, to simplify the illustrations, the soft tissue adjacent the treatment site is not illustrated in the drawings discussed below.

Figure 7:
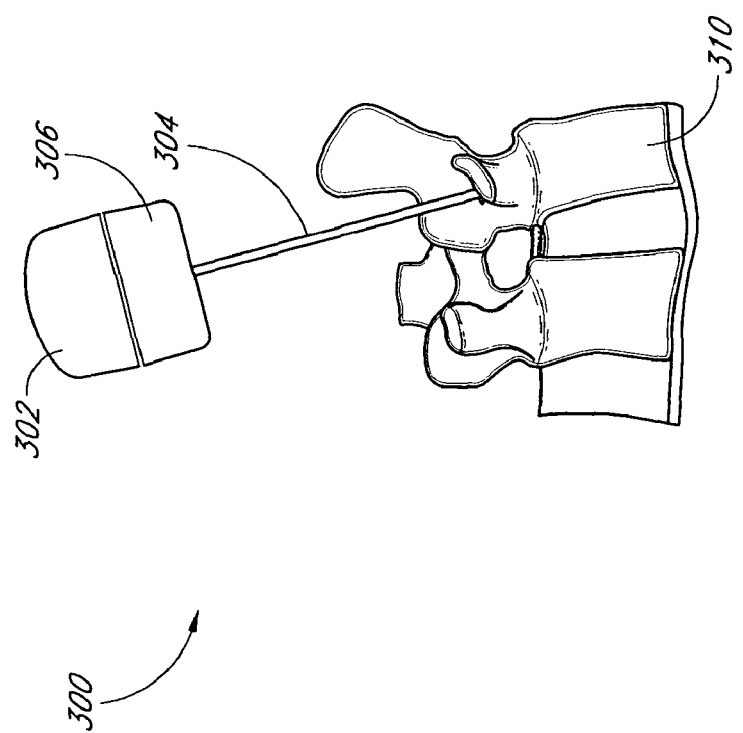
FIGS. 7–12 illustrate the use of positioning tools to position a guide wire into a vertebral body.
Figure 8:
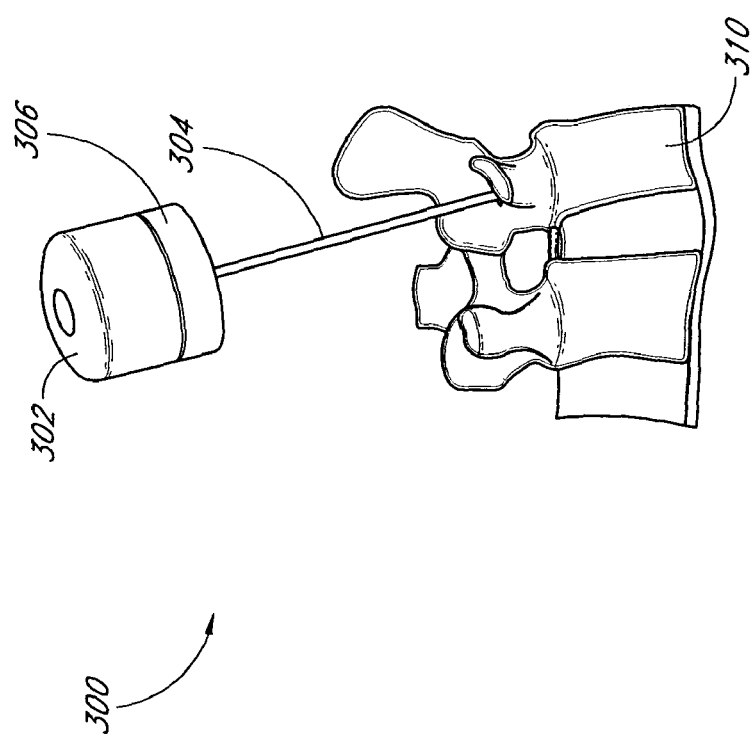

In FIGS. 7 and 8, a trocar 300 is inserted through a tissue tract and into a vertebral body 310. The trocar 300 comprises a sharp-tipped rod 308 (shown in FIG. 16) attached to a proximal or top half-handle 302. The sharp-tipped rod 308 is arranged concentrically within a cannula 304, which is attached to the bottom half-handle 306 of the trocar 300. The top half-handle 302 and the bottom half-handle 306 of the trocar 300 are screwed together for initial use, as shown in FIGS. 7–8. The trocar 300 is inserted through the skin, muscle and other tissues of the patient into the vertebral body 310.

Figure 9:
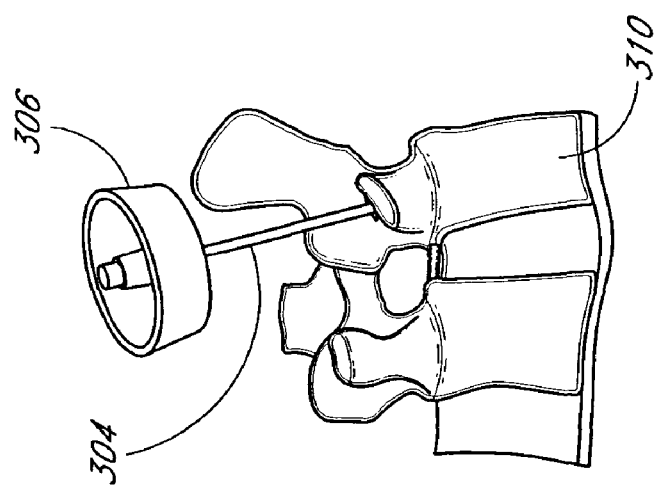
Figure 10:
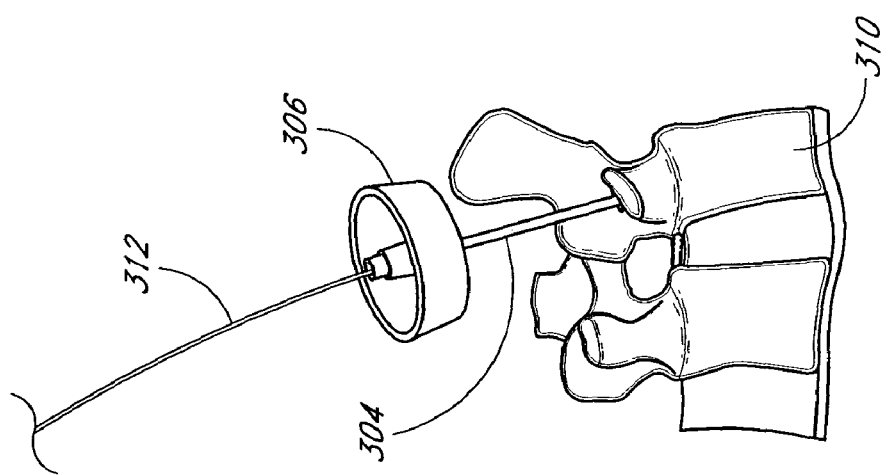

FIG. 9 shows the bottom half-handle 306 with the attached cannula 304 embedded in the vertebral body 310. The top half-handle (not shown) has been unscrewed and set aside from the bottom half-handle 306. In FIG. 10, a guide wire 312 is inserted into the vertebral body 310 via the bottom half-handle 306 and the cannula 304.

Figure 11:
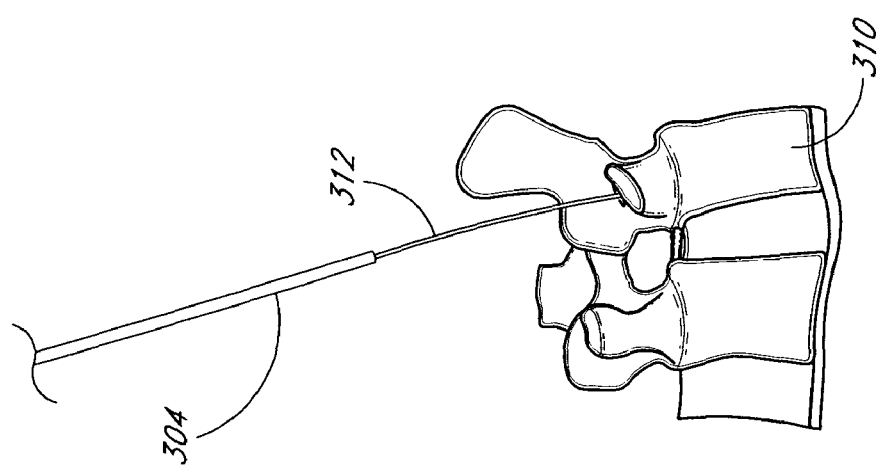

In FIG. 11, the bottom half-handle 306 and the cannula 304 are removed from the vertebral body 310. Preferably, the guide wire 312 remains in place in the vertebral body 310.

Figure 12:
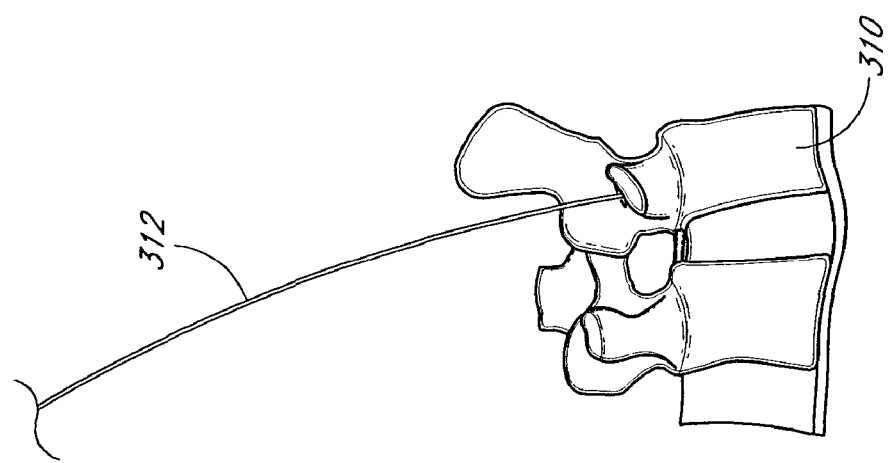

FIG. 12 shows the guide wire 312 in the vertebral body 310 after the bottom half-handle 306 and the cannula 304 are removed.

Figure 13:
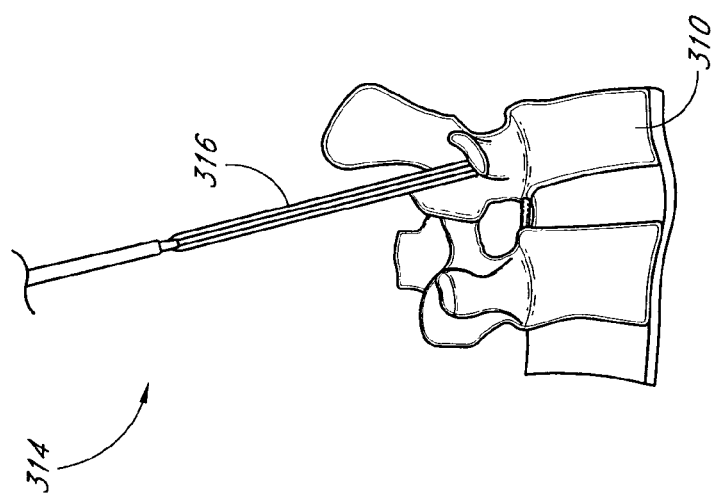
FIGS. 13–14 illustrate the use of a dilation balloon catheter to dilate a tissue tract.
Figure 14:
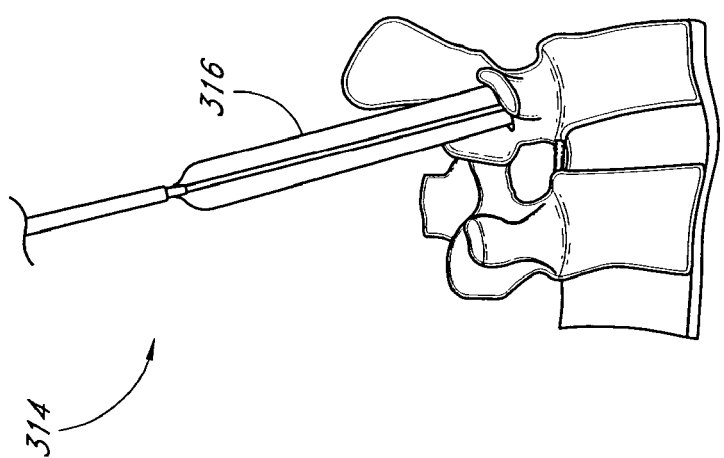

FIGS. 13–14 show one embodiment of use in which an inflatable tissue expander for enlarging the tissue tract is used. In FIG. 13, a balloon catheter 314 carrying a balloon 316 is advanced over the guide wire 312 towards the vertebral body 310. In FIG. 14, the balloon 316 is inflated to dilate the tissues adjacent the access pathway to the vertebral body 310. This provides an enlarged path for the insertion of a sheath as described below.

Figure 15:
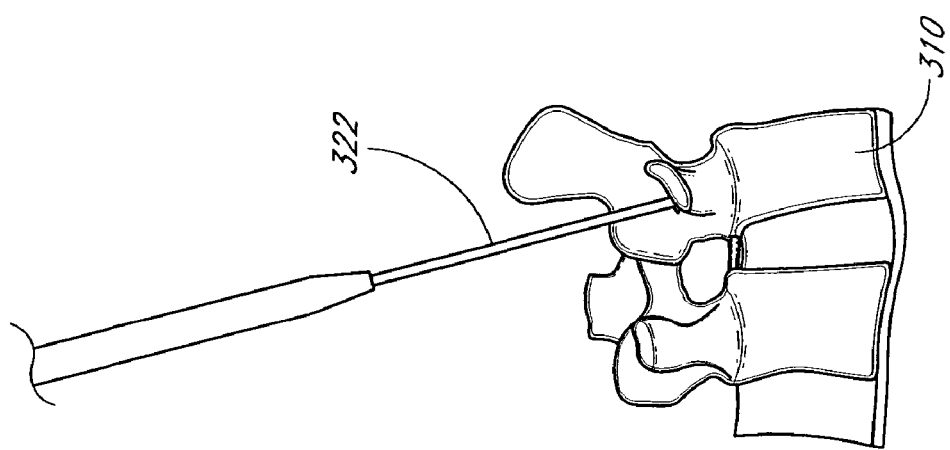
FIGS. 15–20 illustrate the positioning of a sheath adjacent to a vertebral body.
Figure 16:
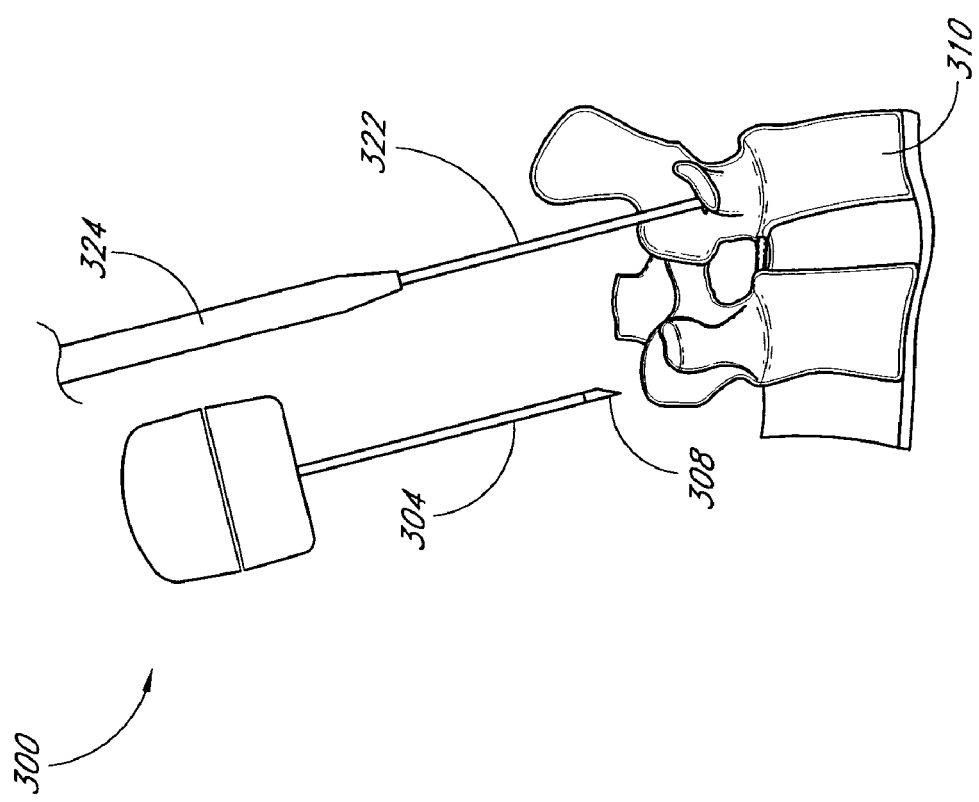

In FIG. 15, a guide tube 322 is advanced over the guide wire 312 into the vertebral body 310. As shown in FIG. 16, in one embodiment, the guide tube 322 may be approximately the same diameter as the cannula 304 of the trocar 300, allowing the guide tube 322 to be inserted into the opening in the vertebral body 310 created earlier by the trocar 300. The guide tube 322 acts as a stable rail over which a tapered dilation cylinder 324 may be advanced against the vertebral body 310.

Figure 17:
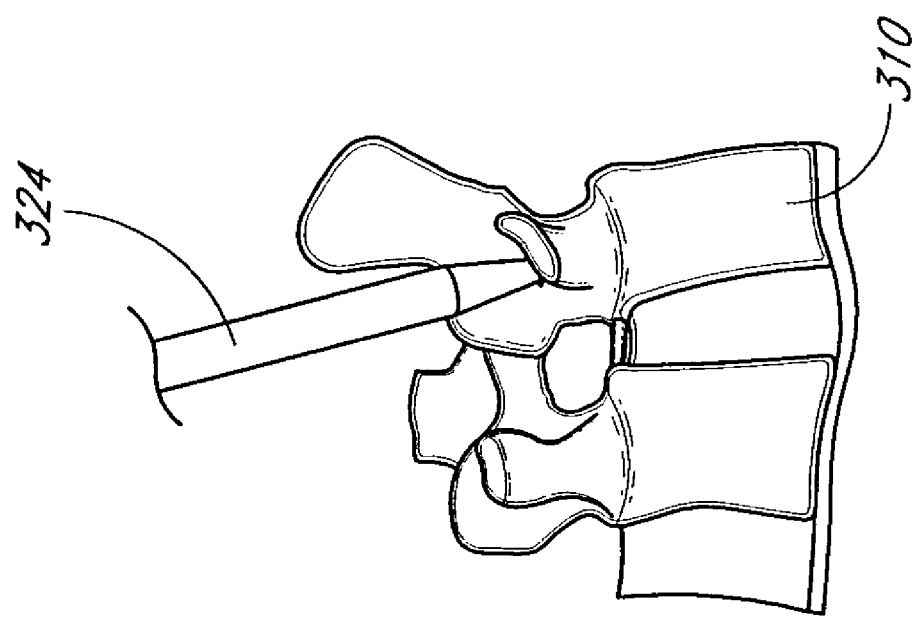

In FIGS. 16–17, a tapered dilation cylinder 324 is advanced over the guide tube 322 against the vertebral body 310. In one embodiment, the tapered dilation cylinder 324 may be approximately the same diameter as the inflated dilation balloon 316 discussed above with reference to FIGS. 13–14. The tapered dilation cylinder 324 is used to occupy the path created by the dilation balloon, and facilitates the insertion of a sheath. In an alternate sequence, the dilation cylinder 324 is provided without a tapered distal end, and is distally advanced into position directly over the inflatable balloon.

Figure 18:
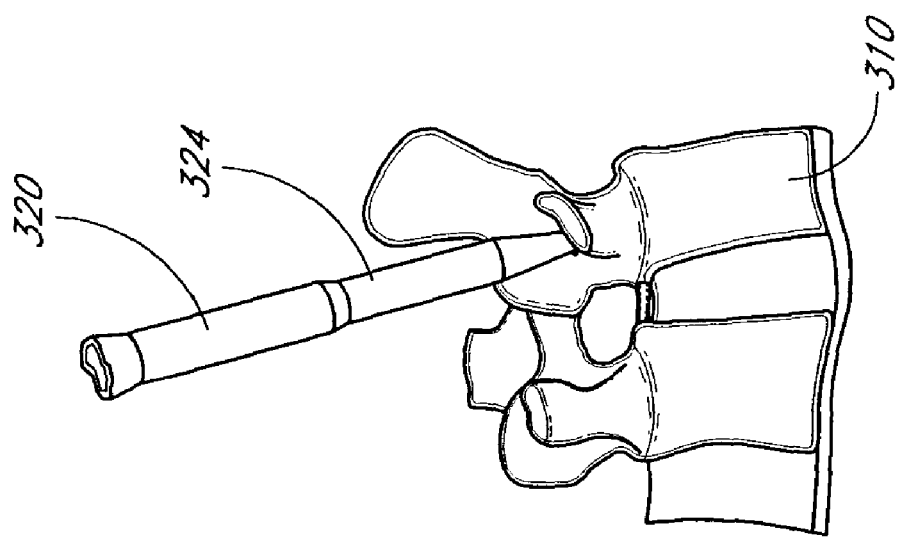
Figure 19:
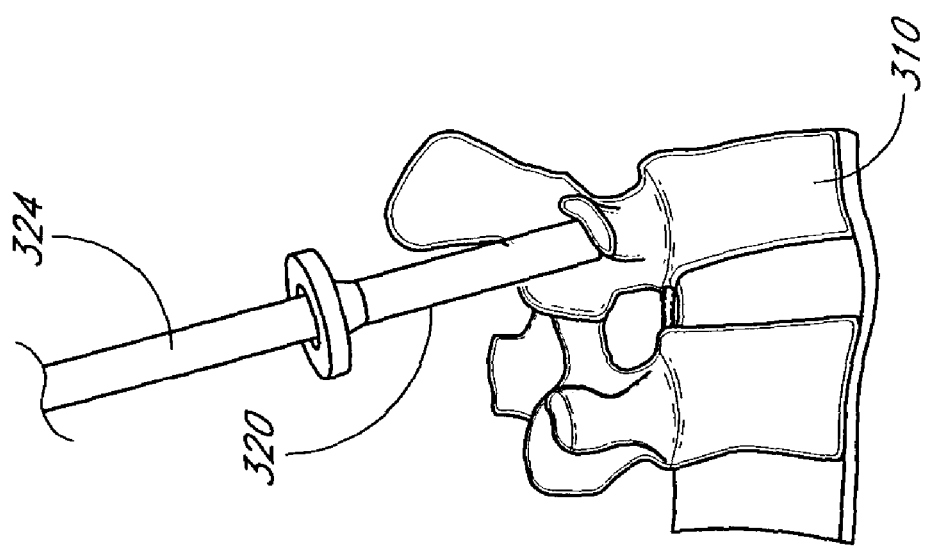
Figure 20:
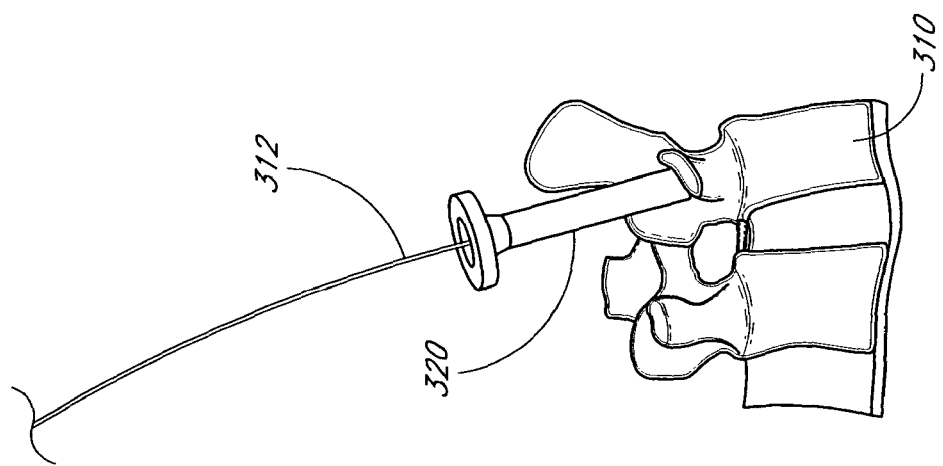

In FIGS. 18–20, a sheath 320 is advanced over the tapered dilation cylinder 324 against the vertebral body 310. The sheath 320 occupies the path created by the dilation balloon. Afterwards, the guide tube 322 and the tapered dilation cylinder 324 are removed. As shown in FIG. 20, the guide wire 312 preferably remains in the vertebral body 310 after the placement of the sheath 320.

Figure 21:
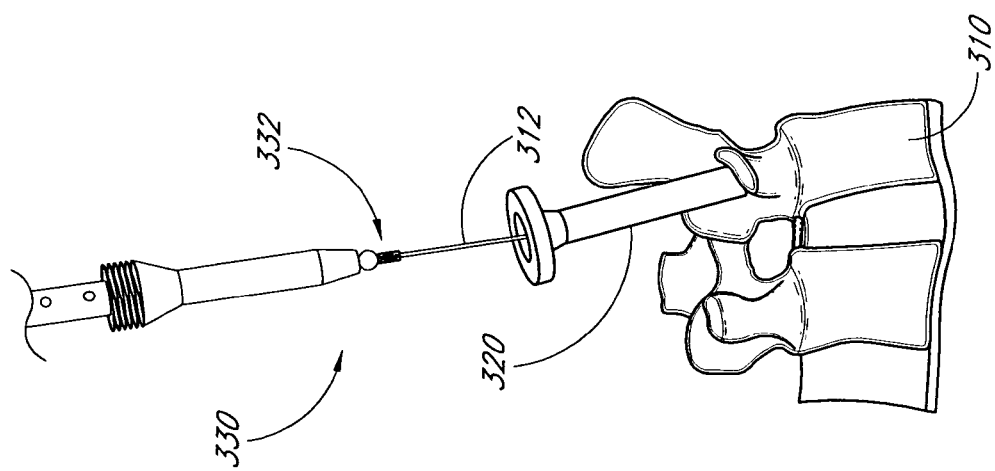
FIGS. 21–23 illustrate a drill used to create an opening in a vertebral body to receive a bone anchor.
Figure 22:
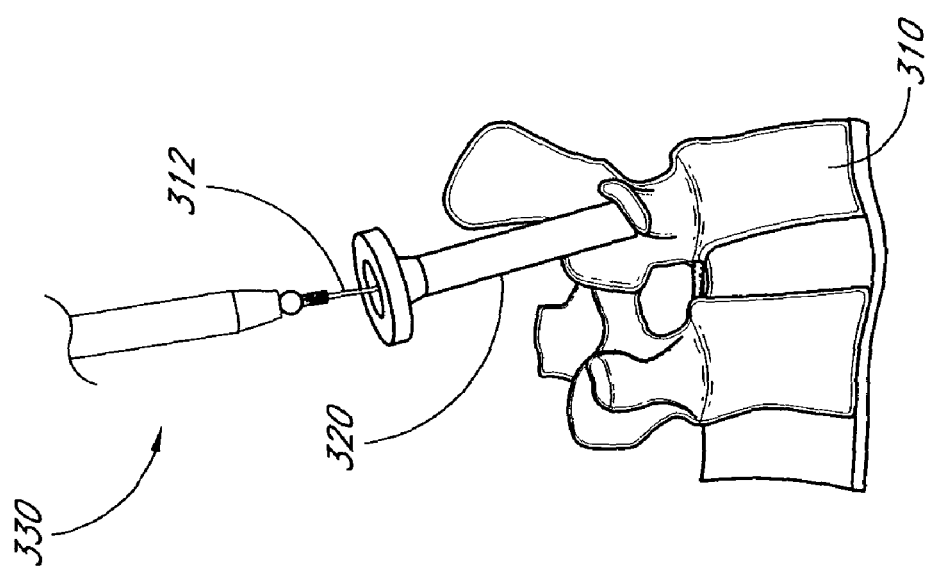
Figure 23:
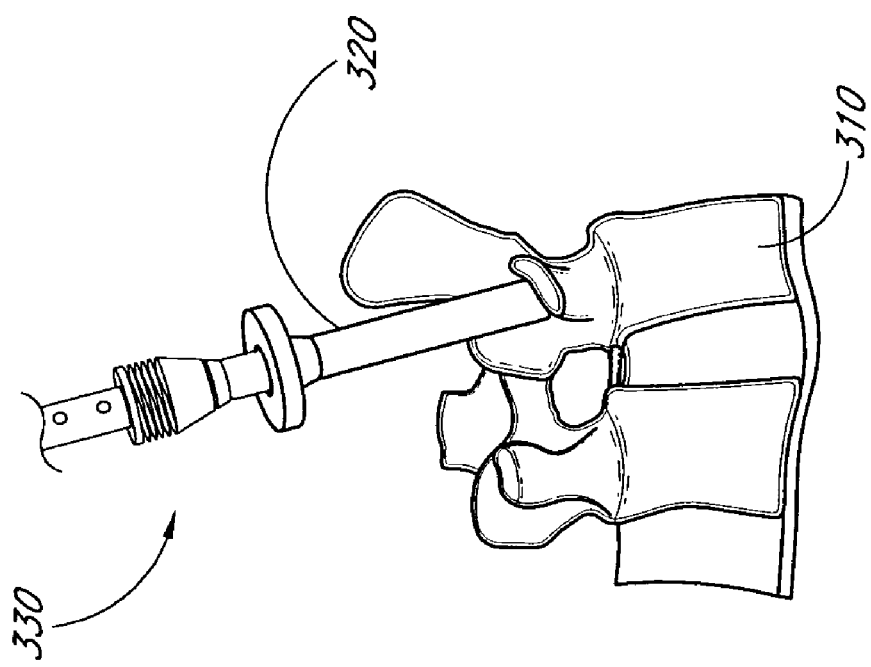
Figure 24:
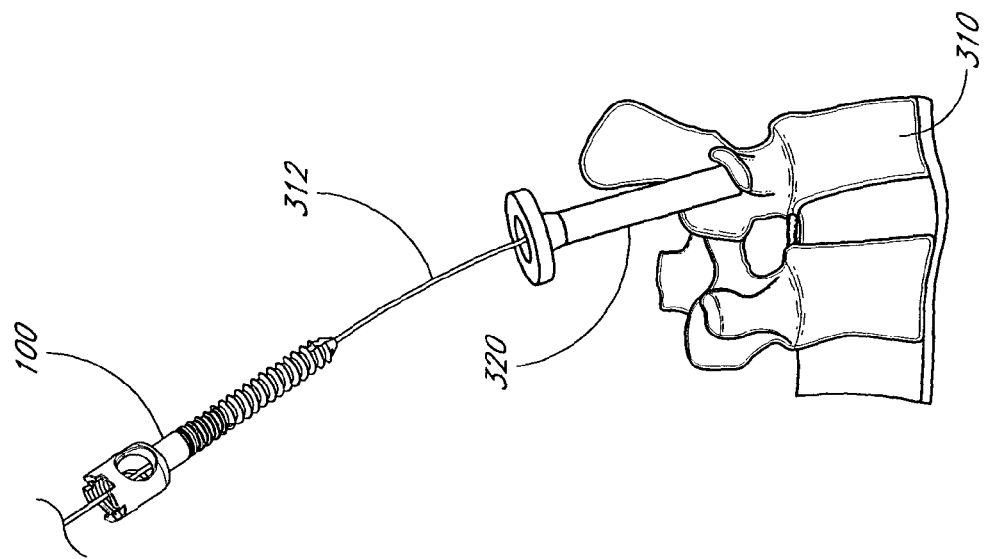
FIGS. 24–25 illustrate advancing a bone anchor over the wire towards a vertebral body.
Figure 25:
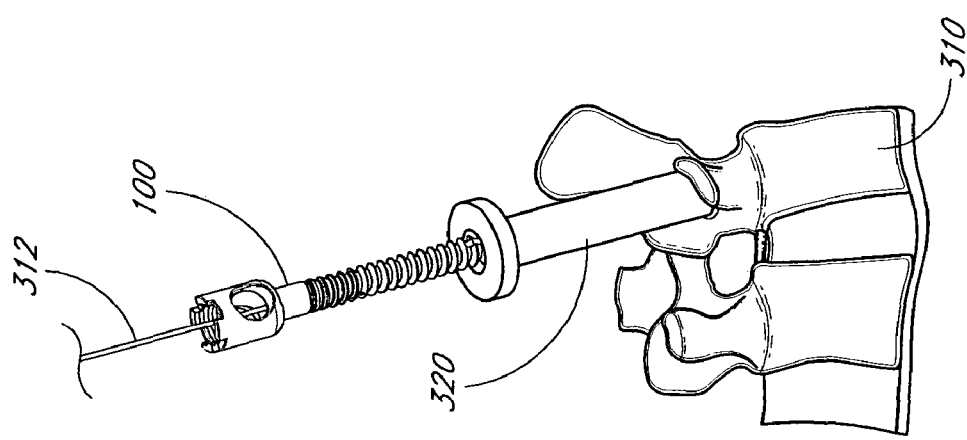

In FIGS. 21–23, a drill 330 having a rotatable distal tip 332 is advanced over the guide wire 312 and through the sheath 320. The drill 330 drills an opening (not shown) in the vertebral body 310 adapted for the insertion of a bone anchor 100. Afterwards, the drill 330 is removed. In FIGS. 24–25, the bone anchor 100 is advanced over the guide wire 312 and through the sheath 320 towards the vertebral body 310.

In FIGS. 24 and 25, a bone anchor 100 is advanced over the wire 312 and through the sheath 320 into engagement with the vertebral body 310. Although the insertion tool 250 is not illustrated, the bone anchor 100 may be coupled to the insertion tool 250 prior to the step of advancing the bone anchor 100 into contact with the vertebral body 310.

Figure 26:
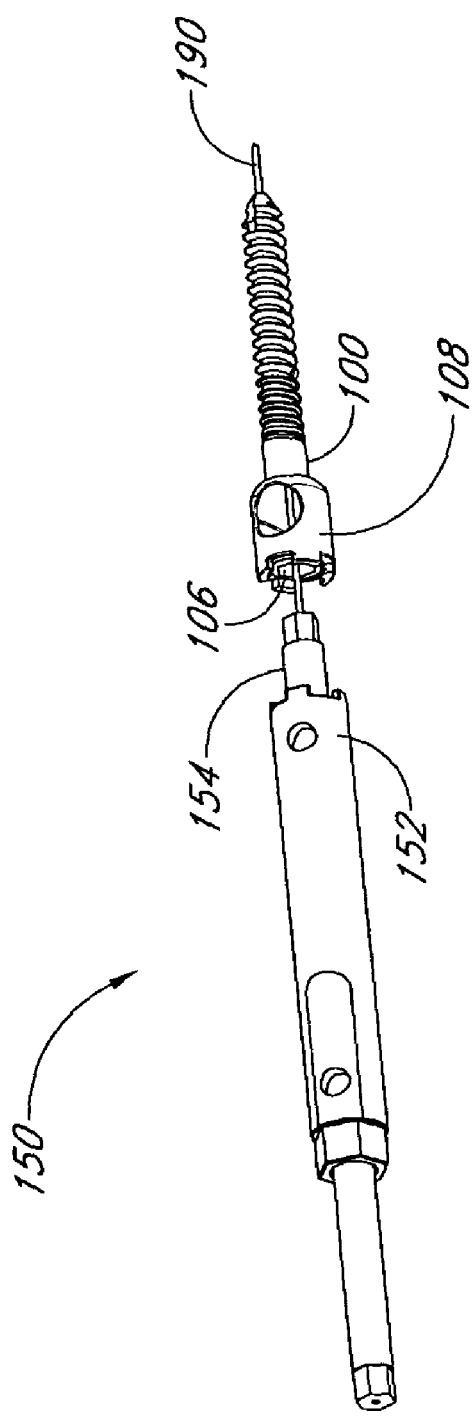
FIGS. 26–27 illustrate a bone anchor and the driver used to insert the bone anchor into a vertebral body.
Figure 27:
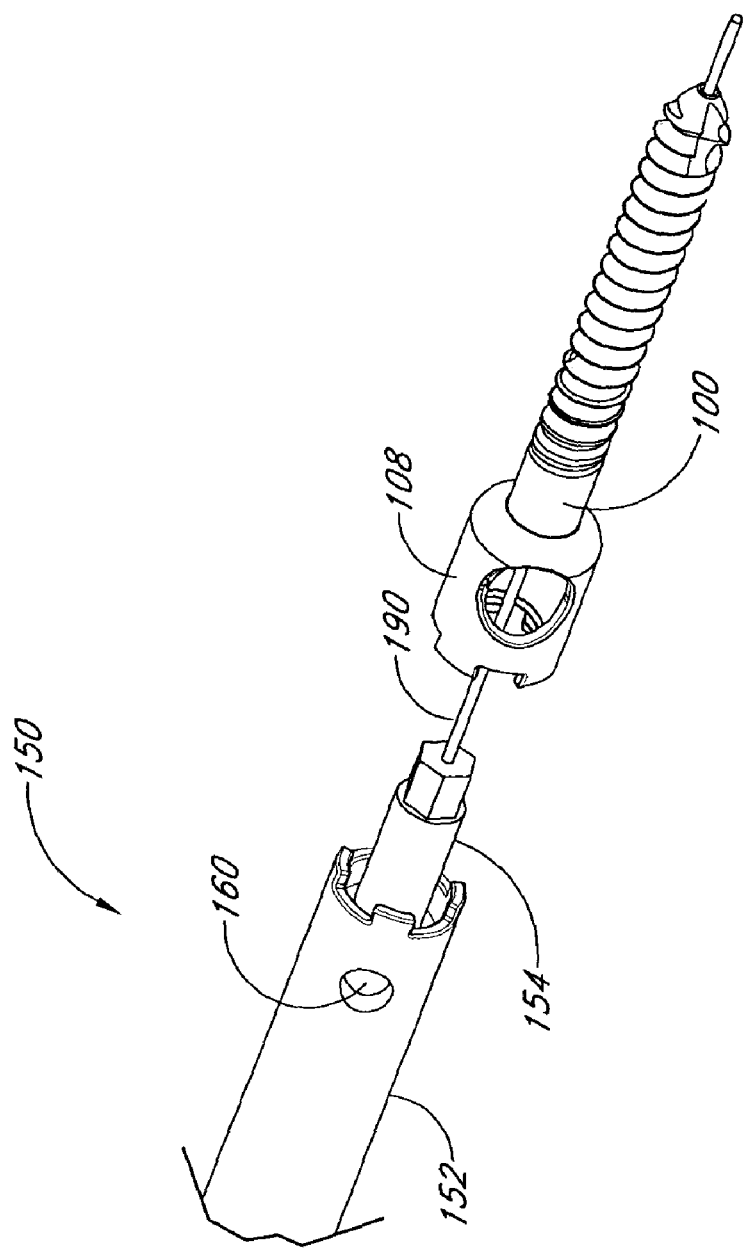
Figure 28:
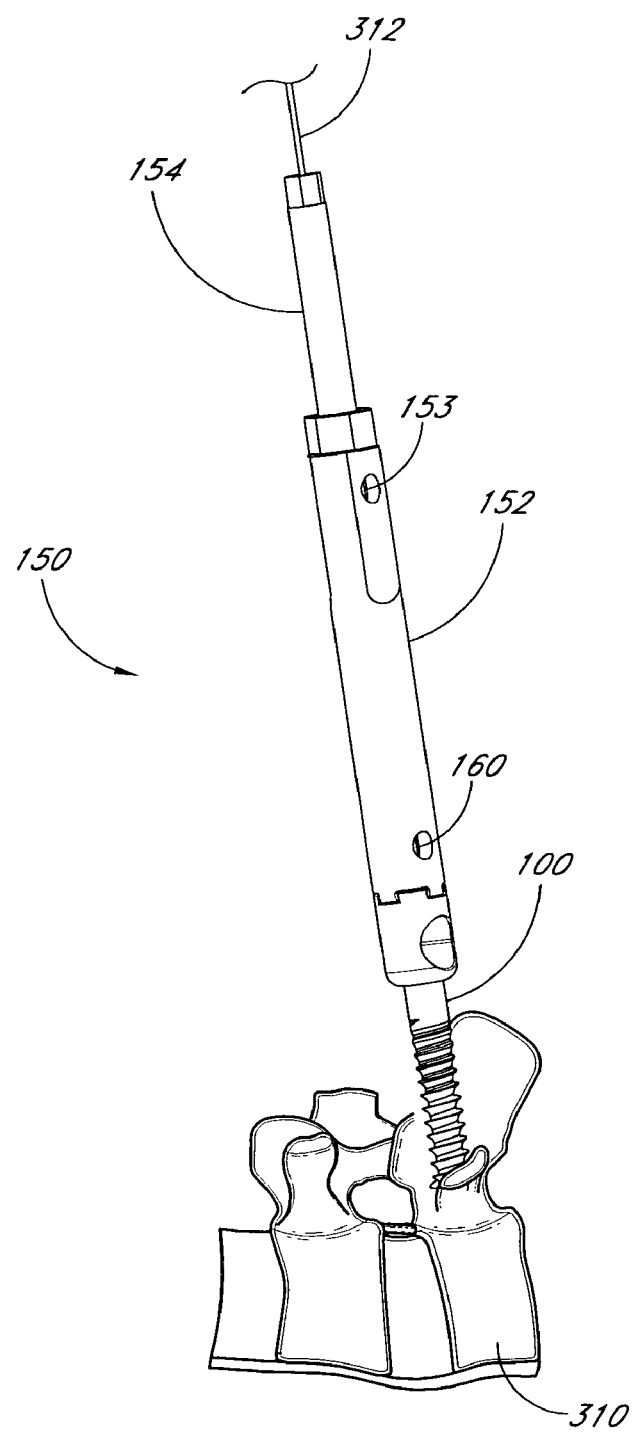
FIGS. 28–31 illustrate the use of the driver to insert a bone anchor into a vertebral body.

FIGS. 26 and 27 show the outer adapter 152 and the inner adapter 154 of the driver 150, as well as a bone anchor 100, with the the locking cap 106 disposed within the head 108 of the bone anchor 100. The interrelation of these components have been described in detail above with reference to FIGS. 2 and 2A. The outer adapter 152 illustrated in FIGS. 26–28 additionally comprises a pivot hole 153 which extend through a diameter of the outer adapter 152. The pivot hole 153 is adapted for the attachment of a guide wire insertion device 400 described in further detail below. In FIG. 28, these components are shown arranged over a guide wire 190.

Figure 29:
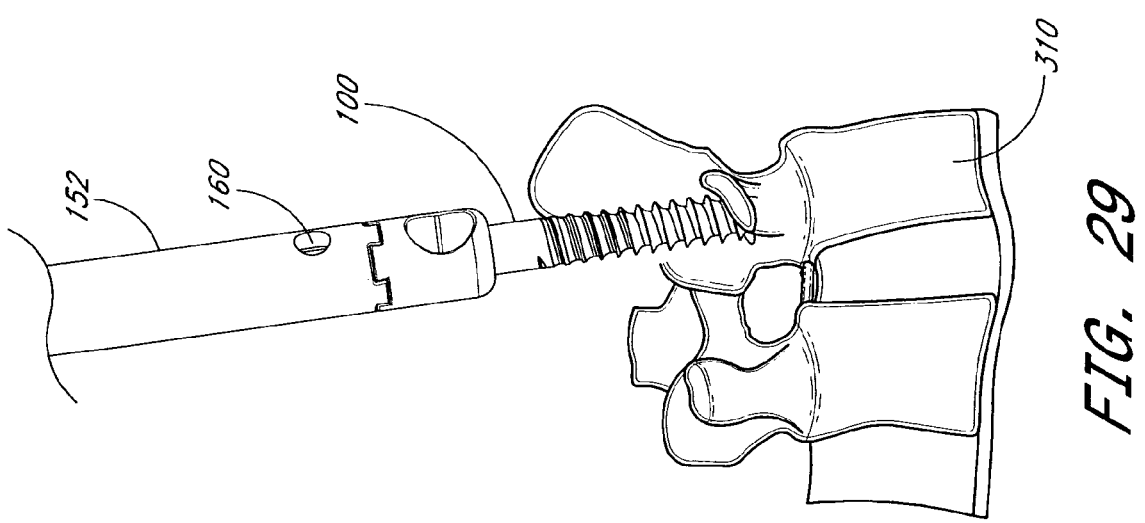
Figure 30:
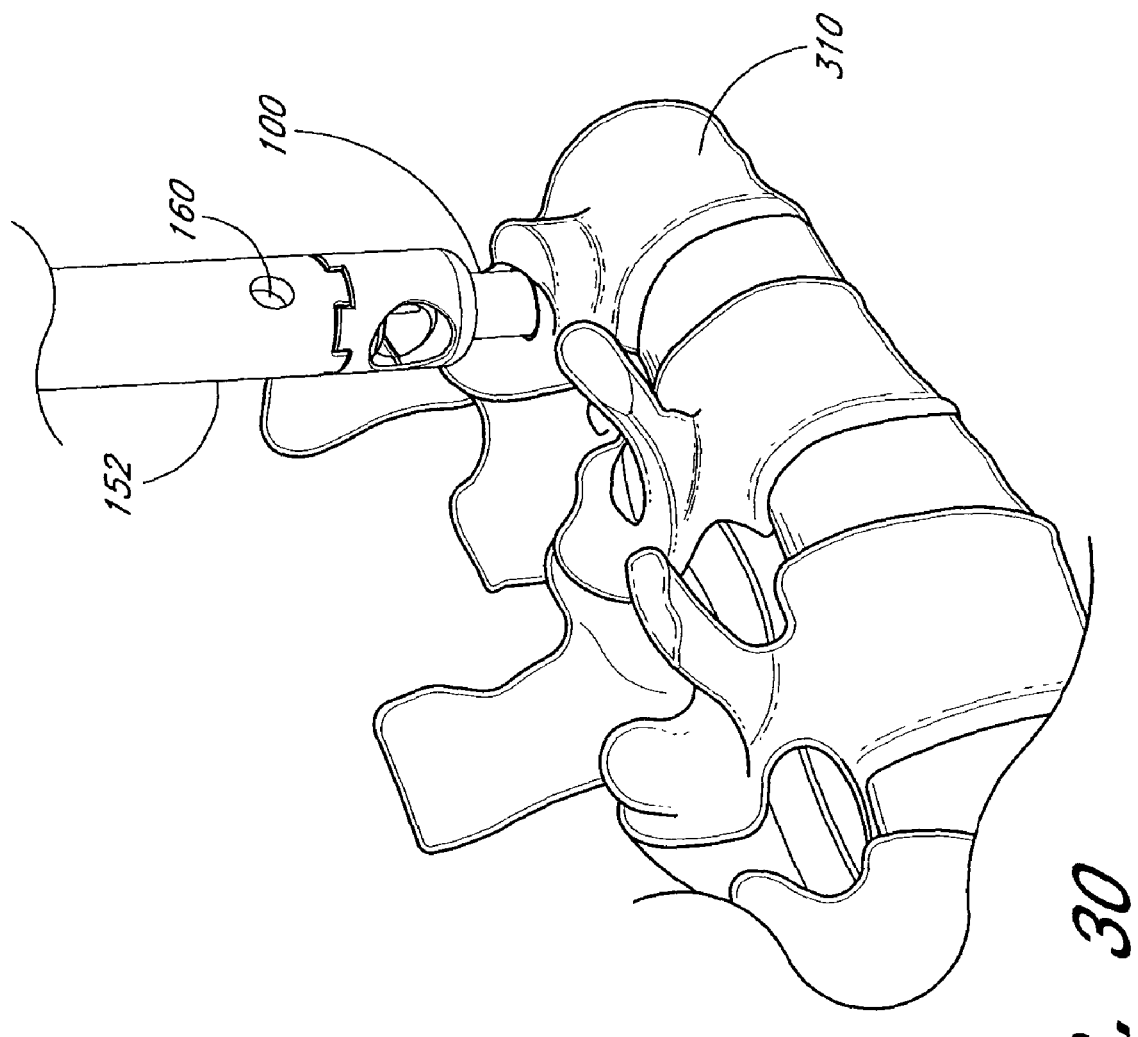
Figure 31:
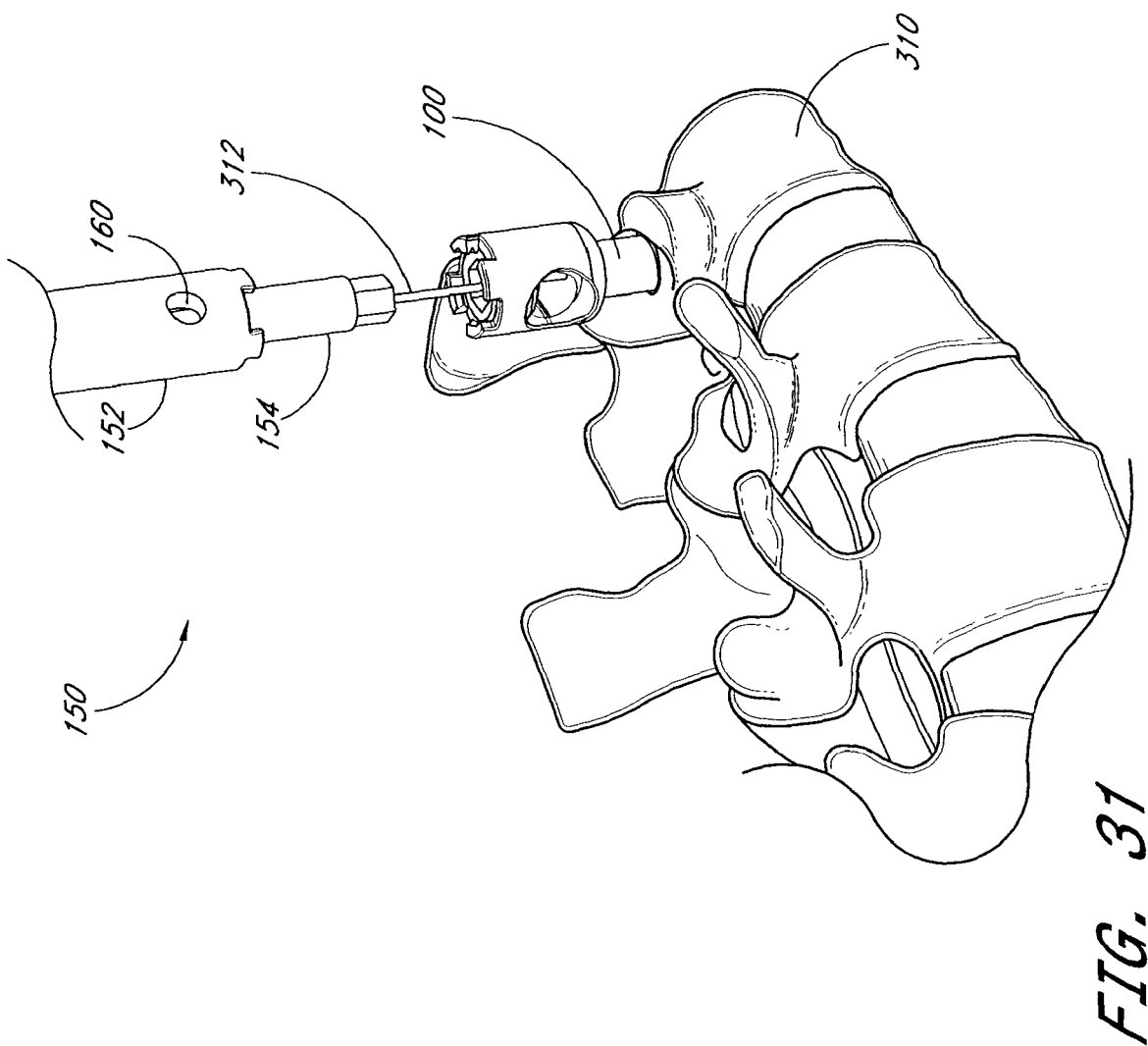

In FIG. 28, the driver 150 (comprising the outer adapter 152 and the inner adapter 154 ) is advanced over the guide wire 312 until the driver 150 engages the bone anchor 100. In FIGS. 29 and 30, torque is applied to the outer adapter 152 to screw the bone anchor 100 into the vertebral body 310. In FIG. 31, the driver 150 is removed, leaving the bone anchor 100 in place, with the longitudinal axis of the portal 116 aligned approximately parallel with the longitudinal axis of the spine. The sheath 320, discussed above with reference to FIGS. 18–25, while not shown in the steps discussed with reference to FIGS. 28–31, may nonetheless be used to shield the driver from adjacent tissue in these steps, as will be understood by those skilled in the art.

Figure 32:
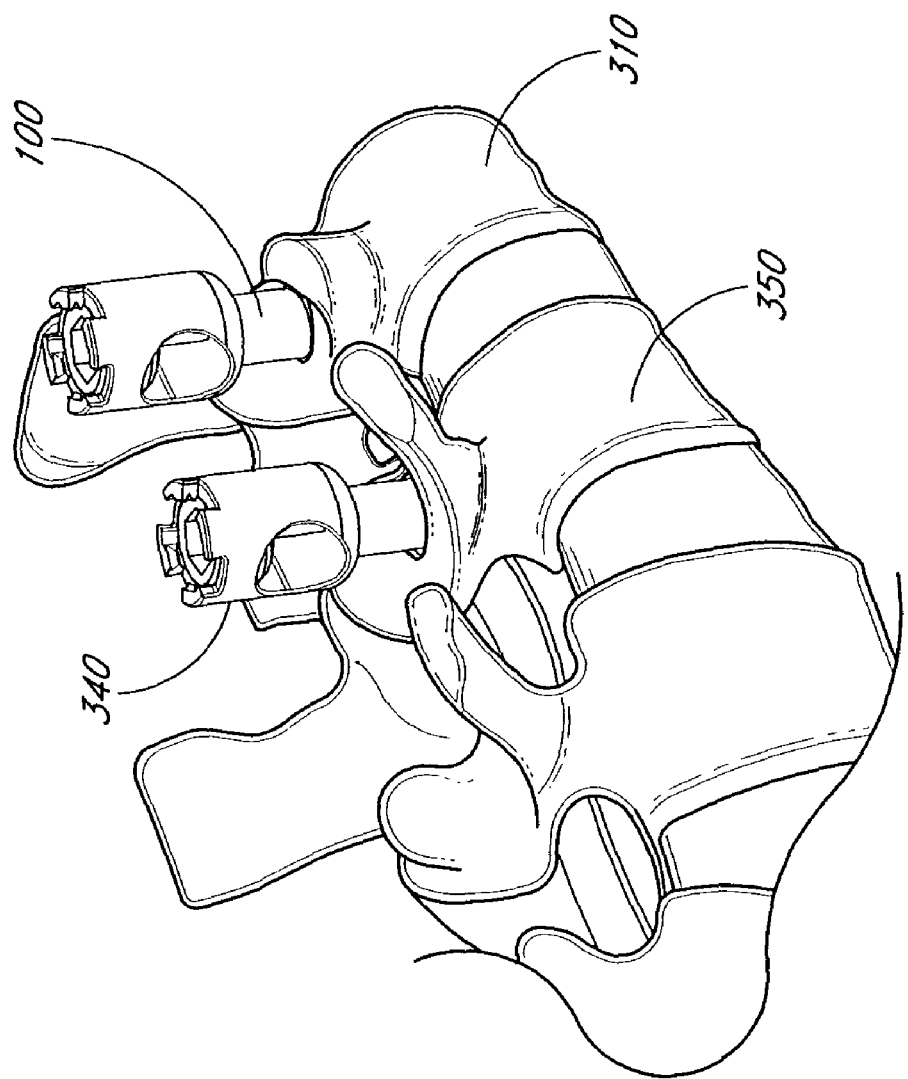
FIG. 32 illustrates two bone anchors positioned in two adjacent vertebral bodies.

In FIG. 32, a second bone anchor 340 has been inserted into another vertebral body 350. While bone anchors 100 and 340 are shown inserted into adjacent vertebral bodies 310 and 350, respectively, the system and methods for minimally invasive spinal fixation according to the embodiments of the present invention are also applicable to non-adjacent vertebral bodies. For example, a first bone anchor may be positioned in a first vertebral body as has been described above. A second bone anchor may be positioned in a second vertebral body, spaced apart from the first vertebral body by one or more intervening third vertebral bodies. The first and second bone anchors may thereafter be connected by the implantation of a linkage rod 200. Alternatively, a third bone anchor may be positioned in a third vertebral body, positioned in between the first and second vertebral bodies to produce, for example, a three level fusion system as will be discussed.

Figure 33:
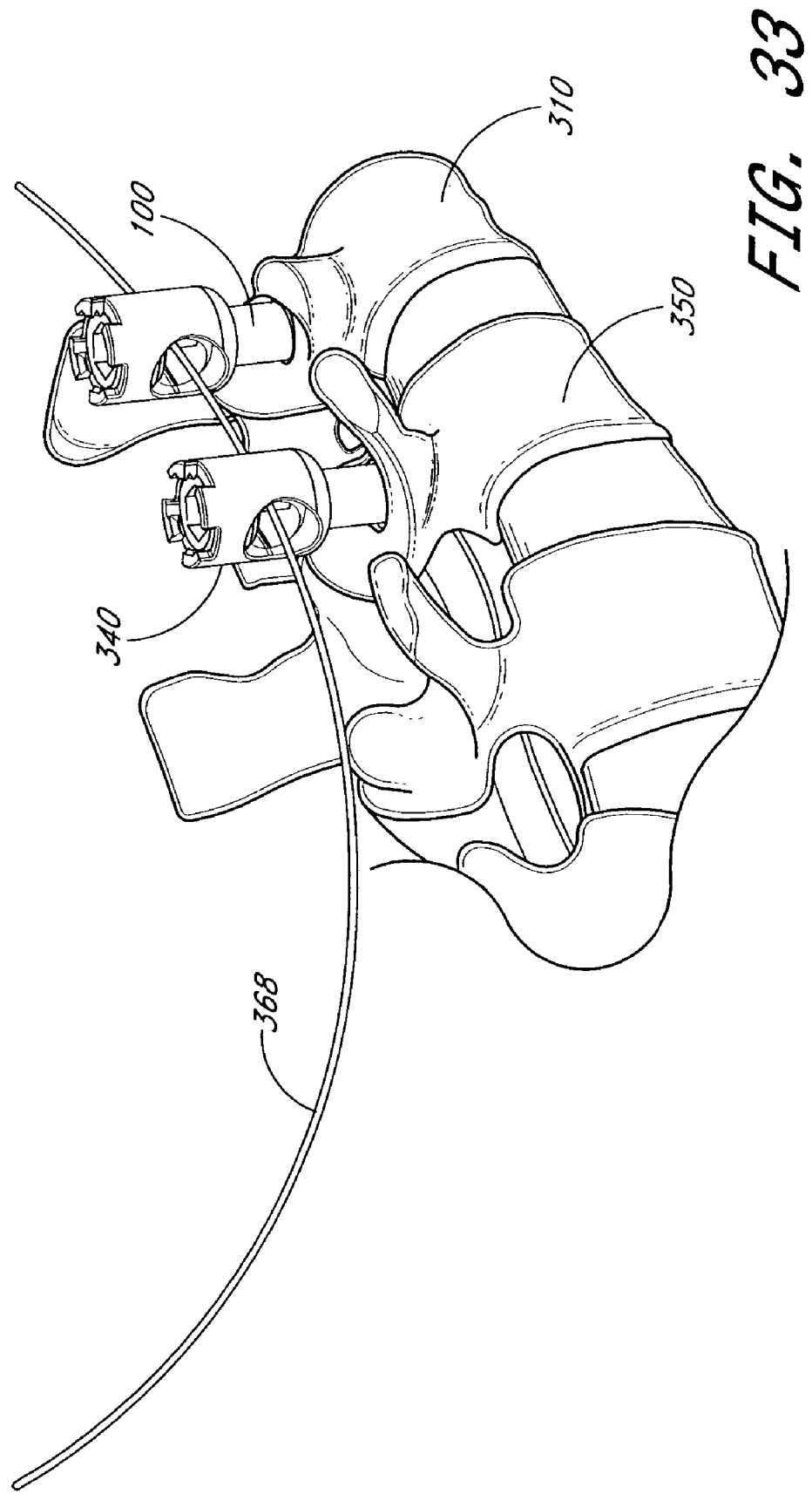
FIG. 33 is a side elevational perspective view of a guidewire positioned through two adjacent bone anchors.

Preferably, after the bone anchors are in place, a guidewire 368 (see FIG. 33 is advanced through the transverse portals 118 of the of bone anchors 100 and 340. Various methods of inserting guide wires are known in the art and the invention is not limited to an particular method. Instead, various methods and devices for inserting a guide wire known to those skilled in the art may be used in accordance with the present invention.

FIGS. 34–40 illustrate a particularly advantageous guide wire insertion device 400 according to one embodiment. The guide wire insertion device comprises a handle 410 and a hollow access needle 450. The handle 410 is detachably joined to the outer adapter 152 of the driver 150. The handle 410 is forked at its proximal end 412. Each fork is provided with a pivot pin 414, which engages the pivot hole 153 (FIG. 28) of the outer adapter 152. The forked proximal end 412 of the handle 410 may be spread slightly to allow the pivot pins 414 to engage the pivot hole 153. The handle 410 swings on its pivot pins 414 at the pivot hole 153 of the outer adapter 152 of the driver 150 to insert the access needle 450 through the transverse portal 116 of the bone anchor 100.

A hollow access needle 450 is attached to the distal end 416 of the handle 410. In one embodiment, the access needle 450 is disposed within an opening 418 at the distal end 416 of the handle 410. A screw (not shown) may be threaded through a screw hole 420 at the distal end 416 of the handle 410 to tighten the access needle 450 within the opening 418. The lengthwise position of the access needle 450 within the opening 418 is therefore adjustable to allow the access needle 450 to be aimed through the transverse portal 116 of the bone anchor 100. In one embodiment, the access needle 450 may be aimed such that it passes through the transverse portal 116 at a point lower (towards the threads 102 in FIG. 2) than the center of the transverse portal 116 because obstructions encountered during the in vivo insertion of the access needle 450 may deflect the needle 450 towards the inside of its curvature and the center of the transverse portal 116.

In several embodiments, the sharp, tapered distal end 452 of the access needle 450 terminates at an opening 454. In one embodiment, the access needle 450 is provided with threaded proximal end 456, the purpose of which is described in further detail below.

Figure 35:
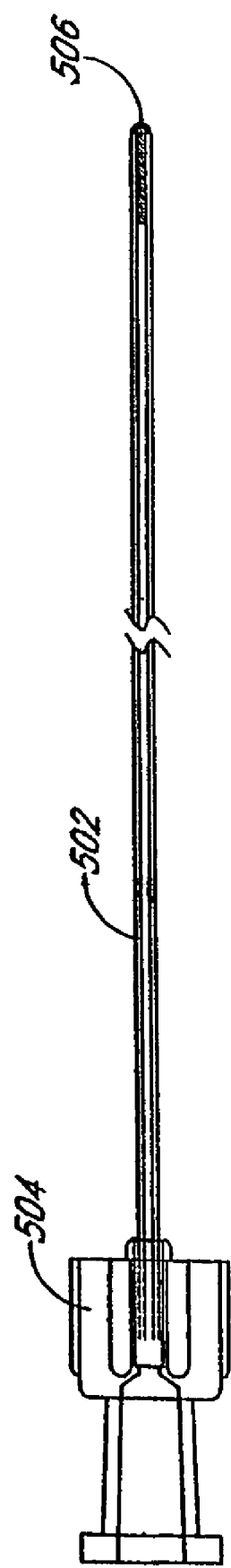
FIG. 35 illustrates a flexible obtuator for positioning within the arcuate arm of the alignment device.

FIG. 35 illustrates a flexible obturator 500 of the guide wire insertion device 400 according to one embodiment. The obturator 500 comprises a tubing 502, a threaded cap 504 on its proximal end and a plug 506 on its distal end. The tubing 502 is sized such that it fits snugly within the hollow access needle 450 and occupies the length of its lumen. The cap 504 can be made with a threaded luer connector which may be tightened onto the threaded proximal end 456 of the access needle 450. The plug 506 may be formed from an adhesive, for example, Loctite 3104, etc. The obturator 500 occupies the lumen of the access needle 450, and minimizes the collection of tissue or other matter within the access needle 450 as it is advanced through the patient.

Figure 36:
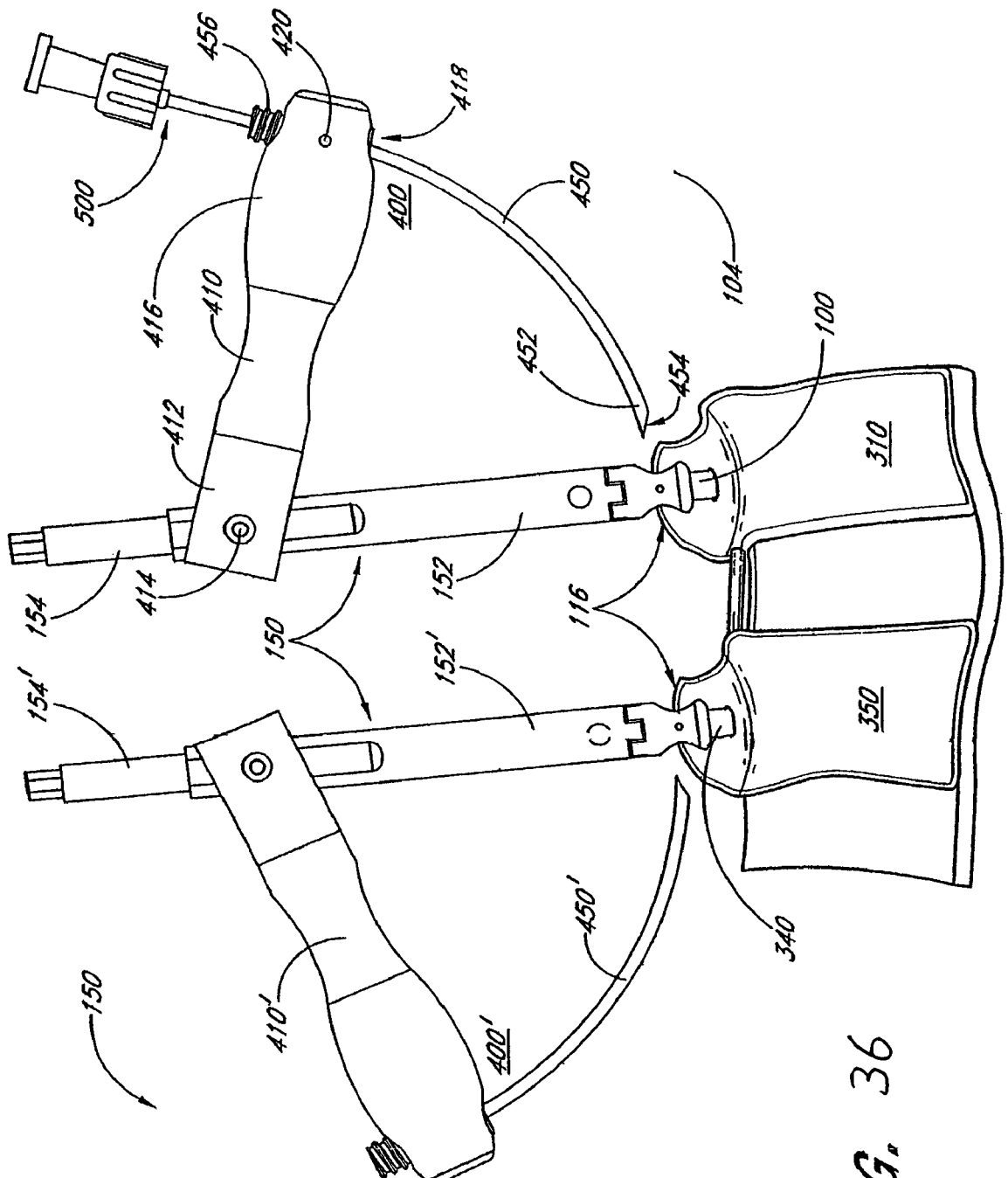
FIG. 36 illustrates a first alignment device coupled to first bone anchor, and a second alignment device coupled to a second bone anchor.

FIG. 36 shows a first guide wire insertion device 400 joined to a first outer adapter 152 engaging a first bone anchor 100 and a second guide wire insertion device 400' joined to the outer adapter 152' engaging a second bone anchor 340. In one embodiment, both handles 410 and 410' are pivoted with respect to outer adapters 152 and 152' to advance access needles 450 and 450' through the patient's tissues and towards the transverse portals 116 of bone anchors 100 and 340, respectively. FIG. 36 also shows an obturator 500 according to one embodiment being inserted into the access needle 450 of the guide wire insertion device 400 as described above with reference to FIG. 35. Preferably, the obturator 500 is inserted into the access needle 450 and threaded onto its threaded proximal end 456 before the access needle 450 is inserted into the patient. Likewise, another obturator 500 may be inserted into the access needle 450'.

Figure 37:
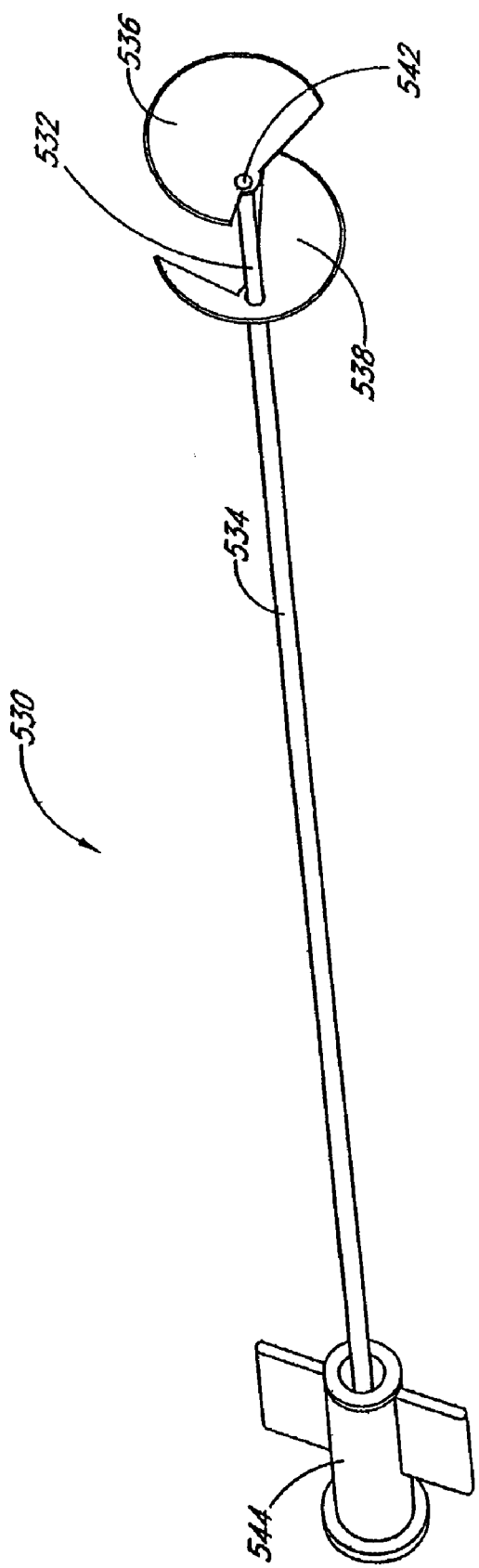
FIG. 37 illustrate a guidewire capture device, for positioning within the arcuate arm on an alignment device.
Figure 38:
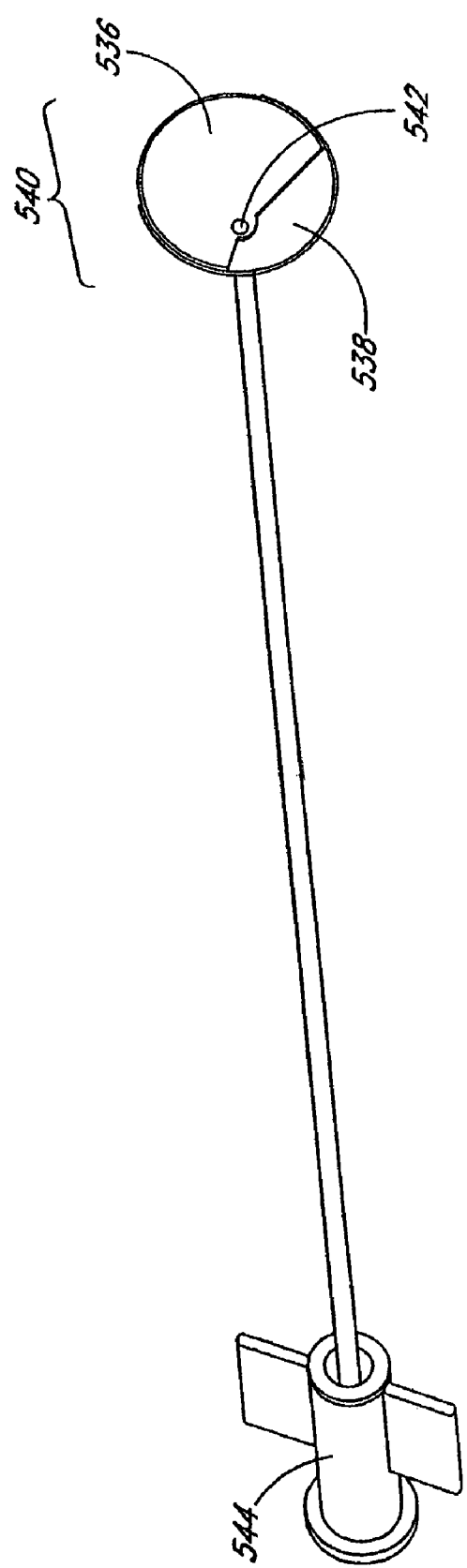
FIG. 38 illustrates the first and second alignment devices, with a guidewire advancing from the first alignment device towards the capture device carried by the second alignment device.

In one embodiment of the present invention, the guide wire insertion device 400 additionally comprises a guide wire snare or capture device 530, illustrated in FIG. 37. The guide wire capture device 530 comprises an inner tubing 532 located coaxially within an outer tubing 534. The inner tubing 532 is provided with an inner half-cone 536 and the outer tubing 534 is provided with an outer half cone 538. The inner half-cone 536 may be furled and retracted within the outer tubing 534. Likewise, the outer half-cone 536 may be furled to ease its insertion into and navigation through the lumen of the hollow access needle 450. Inner half-cone 536 may be rotationally oriented with respect to outer half-cone 538 to form the conical funnel 540 of the guide wire capture device 530, as illustrated in FIG. 38. When a guide wire contacts the conical funnel 540 of the guide wire capture device 530, the guide wire is directed into the lumen 542 of the inner tubing 532. The guide wire capture device 530 also additionally comprises a handle 544 in the illustrated embodiment.

Figure 39:
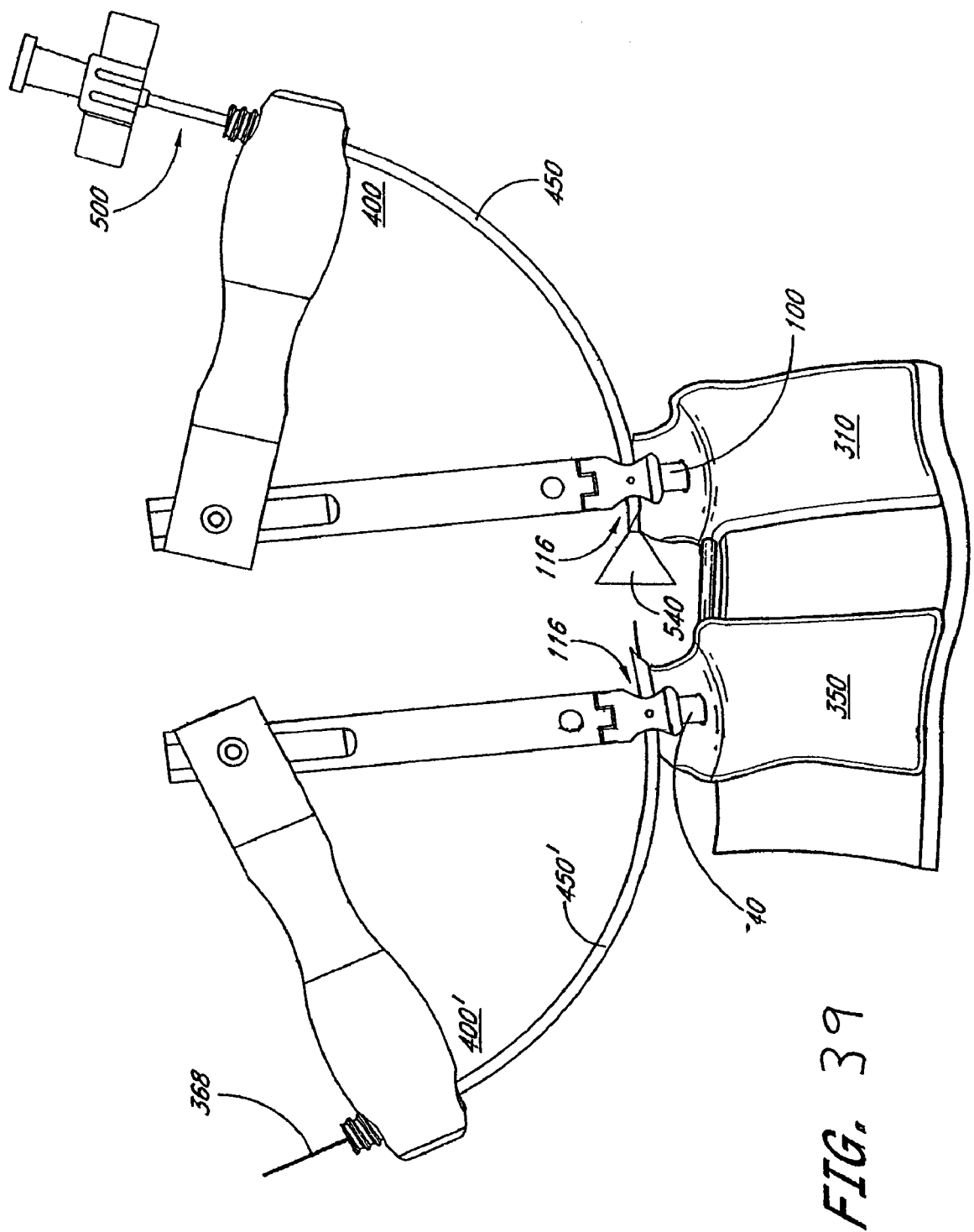
FIG. 39 is an illustration as in FIG. 38, after the guidewire has entered the guidewire capture device and traversed the curved arm on the second alignment device.

In FIG. 39, the access needle 450 has been advanced through the transverse portal 116 of bone anchor 100, and access needle 450' has been advanced through the transverse portal 116 of bone anchor 340. The guide wire capture device 530 is inserted through the lumen of the access needle 450, and its conical funnel 540 is deployed. A guide wire 368 is inserted through the lumen of the access needle 450' and advanced towards the conical funnel 540 of the guide wire capture device 530. When the guide wire 368 contacts the conical funnel 540, the guide wire 368 is directed into the lumen 542 of the inner tubing 532 of the guide wire capture device 530.

Figure 40:
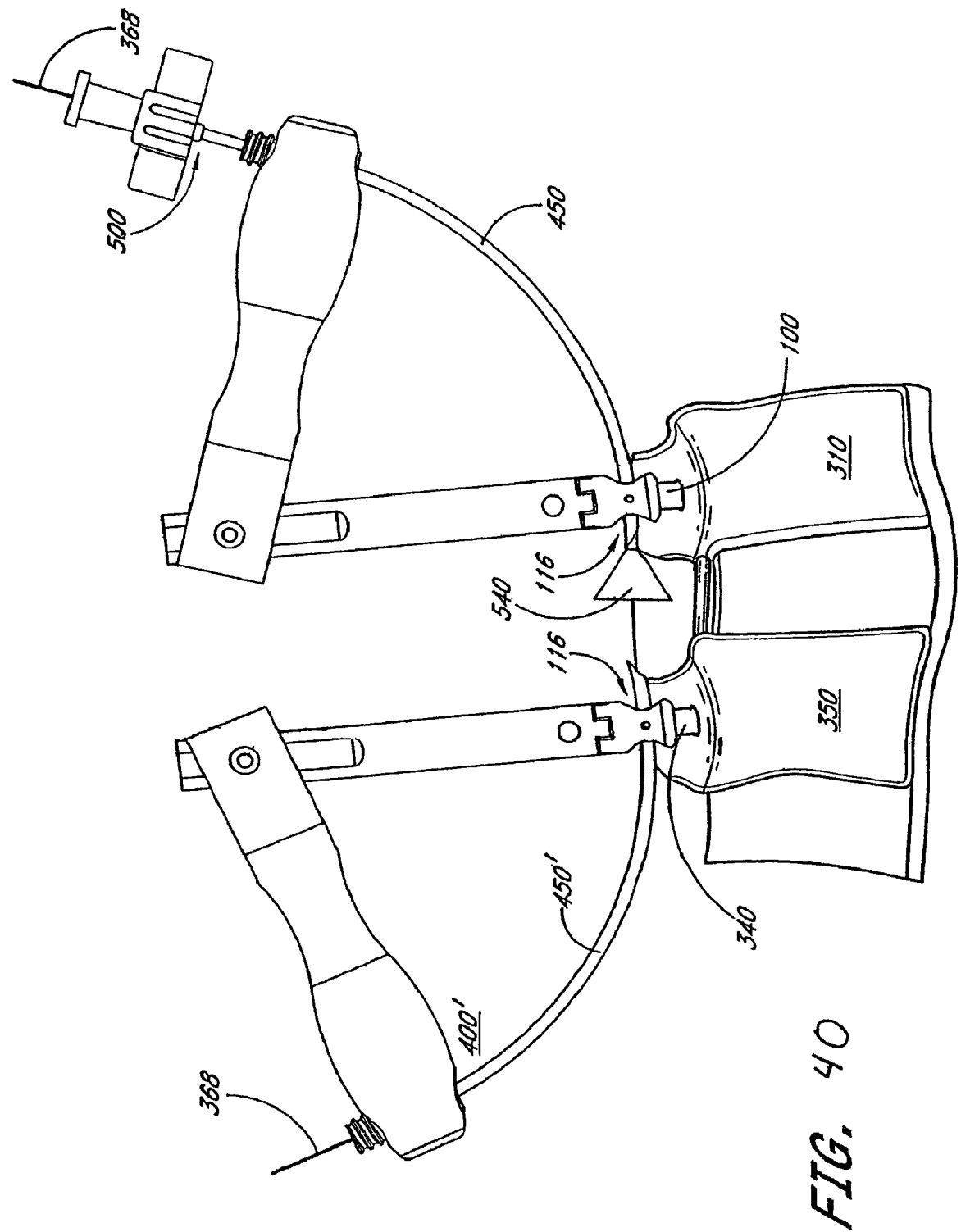
FIG. 40 is a side view of a linkage rod positioned over a guidewire.

In FIG. 40, the guide wire 368 is advanced through the lumen 542 of the inner tubing 532 until it extends past the handle 544 of the guide wire capture device 530 As mentioned above, various methods of inserting guide wires are known in the art and the invention is not limited to the methods disclosed herein. Instead, any method of inserting a guide wire known to those skilled in the art may be used in accordance with the present invention. Following placement of the guide wire 368, the first insertion device 400 and second insertion device 400' may be removed.

In a modified embodiment, only the first the guide wire insertion device 400 may be used to insert the guidewire 368 through the first bone anchor 100. The guidewire 368 may thereafter be pushed through subsequent bone anchors and tissue using traditional techniques with or without the aid of the insertion device 400.

A flexible or curved bone drill (not shown) may be advanced along the guide wire 368 to clear a path between the transverse portals 116 of bone anchors 100 and 340. In one embodiment, the bone drill arm carrying the drill bit is provided with a certain degree of flexibility to allow it to travel along the arcuate, discontinuous and/or non-linear course of the guide wire 368. The bone drill is removed from the guide wire 368 after a path has been cleared between transverse portals 116 of bone anchors 100 and 340.

Figure 34:
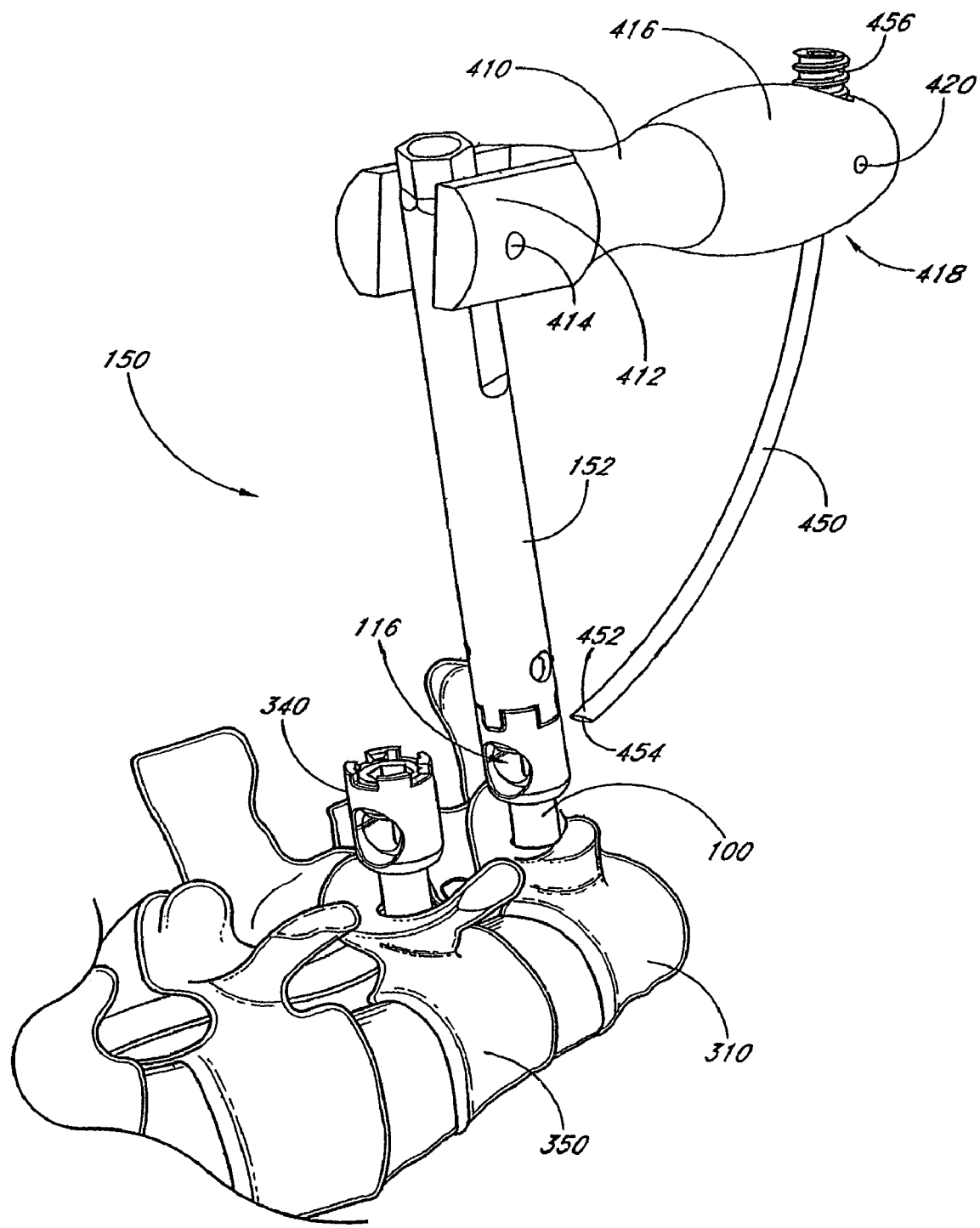
FIG. 34 illustrates an alignment device for positioning a guidewire though a bone anchor in accordance with one aspect of the present invention.
Figure 41:
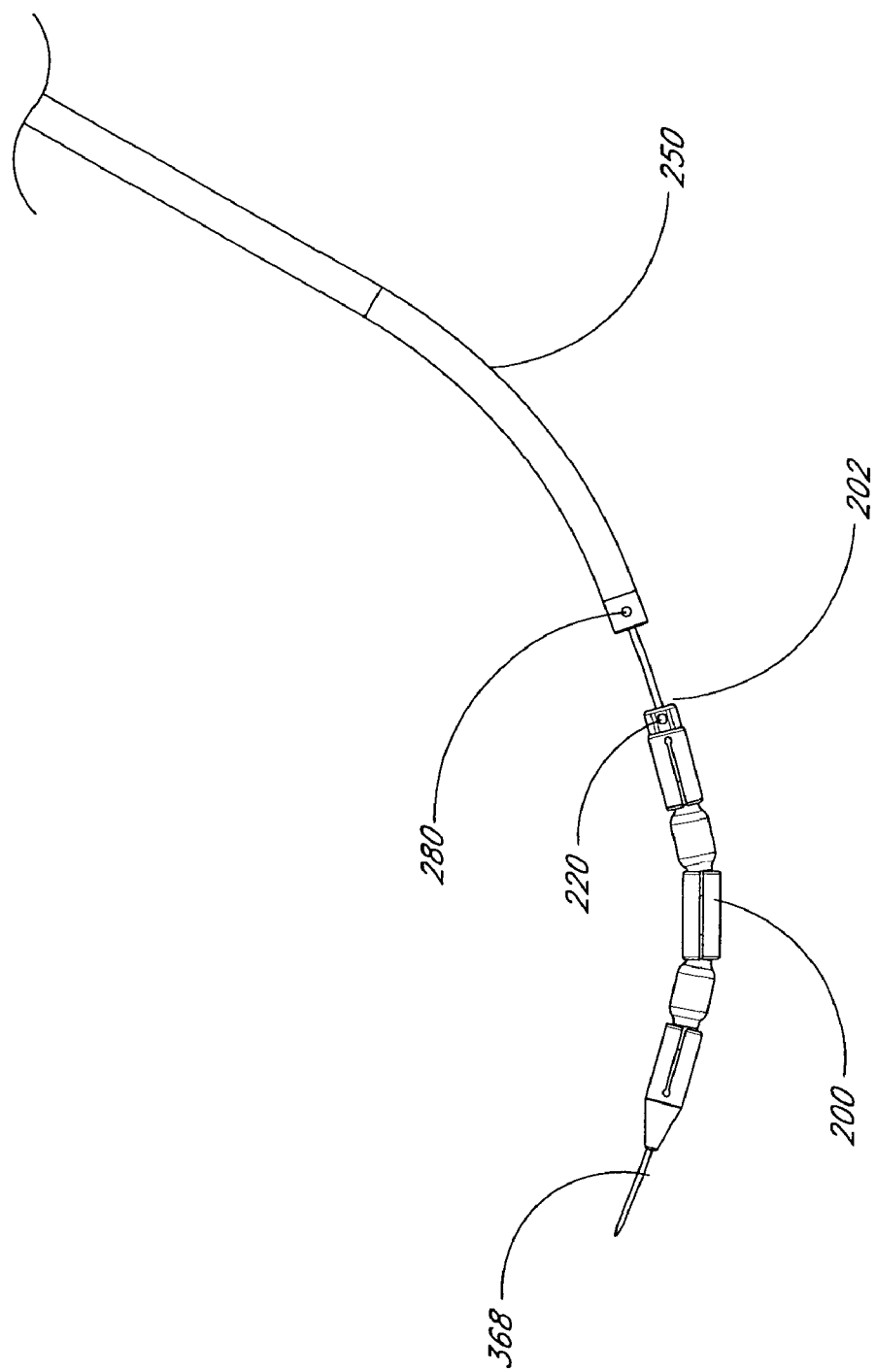
FIG. 41 is an illustration as in FIG. 32, with the linkage rod positioned within the first and second bone anchors.

In FIG. 41, a linkage rod 200 and its insertion tool 250 are shown arranged over the guide wire 368. The linkage rod 200 and insertion tool 250 are described above with reference to FIGS. 3–3A. The linkage rod 200 and insertion tool 250 in the embodiment illustrated in FIG. 41 are provided with slightly different indexing features than the linkage rod and insertion tool described with reference to FIGS. 3–3A. Referring again to FIG. 41 the linkage rod 200 is provided with one or more bumps 220 on its hexagonal proximal end 202. The bumps 220 are complementary with one or more holes 280 at the distal end of the insertion tool 250. In FIG. 34, the linkage rod 200 is detached from the insertion tool 250. The attachment of the linkage rod 200 to the insertion tool 250 is described above with reference to FIGS. 5 and 5A.

In FIG. 41, the insertion tool 250 is used to advance the linkage rod 200 over the guide wire 368 towards the bone anchors 100 and 340. While the linkage rod 200 is inserted from a rostral or sacral approach (tail-to-head) in the illustrated embodiment, it may also be inserted from a caudal approach (head-to-tail) in another embodiment.

Figure 42:
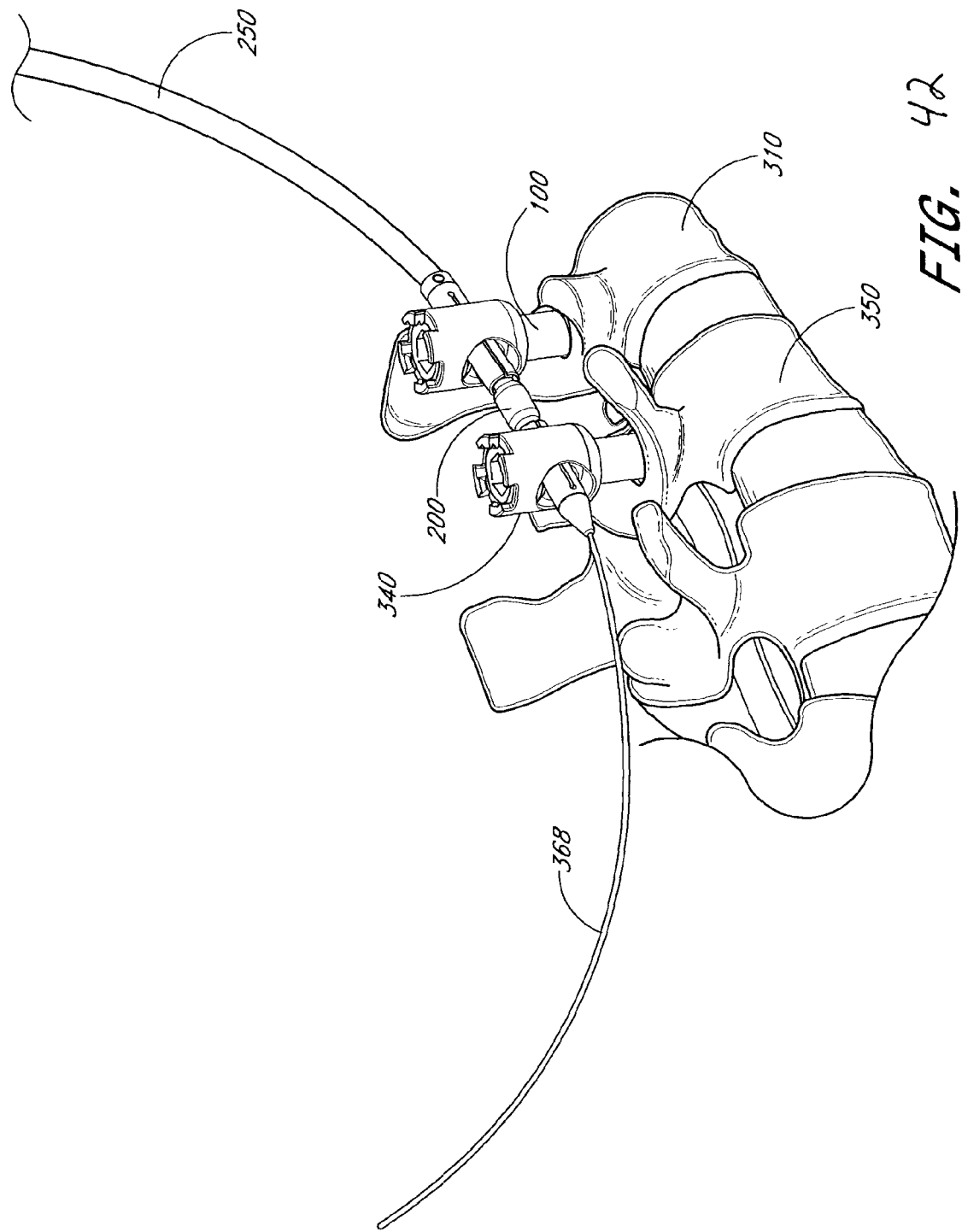
FIG. 42 is an illustration as in FIG. 32, with a driver in position to lock the first bone anchor to the linkage rod.

In FIG. 42, the linkage rod 200 is inserted through the respective transverse portals 116 within bone anchors 100 and 340. As mentioned above, the linkage rod is provided with one or more joints 208. The joints 208 provide the linkage rod 200 with a degree of flexibility. As such, even if the transverse portals 116 are not aligned the linkage rod 200 can track over the non-linear, curved or disjoined path as defined by the guidewire 368 and extending between portals 116.

Figure 43:
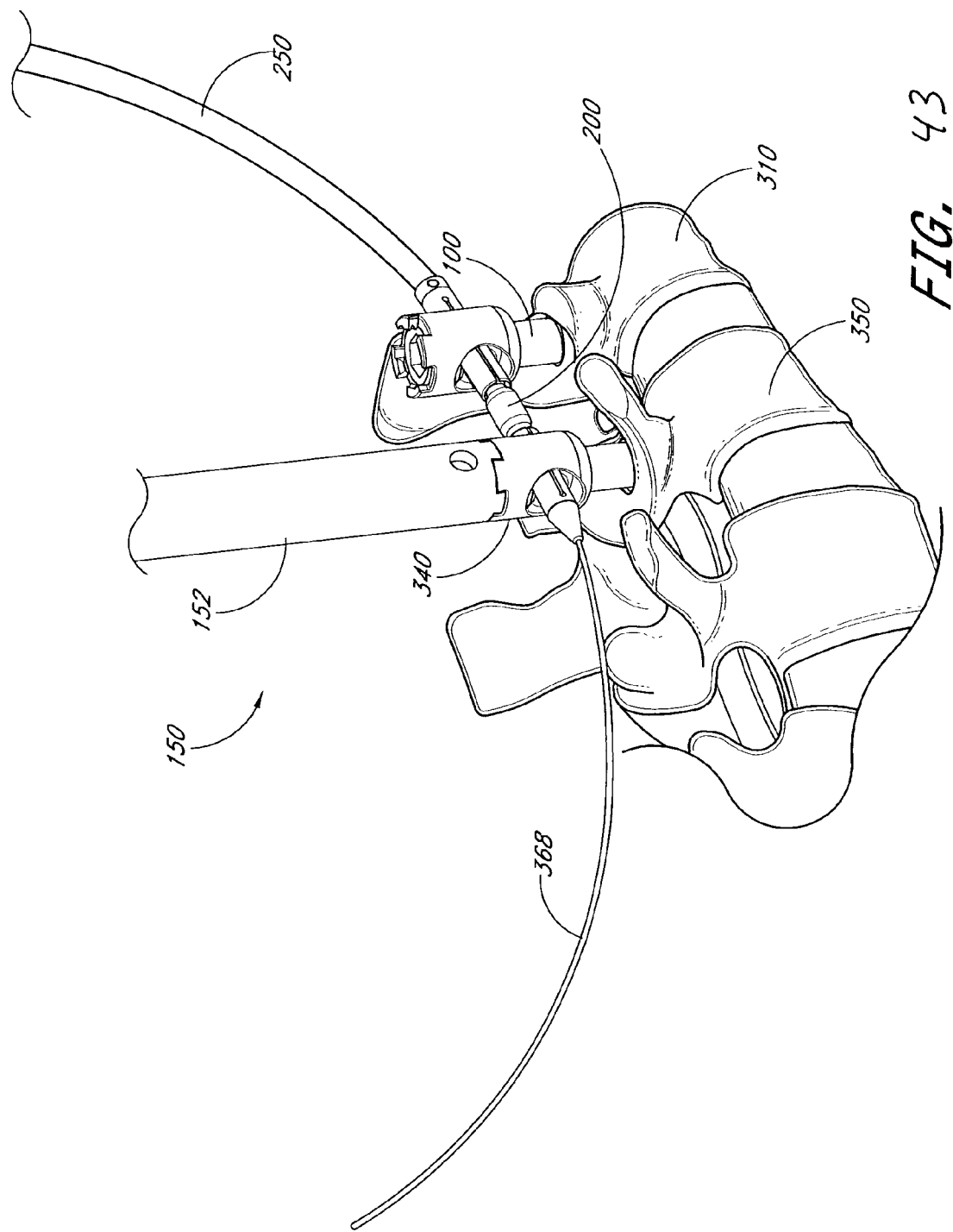
FIG. 43 is an illustration as in FIG. 32, with a portion of the driver tool proximally retracted.
Figure 44:
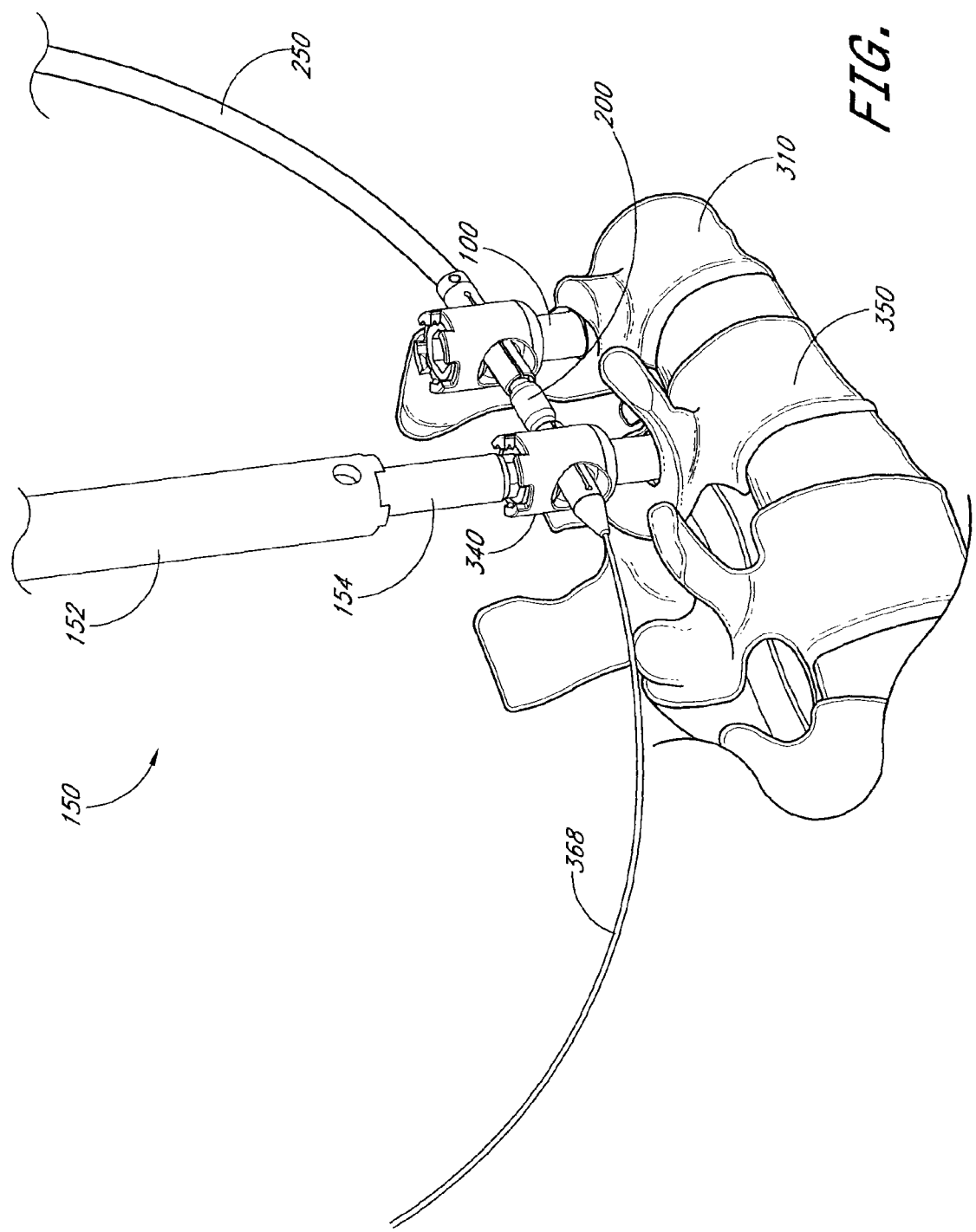
FIG. 44 is an illustration as in FIG. 43, with the driver tool retracted, the first and second bone anchors locked onto the linkage rod.

As shown in FIGS. 43–44, the inner adapter 154 of the driver 150 may be used to tighten the locking cap 106 within the bone anchor 340, fixing the linkage rod 200 within the bone anchor 340 and fixing the angular relationship of the joint 208, as described above with reference to FIGS. 2–3A and/or the connector 104. The outer adapter 152 of the driver 150 engages the head of bone anchor 340 to prevent it from rotating as the locking cap is tightened. The engagement between the bone anchor 340 and the driver 150 is described above with reference to FIGS. 1–2A in the context of bone anchor 100.

Figure 45:
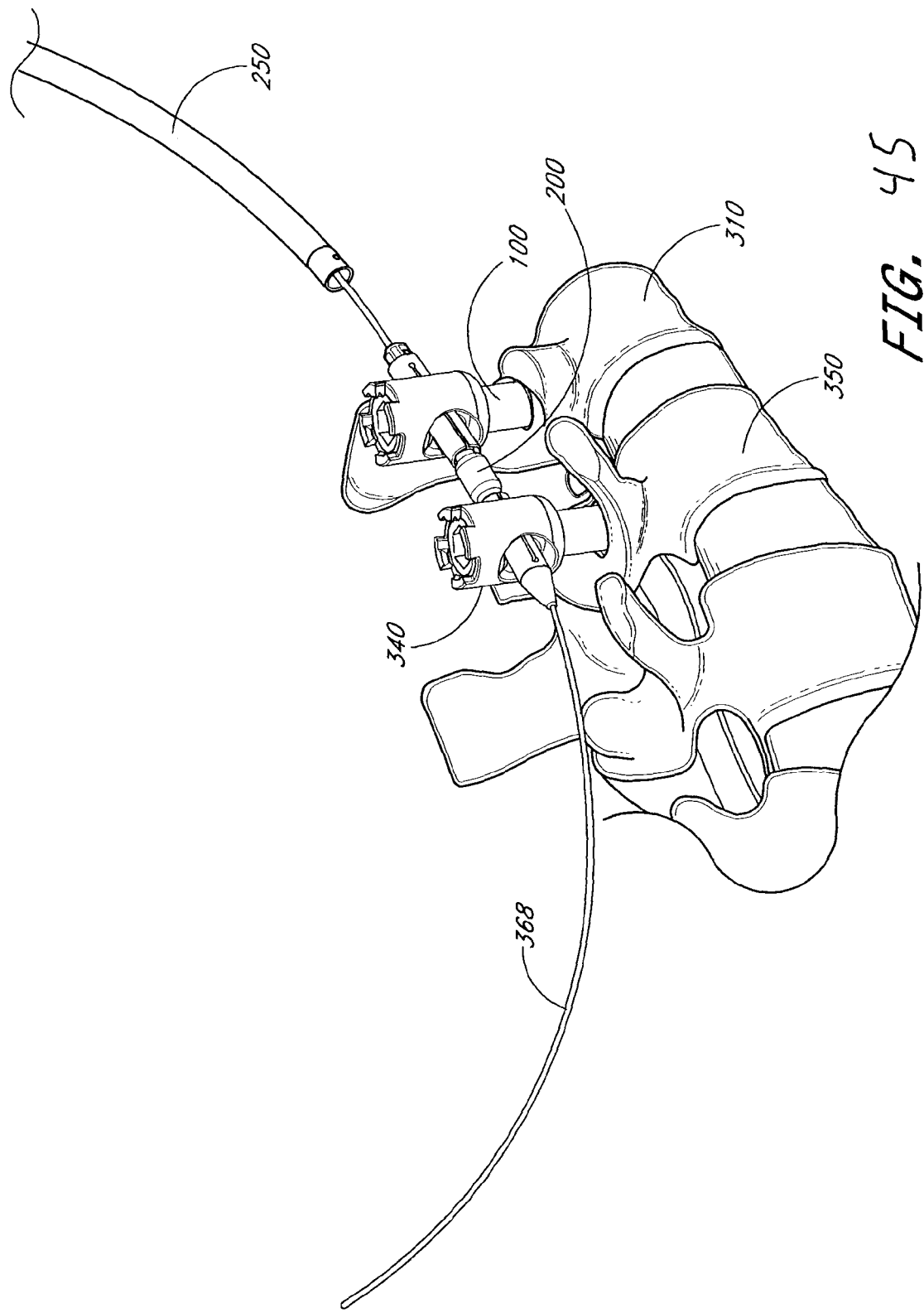
FIG. 45 is an illustration as in FIG. 44, with the insertion tool decoupled from the linkage rod.

In FIG. 45, the driver 150 (comprising the outer adapter 152 and the inner adapter 154) is withdrawn from the bone anchor 340. The locking cap 106 in the bone anchor 100 is similarly tightened, fixing the linkage rod 200 within the bone anchor 100.

Figure 46:
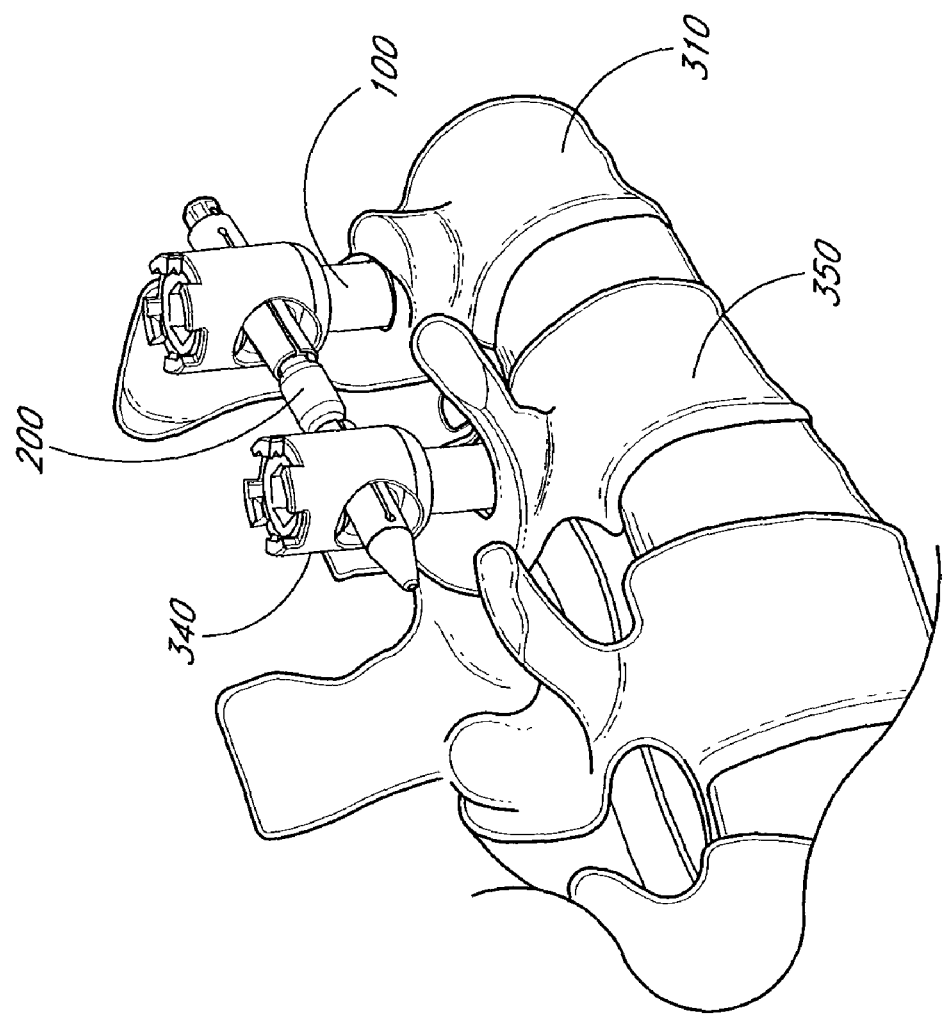
FIG. 46 is an illustration as in FIG. 45, with the insertion tool and the guidewire removed from the linkage rod, illustrating a formed in place one level posterior fusion device in accordance with the present invention.

In FIG. 46, the insertion tool 250 is released from the linkage rod 200. The attachment and detachment of the linkage rod 200 to and from the insertion tool 250 is discussed above with reference to FIGS. 5 and 5A. Afterwards, the driver 150, the sheath 320 and the guide wire 368 are removed from the patient. As such, FIG. 46 illustrates the percutaneously assembled in place prosthesis resulting from the procedure described above, comprising the bone anchors 100, 340 and the linkage rod 200.

Figure 47:
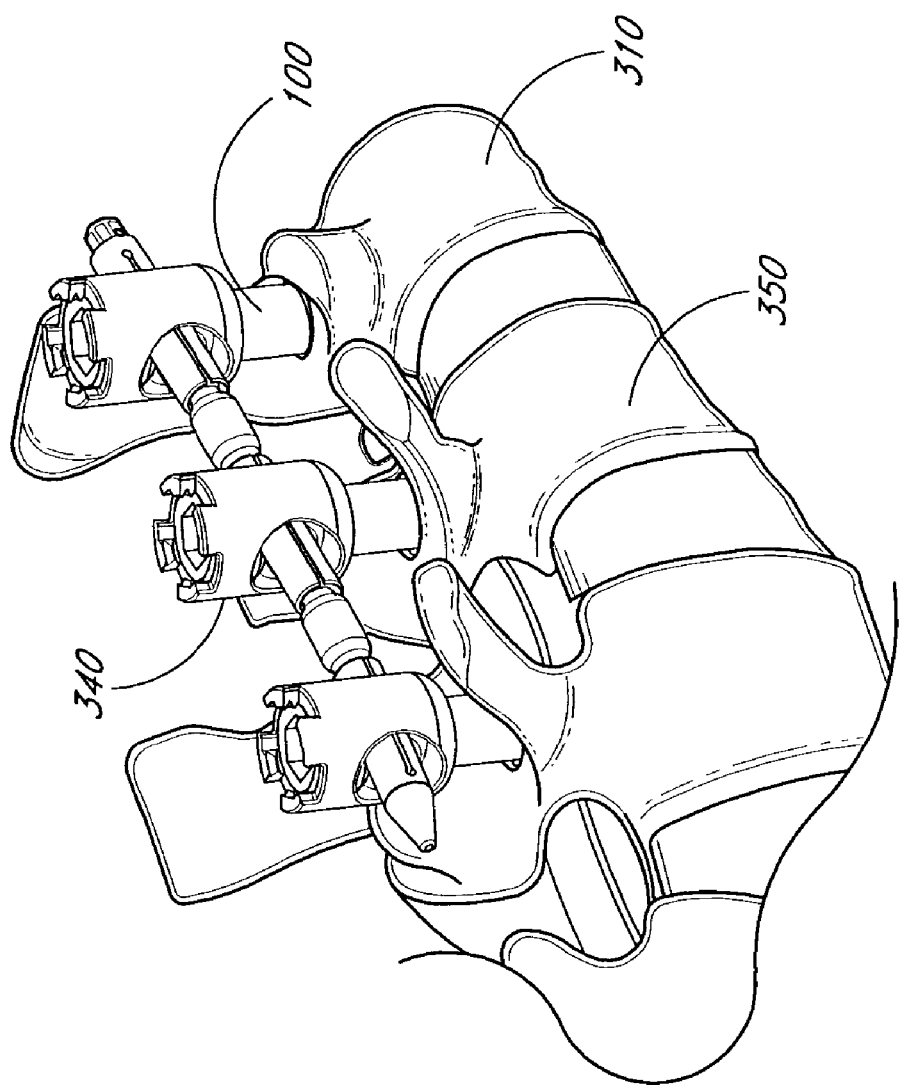
FIG. 47 is an illustration as in FIG. 45, showing a two level fusion or fixation device, percutaneously assembled in accordance with the present invention.

FIG. 47 illustrates a three level prosthesis comprising an additional bone anchor inserted into an additional adjacent vertebral body and the linkage rod of FIGS. 4–4B, to provide a three level spinal fusion.

In one embodiment, the transverse portal 116 of the proximal bone anchor is provided with a proximal opening having a first diameter and distal opening having a second, smaller diameter. The outside diameter of the proximal segment 230 is dimensioned relative to the portal 116 such that it can pass through the proximal opening on the transverse portal 116 but cannot pass distally through the distal opening of the transverse portal 116. In this manner, the clinician can perceive tactile feedback once the proximal segment 230 has been distally advanced into position within the head 108. This same construction can be utilized on the distal bone anchor as well, such that distal advancement of the first segment through the transverse portal 116 is limited. In modified embodiments, the outside diameter of the first and proximal segments 204, 230 may be tapered to achieve the result described above.

Not all of the steps described above are critical to the minimally invasive implantation of posterior fixation hardware. Accordingly, some of the described steps may be omitted or performed in an order different from that disclosed. Further, additional steps may be contemplated by those skilled in the art in view of the disclosure herein, without departing from the scope of the present invention. In addition, the specific dimensions and angles mentioned above can be readily varied depending upon the intended application, as will be apparent to those of skill in the art in view of the disclosure herein.

The present inventors contemplate the interchangeability of and recombination of various structural and method elements in the foregoing description. For example, the guidewire may be positioned through portals of adjacent bone anchors utilizing either the procedures disclosed in the copending patent applications previously incorporated by reference herein. As a further alternative, a tubular sleeve may be advanced over the guidewire and through the portals on bone anchors 100, with the guidewire thereafter removed. The linkage rod 200 may thereafter be advanced through the tubular sleeve.

The various materials, methods and techniques described above provide a number of ways to carry out the invention. Of course, it is to be understood that not necessarily all objectives or advantages described may be achieved in accordance with any particular embodiment described herein. Thus, for example, those skilled in the art will recognize that the components of the system may be made and the methods may be performed in a manner that achieves or optimizes one advantage or group of advantages as taught herein without necessarily achieving other objectives or advantages as may be taught or suggested herein.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A prosthesis for minimally invasive posterior fixation, comprising:
   a bone anchor having a head;
   a transverse portal extending through opposing sidewalls of said head along an axis transverse to a central axis of said bone anchor, said opposing sidewalls being substantially closed above said transverse portal;
   a first segment of a rod extending through said transverse portal, said first segment defining a first surface;
   a second segment of a rod having a second complementary surface;
   a joint formed at least in part by said first surface and said second surface; and
   a locking cap which in response to lateral movement secures said first segment within said portal and fixes the angular relationship of the joint.

2. The prosthesis of claim 1, wherein said rod is adapted to be detachably secured to an insertion tool used to insert said rod into said portal.

3. The prosthesis of claim 1, further comprising a third segment of the rod, said third segment defining a socket for receiving a ball positioned on said second segment.

4. The prosthesis of claim 3, further comprising a second bone anchor having a head, a transverse portal and a locking cap which in response to lateral movement secures said third segment within the portal of the second bone anchor and fixes the angular relationship between the third and second segments.

5. The prosthesis assembly of claim 4, wherein the third segment is configured to be secured to an insertion tool used to insert said rod into said portals of said bone anchors.

6. The prosthesis of claim 4, wherein said first segment, said second segment and said third segment include a central lumen, which is configured such that said first second and third segments can travel over a guidewire.

7. The prosthesis of claim 4, wherein the transverse portal of said second bone anchor is substantially closed with respect to a central axis of said second bone anchor.

8. The prosthesis of claim 7, wherein said first segment, said second segment and said third segment include a central lumen, which is configured such that said first second and third segments can travel over a guidewire.

9. The prosthesis of claim 4, wherein said first segment has distal end and said transverse portal of said second bone anchor is configured such that said distal end of said first segment can be advanced entirely through said transverse portal of said second bone anchor.

10. The prosthesis of claim 1, wherein said first segment and second segment include a central lumen, which is configured such that the first and second segments can be advanced over a guidewire.

11. The prosthesis of claim 1, wherein said first segment has distal end and said transverse portal is configured such that said distal end of said first segment can be advanced through a first end of said portal.

12. The prosthesis of claim 1, wherein said first segment has distal end and said transverse portal is configured such that said distal end of said first segment can be advanced entirely through said transverse portal.

13. A prosthesis for minimally invasive posterior fixation, comprising:
- a bone anchor having a head;
- a transverse portal extending through said head along an axis transverse to a central axis of said bone anchor;
- a first segment of a rod extending through said transverse portal, said first segment defining a first surface;
- a second segment of a rod having a second complementary surface;
- a joint formed at least in part by said first surface and said second surface; and
- a locking cap which in response to lateral movement secures said first segment within said portal and fixes the angular relationship of the joint;
- wherein said first segment further comprises at least one compression gap.

14. The prosthesis of claim 13, wherein said rod is adapted to be detachably secured to an insertion tool used to insert said rod into said portal.

15. The prosthesis of claim 13, further comprising a third segment of the rod, said third segment defining a socket for receiving a ball positioned on said second segment.

16. The prosthesis of claim 15, further comprising a second bone anchor having a head, a transverse portal and a locking cap which in response to lateral movement secures said third segment within the portal of the second bone anchor and fixes the angular relationship between the third and second segments.

17. The prosthesis assembly of claim 16, wherein the third segment is configured to be secured to an insertion tool used to insert said rod into said portals of said bone anchors.

18. The prosthesis of claim 13, wherein said rod includes a central lumen, which is configured such that said rod can be advanced over a guidewire.

19. The prosthesis of claim 13, wherein said first segment has distal end and said transverse portal is configured such that said distal end of said first segment can be advanced through a first end of said portal.

20. The prosthesis of claim 13, wherein said first segment has distal end and said transverse portal is configured such that said distal end of said first segment can be advanced entirely through said transverse portal.

21. A prosthesis for minimally invasive posterior fixation, comprising:
- a first bone anchor having a head and a transverse portal extending through said head along an axis transverse to a central axis of said first bone anchor;
- a second bone anchor having a head and a transverse portal extending through said head along an axis transverse to a central axis of said second bone anchor;
- a first segment of a rod extending through said transverse portal of said first bone anchor, said first segment defining a first surface, said first segment being configured such that it can be advanced entirely through said transverse portal of said second bone anchor;
- a second segment of a rod having a second complementary surface;
- a joint formed at least in part by said first surface and said second surface; and
- a locking cap that is configured for lateral movement within said head of said first bone anchor and is configured such that lateral movement within said head secures said first segment within said portal and fixes the angular relationship of the joint.

22. The prosthesis of claim 21, wherein said rod is adapted to be detachably secured to an insertion tool used to insert said rod into said portal.

23. The prosthesis of claim 21, further comprising a third segment of the rod, said third segment defining a socket for receiving a ball positioned on said second segment.

24. The prosthesis of claim 23, further comprising a cap for the second bone anchor that in response to lateral movement secures said third segment within the portal of the second bone anchor and fixes the angular relationship between the third and second segments.

25. The prosthesis assembly of claim 24, wherein the third segment is configured to be secured to an insertion tool used to insert said rod into said portals of said bone anchors.

26. The prosthesis of claim 21, wherein said rod includes a central lumen, which is configured such that the rod can be advanced over a guidewire.

27. The prosthesis of claim 21, wherein said first segment has distal end and said transverse portal of said first bone anchor is configured such that said distal end of said first segment can be advanced through a first end of said transverse portal of said first bone anchor.

28. The prosthesis of claim 21, wherein said first segment has distal end and said transverse portal is configured such that said distal end of said first segment can be advanced entirely through said transverse portal of said first bone anchor.

29. A prosthesis for minimally invasive posterior fixation, comprising:
- a bone anchor having a head;
- a transverse portal extending through said head along an axis transverse to a central axis of said bone anchor;
- a first segment of a rod extending through said transverse portal, said first segment defining a first surface;
- a second segment of a rod having a second complementary surface;
- a joint formed at least in part by said first surface and said second surface;
- means for securing said first segment within said portal and fixing the angular relationship of the joint; and
- a guidewire lumen extending through said first and second segments of the rod.

30. The prosthesis of claim 29, wherein said rod is adapted to be detachably secured to an insertion tool used to insert said rod into said portal.

31. The prosthesis of claim 29, wherein further comprising a third segment of the rod, said third segment defining a socket for receiving a ball positioned on said second segment.

32. The prosthesis of claim 31, wherein said guidewire lumen extends through said third segment 33. The prosthesis assembly of claim 31, wherein the third segment is configured to be secured to an insertion tool used to insert said rod into said portals of said bone anchors.

34. A prosthesis for minimally invasive posterior fixation, comprising:
- a first bone anchor having a head and a transverse portal extending through said head along an axis transverse to a central axis of said first bone anchor;
- a second bone anchor having a head and a transverse portal extending through said head along an axis transverse to a central axis of said second bone anchor;
- a first segment of a rod extending through said transverse portal of said first bone anchor, said first segment defining a first surface;
- a second segment of a rod having a second complementary surface;

a joint formed at least in part by said first surface and said second surface, said joint configured to allow an angular orientation of said first and second segments to be adjusted within a cone having a vertex located between said first and second bone anchors; and a locking cap which in response to lateral movement secures said first segment within said transverse portal of said first bone anchor and fixes the angular relationship of the joint.

35. The prosthesis of claim 34, wherein said rod is adapted to be detachably secured to an insertion tool used to insert said rod into said portal.

36. The prosthesis of claim 34, wherein further comprising a third segment of the rod, said third segment defining a socket for receiving a ball positioned on said second segment.

37. The prosthesis of claim 34, wherein said first segment and second segment include a central lumen, which is configured such that the first and second segments can be advanced over a guidewire.

38. The prosthesis of claim 34, wherein said first segment is configured such that it can be advanced entirely through said transverse port of said second bone anchor.

* * * * *